(12) United States Patent
Deckwer et al.

(10) Patent No.: US 7,867,946 B2
(45) Date of Patent: Jan. 11, 2011

(54) LIQUID FORMULATION

(75) Inventors: Roland Deckwer, Frankfurt (DE);
Detlev Haase, Frankfurt (DE);
Hans-Peter Krause, Hofheim (DE);
Gerhard Schnabel, Elsenfeld (DE)

(73) Assignee: Bayer CropScience AG,
Monheim-Am-Rhein (DE)

( * ) Notice: Subject to any disclaimer, the term of this patent is extended or adjusted under 35 U.S.C. 154(b) by 0 days.

(21) Appl. No.: 11/435,173

(22) Filed: May 16, 2006

(65) Prior Publication Data

US 2006/0205596 A1    Sep. 14, 2006

Related U.S. Application Data

(63) Continuation of application No. 10/901,422, filed on Jul. 28, 2004, now abandoned.

(30) Foreign Application Priority Data

Jul. 28, 2003   (DE) ................. 103 34 301

(51) Int. Cl.
*A01N 25/26* (2006.01)
*A01N 43/64* (2006.01)
*A01N 43/647* (2006.01)
*A01N 43/707* (2006.01)

(52) U.S. Cl. ............... 504/100; 504/133; 504/134; 504/229; 504/261

(58) Field of Classification Search .......... 504/103, 504/105, 106, 100, 133, 134, 229, 261
See application file for complete search history.

(56) References Cited

U.S. PATENT DOCUMENTS

| | | | |
|---|---|---|---|
| 4,599,412 A | 7/1986 | Sandell | |
| 4,671,817 A | 6/1987 | Wexler | |
| 4,683,000 A | 7/1987 | Petersen | |
| 5,731,264 A | 3/1998 | Narayanan et al. | |
| 6,479,432 B1 | 11/2002 | Sixl | |
| 6,559,098 B1 | 5/2003 | Bratz et al. | |
| 6,770,594 B2 * | 8/2004 | Bickers et al. | ............. 504/212 |
| 2002/0016263 A1 * | 2/2002 | Wurtz et al. | ............. 504/362 |
| 2004/0097378 A1 | 5/2004 | Maier et al. | |

FOREIGN PATENT DOCUMENTS

| | | |
|---|---|---|
| CA | 1 247 880 | 1/1989 |
| CA | 2438992 | 9/2002 |
| CA | 2 068 824 | 12/2002 |
| CA | 2 068 826 | 1/2003 |
| DE | 101 08 472 | 9/2002 |
| EP | 0 163 598 | 12/1985 |
| EP | 0 245 058 | 11/1987 |
| EP | 0 313 317 | 4/1989 |
| EP | 0 514 768 | 11/1992 |
| EP | 0 514 769 | 11/1992 |
| EP | 0 554 015 | 8/1993 |
| EP | 0 764 404 | 3/1997 |
| JP | 62155202 | * 7/1987 |
| JP | 2000095620 | 4/2000 |
| WO | WO-93/13658 | 7/1993 |
| WO | WO-98/34482 | 8/1998 |
| WO | WO-01/30156 | 5/2001 |
| WO | WO-01/82693 | 11/2001 |
| WO | WO-02/067676 | 9/2002 |
| WO | WO-2004/054360 | 7/2004 |
| WO | WO-2004/054364 | 7/2004 |

* cited by examiner

*Primary Examiner*—Alton N Pryor
(74) *Attorney, Agent, or Firm*—Connolly Bove Lodge & Hutz LLP

(57) ABSTRACT

The present invention relates to a liquid formulation, comprising
a) one or more herbicidally active compounds from the group of the ALS inhibitors,
b) one or more organic solvents, and
c) one or more inorganic salts.

The liquid formulation is suitable for use in crop protection.

29 Claims, No Drawings

LIQUID FORMULATION

This application is a continuation of application Ser. No. 10/901,422 filed Jul. 28, 2004, which claims foreign priority of German application DE 10334301.6 filed Jul. 28, 2003.

The present invention relates to the field of formulations of crop protection agents. In particular, the invention relates to liquid formulations comprising herbicidally active compounds from the group of the ALS inhibitors (acetolactate synthetase inhibitors).

In general, active compounds for crop protection are not employed in pure form. Depending on the area of use and the type of use, and on physical, chemical and biological parameters, the active compound is used as an active compound formulation in a mixture with customary auxiliaries and additives. Also known are combinations with further active compounds for widening the activity spectrum and/or for protecting crop plants (for example by safeners, antidotes).

In general, formulations of active compounds for crop protection should have high chemical and physical stability, should be easy to apply and easy to use and have broad biological action combined with high selectivity.

Herbicidally active compounds from the group of ALS inhibitors, such as sulfonylureas, may have high chemical reactivity and may tend to be degraded chemically, for example by hydrolysis.

One possibility of formulating chemically unstable active compounds is the preparation of solid formulations. Thus, formulations of ALS inhibitors, such as active compounds from the group of the sulfonylureas, in the form of powders, granules and tablets are known (for example in EP 764404, WO 9834482, WO 9313658). However, the processes for preparing solid formulations, for example in the form of granules and tablets, are generally complicated, in particular when auxiliaries and additives or active compounds having a low melting point are incorporated. Moreover, solid formulations are generally more difficult to apply and less user-friendly.

Liquid formulations of ALS inhibitors, such as sulfonylureas, are described, for example, in U.S. Pat. Nos. 4,599,412, 4,683,000, 4,671,817, EP 0245058, WO 01/82693, EP 0313317, EP 0514768, EP 0163598 and EP 0514769.

It was an object of the present invention to provide an improved formulation of crop protection agents, which formulation has high chemical and physical stability and high biological effectiveness and crop plant compatibility.

This object is achieved by the specific liquid formulation of the present invention.

Accordingly, the present invention relates to a liquid formulation comprising a) one or more herbicidally active compounds from the group of the ALS inhibitors, b) one or more organic solvents, and c) one or more inorganic salts.

In addition, the liquid formulation according to the invention may optionally also comprise further components, for example:

d) one or more agrochemically active compounds different from a), e) one or more sulfosuccinates, and/or f) customary auxiliaries and additives.

The liquid formulation according to the invention is based on organic solvents b). Here, the further components of the liquid formulation may be dissolved completely, dissolved partially and suspended partially or else be suspended completely in the organic solvents. The liquid formulation can, for example, be an emulsion concentrate (EC) or an oil suspension concentrate (OD) and is preferably an oil suspension concentrate.

Suitable ALS inhibitors a) are, for example, compounds from the group of the imidazolinones, pyrimidinyloxypyridinecarboxylic acid derivatives, pyrimidyloxybenzoic acid derivatives or sulfonamides, such as triazolopyrimidinesulfonamides or sulfonylaminocarbonyltriazolinones, preferably phenylsulfonylaminocarbonyltriazolinones, for example flucarbazone or propoxycarbazone and/or salts thereof, or sulfonylureas, preferably phenylsulfonylureas.

Preferred ALS inhibitors originate from the group of the sulfonylureas, for example pyrimidinyl- or triazinylaminocarbonyl[benzene-, -pyridine-, -pyrazole-, -thiophene- and -(alkylsulfonyl)alkylamino]sulfamides. Preferred substituents on the pyrimidine ring or the triazine ring are alkoxy, alkyl, haloalkoxy, haloalkyl, halogen or dimethylamino, it being possible to combine all substituents independently of one another. Preferred substituents in the benzene, pyridine, pyrazole, thiophene or (alkylsulfonyl)alkylamino moiety are alkyl, alkoxy, halogen, such as F, Cl, Br or I, amino, alkylamino, dialkylamino, acylamino, such as formylamino, nitro, alkoxycarbonyl, aminocarbonyl, alkylaminocarbonyl, dialkylaminocarbonyl, alkoxyaminocarbonyl, haloalkoxy, haloalkyl, alkylcarbonyl, alkoxyalkyl, alkylsulfonylaminoalkyl, (alkanesulfonyl)alkylamino. Such suitable sulfonylureas are, for example, A1) phenyl- and benzylsulfonylureas and related compounds, for example 1-(2-chlorophenylsulfonyl)-3-(4-methoxy-6-methyl-1,3,5-triazin-2-yl)urea (chlorsulfuron), 1-(2-ethoxycarbonylphenylsulfonyl)-3-(4-chloro-6-methoxypyrimidin-2-yl)urea (chlorimuron-ethyl), 1-(2-methoxyphenylsulfonyl)-3-(4-methoxy-6-methyl-1,3,5-triazin-2-yl)urea (metsulfuron-methyl), 1-(2-chloroethoxyphenylsulfonyl)-3-(4-methoxy-6-methyl-1,3,5-triazin-2-yl)urea (triasulfuron), 1-(2-methoxycarbonylphenysulfonyl)-3-(4,6-dimethylpyrimidin-2-yl)urea (sulfumeturon-methyl), 1-(2-methoxycarbonylphenylsulfonyl)-3-(4-methoxy-6-methyl-1,3,5-triazin-2-yl)-3-methylurea (tribenuron-methyl), 1-(2-methoxycarbonylbenzylsulfonyl)-3-(4,6-dimethoxypyrimidin-2-yl)urea (bensulfuron-methyl), 1-(2-methoxycarbonylphenylsulfonyl)-3-(4,6-bis(difluoromethoxy)pyrimidin-2-yl)urea (primisulfuron-methyl), 3-(4-ethyl-6-methoxy-1,3,5-triazin-2-yl)-1-(2,3-dihydro-1,1-dioxo-2-methylbenzo-[b]thiophene-7-sulfonyl)urea (EP-A 0 796 83), 3-(4-ethoxy-6-ethyl-1,3,5-triazin-2-yl)-1-(2,3-dihydro-1,1-dioxo-2-methylbenzo[b]-thiophene-7-sulfonyl)urea (EP-A 0 079 683), 3-(4-methoxy-6-methyl-1,3,5-triazin-2-yl)-1-(2-methoxycarbonyl-5-iodophenylsulfonyl)urea (iodosulfuron-methyl and its salts, such as the sodium salt, WO 92/13845), DPX-66037, triflusulfuron-methyl (see Brighton Crop Prot. Conf.—Weeds—1995, p. 853), CGA-277476, (see Brighton Crop Prot. Conf.-Weeds-1995, p. 79), methyl 2-[3-(4,6-dimethoxypyrimidin-2-yl)ureidosulfonyl]4-methanesulfonamidomethylbenzoate (mesosulfuron-methyl and its salts, such as the sodium salt, WO 95/10507), N,N-dimethyl-2-[3-(4,6-dimethoxypyrimidin-2-yl)ureidosulfonyl]-4-formylaminobenzamide (foramsulfuron and its salts, such as the sodium salt, WO 95/01344);

A2) thienylsulfonylureas, for example
1-(2-methoxycarbonylthiophen-3-yl)-3-(4-methoxy-6-methyl-1,3,5-triazin-2-yl)urea (thifensulfuron-methyl);
A3) pyrazolylsulfonylureas, for example
1-(4-ethoxycarbonyl-1-methylpyrazol-5-ylsulfonyl)-3-(4,6-dimethoxypyrimidin-2-yl)urea (pyrazosulfuron-methyl);
methyl 3-chloro-5-(4,6-dimethoxypyrimidin-2-ylcarbamoylsulfamoyl)-1-methylpyrazole-4-carboxylate (EP-A 0 282 613);
methyl 5-(4,6-dimethylpyrimidin-2-ylcarbamoylsulfamoyl)-1-(2-pyridyl)pyrazole-4-carboxylate (NC-330, see Brighton Crop Prot. Conference 'Weeds' 1991, Vol. 1, p. 45 ff.),
DPX-A8947, azimsulfuron, (see Brighton Crop Prot. Conf. 'Weeds' 1995, p. 65);
A4) sulfonediamide derivatives, for example
3-(4,6-dimethoxypyrimidin-2-yl)-1-(N-methyl-N-methylsulfonylaminosulfonyl)urea (amidosulfuron) and its structural analogs (EP-A 0 131 258 and Z. Pfl. Krankh. Pfl. Schutz,.special issue XII, 489-497 (1990));
A5) pyridylsulfonylureas, for example
1-(3-N,N-dimethylaminocarbonylpyridin-2-ylsulfonyl)-3-(4,6-dimethoxypyrimidin-2-yl)urea (nicosulfuron),
1-(3-ethylsulfonylpyridin-2-ylsulfonyl)-3-(4,6-dimethoxypyrimidin-2-yl)urea (rimsulfuron),
methyl 2-[3-(4,6-dimethoxypyrimidin-2-yl)ureidosulfonyl]-6-trifluoromethyl-3-pyridinecarboxylate, sodium salt (DPX-KE 459, flupyrsulfuron, see Brighton Crop Prot. Conf. Weeds, 1995, p. 49),
pyridylsulfonylureas as described, for example, in DE-A 40 00 503 and DE-A 40 30 577, preferably those of the formula

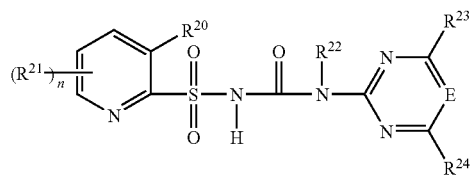

in which
E is CH or N, preferably CH,
$R^{20}$ is iodine or $NR^{25}R^{26}$,
$R^{21}$ is hydrogen, halogen, cyano, $(C_1-C_3)$-alkyl, $(C_1-C_3)$-alkoxy, $(C_1-C_3)$-haloalkyl, $(C_1-C_3)$-haloalkoxy, $(C_1-C_3)$-alkylthio, $(C_1-C_3)$-alkoxy-$(C_1-C_3)$-alkyl, $(C_1-C_3)$-alkoxycarbonyl, mono- or di-$((C_1-C_3)$-alkyl)amino, $(C_1-C_3)$-alkylsulfinyl or -sulfonyl, $SO_2$-$NR^xR^y$ or CO—$NR^xR^y$, in particular hydrogen,
$R^x$, $R^y$ independently of one another are hydrogen, $(C_1-C_3)$-alkyl, $(C_1-C_3)$-alkenyl, $(C_1-C_3)$-alkynyl or together are —$(CH_2)_4$—, —$(CH_2)_5$— or —$(CH_2)_2$-O—$(CH_2)_2$—,
n is 0, 1, 2 or 3, preferably 0 or 1,
$R^{22}$ is hydrogen or $CH_3$,
$R^{23}$ is halogen, $(C_1-C_2)$-alkyl, $(C_1-C_2)$-alkoxy, $(C_1-C_2)$-haloalkyl, in particular $CF_3$, $(C_1-C_2)$-haloalkoxy, preferably $OCHF_2$ or $OCH_2CF_3$,
$R^{24}$ is $(C_1-C_2)$-alkyl, $(C_1-C_2)$-haloalkoxy, preferably $OCHF_2$, or $(C_1-C_2)$-alkoxy,
$R^{25}$ is $(C_1-C_4)$-alkyl,
$R^{26}$ is $(C_1-C_4)$-alkylsulfonyl or
$R^{25}$ and $R^{26}$ together are a chain of the formula —$(CH_2)_3$SO_2$— or —$(CH_2)_4SO_2$—, for example 3-(4,6-dimethoxypyrimidin-2-yl)-1-(3-N-methylsulfonyl-N-methylaminopyridin-2-yl)sulfonylurea, or salts thereof;

A6) alkoxyphenoxysulfonylureas as described, for example, in EP-A 0 342 569, preferably those of the formula

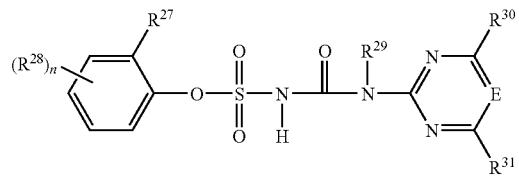

in which
E is CH or N, preferably CH,
$R^{27}$ is ethoxy, propoxy or isopropoxy,
$R^{28}$ is halogen, $NO_2$, $CF_3$, CN, $(C_1-C_4)$-alkyl, $(C_1-C_4)$-alkoxy, $(C_1-C_4)$-alkylthio or $(C_1-C_3)$-alkoxy-carbonyl, preferably in the 6-position on the phenyl ring,
n is 0, 1, 2 or 3, preferably 0 or 1,
$R^{29}$ is hydrogen, $(C_1-C_4)$-alkyl or $(C_3-C_4)$-alkenyl,
$R^{30}$, $R^{31}$ independently of one another are halogen, $(C_1-C_2)$-alkyl, $(C_1-C_2)$-alkoxy, $(C_1-C_2)$-haloalkyl, $(C_1-C_2)$-haloalkoxy or $(C_1-C_2)$-alkoxy-$(C_1-C_2)$-alkyl, preferably $OCH_3$ or $CH_3$, for example 3-(4,6-dimethoxypyrimidin-2-yl)-1-(2-ethoxyphenoxy)sulfonylurea or salts thereof;
A7) imidazolylsulfonylureas, for example
MON 37500, sulfosulfuron (see Brighton Crop Prot. Conf. 'Weeds', 1995, p. 57), and other related sulfonylurea derivatives and mixtures thereof.

Typical representatives of these active compounds are, inter alia, the compounds listed below: amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfuron, flupyrsulfuron-methyl-sodium, halosulfuron-methyl, imazosulfuron, metsulfuron-methyl, nicosulfuron, oxasulfuron, primisulfuron-methyl, prosulfuron, pyrazosulfuron-ethyl, rimsulfuron, sulfometuron-methyl, sulfosulfuron, thifensulfuron-methyl, triasulfuron, tribenuron-methyl, triflusulfuron-methyl, iodosulfuron-methyl and its sodium salt (WO 92/13845), mesosulfuron-methyl and its sodium salt (Agrow No. 347, Mar. 3, 2000, page 22 (PJB Publications Ltd. 2000)) and foramsulfuron and its sodium salt (Agrow No. 338, Oct. 15, 1999, page 26 (PJB Publications Ltd. 1999)).

The active compounds listed above are known, for example from "The Pesticide Manual", 13th edition (2003), The British Crop Protection Council, or from the literature references following the individual active compounds.

Other suitable ALS inhibitors are, for example,
B) imidazolinones, for example
methyl 2-(4-isopropyl-4-methyl-5-oxo-2-imidazolin-2-yl)-5-methylbenzoate and 2-(4-isopropyl-4-methyl-5-oxo-2-imidazolin-2-yl)-4-methylbenzoic acid (imazamethabenz),
5-ethyl-2-(4-isopropyl-4-methyl-5-oxo-2-imidazolin-2-yl) pyridine-3-carboxylic acid (imazethapyr),
2-(4-isopropyl-4-methyl-5-oxo-2-imidazolin-2-yl)quinoline-3-carboxylic acid (imazaquin),
2-(4-isopropyl-4-methyl-5-oxo-2-imidazolin-2-yl)pyridine-3-carboxylic acid (imazapyr),
5-methyl-2-(4-isopropyl-4-methyl-5-oxo-2-imidazolin-2-yl)pyridine-3-carboxylic acid (imazamethapyr);
C) triazolopyrimidinesulfonamides, for example
N-(2,6-difluorophenyl)-7-methyl-1,2,4-triazolo[1,5-c]pyrimidine-2-sulfonamide (flumetsulam),
N-(2,6-dichloro-3-methylphenyl)-5,7-dimethoxy-1,2,4-triazolo[1,5-c]pyrimidine-2-sulfonamide,
N-(2,6-difluorophenyl)-7-fluoro-5-methoxy-1,2,4-triazolo[1,5-c]pyrimidine-2-sulfonamide, N-(2,6-dichloro-3-methylphenyl)-7-chloro-5-methoxy-1,2,4-triazolo[1,5-c]pyrimidine-2-sulfonamide, N-(2-chloro-6-methoxycarbonyl)-5,7-dimethyl-1,2,4-triazolo[1,5-c]pyrimidine-2-sulfonamide (EP-A 0 343 752, U.S. Pat. No. 4,988,812);

D) pyrimidinyloxypyridinecarboxylic acid or pyrimidinyloxybenzoic acid derivatives, for example benzyl 3-(4,6-dimethoxypyrimidin-2-yl)oxypyridine-2-carboxylate (EP-A 0 249 707), methyl 3-(4,6-dimethoxypyrimidin-2-yl)oxypyridine-2-carboxylate (EP-A 0 249 707), 2,6-bis[(4,6-dimethoxypyrimidin-2-yl)oxy]benzoic acid (EP-A 0 321 846), 1-(ethoxycarbonyloxyethyl) 2,6-bis[(4,6-dimethoxypyrimidin-2-yl)oxy]benzoate (EP-A 0 472 113).

Suitable sulfonamides are preferably sulfonamides of the formula (I) and/or salts thereof

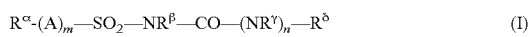

in which $R^\alpha$ is a hydrocarbon radical, preferably an aryl radical, such as phenyl, which is unsubstituted or substituted, or a heterocyclic radical, preferably a heteroaryl radical, such as pyridyl, which is unsubstituted or substituted, where the radicals including substituents have 1-30 carbon atoms, preferably 1-20 carbon atoms, or $R^\alpha$ is an electron-withdrawing group, such as a sulfonamide radical, $R^\beta$ is a hydrogen atom or a hydrocarbon radical which is unsubstituted or substituted and, including substituents, has 1-10 carbon atoms, for example unsubstituted or substituted $C_1$-$C_6$-alkyl, preferably a hydrogen atom or methyl, $R^\gamma$ is a hydrogen atom or a hydrocarbon radical which is unsubstituted or substituted and, including substituents, has 1-10 carbon atoms, for example unsubstituted or substituted $C_1$-$C_6$-alkyl, preferably a hydrogen atom or methyl, A is $CH_2$, O or NH, preferably O, m is zero or 1, n is zero or 1, preferably 1, and $R^\delta$ is a heterocyclic radical, such as a pyridyl radical, a triazinyl radical or a triazolinone radical.

Examples of sulfonamides of the formula (I) are sulfonylureas of the formula (II) and/or salts thereof

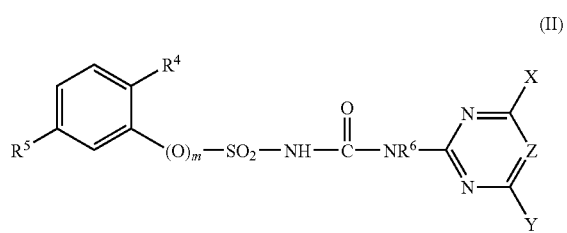

in which $R^4$ is $C_1$-$C_4$-alkoxy, preferably $C_2$-$C_4$-alkoxy, or CO—$R^a$, where $R^a$ is OH, $C_1$-$C_4$-alkoxy or $NR^bR^c$, where $R^b$ and $R^c$ independently of one another are identical or different radicals H or $C_1$-$C_4$-alkyl, $R^5$ is halogen, preferably iodine, or $(A)_n$-$NR^dR^e$, where n is zero or 1, A is a group CR'R", where R' and R" independently of one another are identical or different radicals H or $C_1$-$C_4$-alkyl, $R^d$ is H or $C_1$-$C_4$-alkyl and $R^e$ is an acyl radical, such as formyl or $C_1$-$C_4$-alkylsulfonyl, and, if $R^4$ is $C_1$-$C_4$-alkoxy, preferably $C_2$-$C_4$-alkoxy, $R^5$ may also be H, $R^6$ is H or $C_1$-$C_4$-alkyl, m is zero or 1, X and Y independently of one another are identical or different radicals $C_1$-$C_6$-alkyl, $C_1$-$C_6$-alkoxy or $C_1$-$C_6$-alkylthio, where each of the three radicals mentioned is unsubstituted or substituted by one or more radicals from the group consisting of halogen, $C_1$-$C_4$-alkoxy and $C_1$-$C_4$-alkylthio, or are $C_3$-$C_6$-cycloalkyl, $C_2$-$C_6$-alkenyl, $C_2$-$C_6$-alkynyl, $C_3$-$C_6$-alkenyloxy or $C_3$-$C_6$-alkynyloxy, preferably $C_1$-$C_4$-alkyl or $C_1$-$C_4$-alkoxy, and Z is CH or N.

Preference is given to sulfonylureas of the formula (II) and/or salts thereof in which a) $R^4$ is CO—($C_1$-$C_4$-alkoxy), $R^5$ is halogen, preferably iodine, or $R^5$ is $CH_2$—$NHR^e$, where $R^e$ is an acyl radical, preferably $C_1$-$C_4$-alkylsulfonyl, and m is zero, b) $R^4$ is CO—N($C_1$-$C_4$-alkyl)$_2$, $R^5$ is $NHR^e$, where $R^e$ is an acyl radical, preferably formyl, and m is zero, or c) $R^4$ is $C_2$-$C_4$-alkoxy, $R^5$ is H and m is 1.

Particularly preferred ALS inhibitors are: iodosulfuron-methyl (A1) and its sodium salt (A2), mesosulfuron-methyl (A3) and its sodium salt (A4), foramsulfuron (A5) and its sodium salt (A6), flucarbazone (A7) and its sodium salt (A8), propoxycarbazone (A9) and its sodium salt (A10), ethoxysulfuron (A11) and its sodium salt (A12), and amidosulfuron (A13) and its sodium salt (A14).

The active compounds listed above are known, for example from "The Pesticide Manual", 13th edition (2003), The British Crop Protection Council, or from the literature references given after the individual active compounds.

The liquid formulations according to the invention generally comprise the herbicidally active compounds from the group of the ALS inhibitors in amounts of from 0.01 to 50% by weight, preferably from 0.1 to 30% by weight; here and in the entire description, the term "% by weight" refers, unless defined otherwise, to the relative weight of the component in question based on the total weight of the formulation.

Whenever the term "acyl radical" is used in this description, this means the radical of an organic acid which is formally formed by removing an OH group from the organic acid, for example the radical of a carboxylic acid and radicals of acids derived therefrom, such as thiocarboxylic acid, unsubstituted or N-substituted iminocarboxylic acids or the radicals of carbonic monoesters, unsubstituted or N-substituted carbaminic acids, sulfonic acids, sulfinic acids, phosphonic acids, phosphinic acids.

An acyl radical is preferably formyl or acyl from the group consisting of CO—$R^z$, CS—$R^z$, CO—$OR^z$, CS—$OR^z$, CS—$SR^z$, $SOR^z$ and $SO_2R^z$, where $R^z$ is in each case a $C_1$-$C_{10}$-hydrocarbon radical, such as $C_1$-$C_{10}$-alkyl or $C_6$-$C_{10}$-aryl, which is unsubstituted or substituted, for example by one or more substituents from the group consisting of halogen, such as F, Cl, Br, I, alkoxy, haloalkoxy, hydroxyl, amino, nitro, cyano and alkylthio, or $R^z$ is aminocarbonyl or aminosulfonyl, where the two lastmentioned radicals are unsubstituted, N-monosubstituted or N,N-disubstituted, for example by substituents from the group consisting of alkyl and aryl. Acyl is, for example, formyl, haloalkylcarbonyl, alkylcarbonyl, such as ($C_1$-$C_4$)-alkyl-carbonyl, phenylcarbonyl, where the phenyl ring may be substituted, or alkyloxy-carbonyl, such as ($C_1$-$C_4$)-alkyloxycarbonyl, phenyloxycarbonyl, benzyloxycarbonyl, alkylsulfonyl, such as ($C_1$-$C_4$)-alkylsulfonyl, alkylsulfinyl, such as $C_1$-$C_4$-(alkylsulfinyl), N-alkyl-1-iminoalkyl, such as N—($C_1$-$C_4$)-1-imino-($C_1$-$C_4$)-alkyl, and other radicals of organic acids.

A hydrocarbon radical is a straight-chain, branched or cyclic and saturated or unsaturated aliphatic or aromatic hydrocarbon radical, for example alkyl, alkenyl, alkynyl, cycloalkyl, cycloalkenyl or aryl.

A hydrocarbon radical has preferably 1 to 40 carbon atoms, with preference 1 to 30 carbon atoms; with particular preference, a hydrocarbon radical is alkyl, alkenyl or alkynyl having up to 12 carbon atoms or cycloalkyl having 3, 4, 5, 6 or 7 ring atoms or phenyl.

An aromatic radical (aryl) is a mono-, bi- or polycyclic aromatic system, for example phenyl, naphthyl, tetrahydronaphthyl, indenyl, indanyl, pentalenyl, fluorenyl and the like, preferably phenyl.

A heterocyclic radical or ring (heterocyclyl) can be saturated, unsaturated or heteroaromatic and unsubstituted or substituted; it preferably contains one or more heteroatoms in the ring, preferably from the group consisting of N, O and S; it is preferably an aliphatic heterocyclyl radical having 3 to 7 ring atoms or a heteroaromatic radical having 5 or 6 ring atoms and contains 1, 2 or 3 heteroatoms. The heterocyclic radical can, for example, be a heteroaromatic radical or ring (heteroaryl), such as, for example, a mono-, bi- or polycyclic aromatic system in which at least one ring contains one or more heteroatoms, for example pyridyl, pyrimidinyl, pyridazinyl, pyrazinyl, triazinyl, thienyl, thiazolyl, oxazolyl, furyl, pyrrolyl, pyrazolyl and imidazolyl, or it is a partially or fully hydrogenated radical, such as oxiranyl, oxetanyl, pyrrolidyl, piperidyl, piperazinyl, triazolyl, dioxolanyl, morpholinyl, tetrahydrofuryl. Preference is given to pyrimidinyl and triazinyl. Suitable substituents for a substituted heterocyclic radical are the substituents mentioned further below, and additionally also oxo, for example in the triazolinone moiety. The oxo group may also be present at the hetero ring atoms, which may exist in different oxidation states, for example in the case of N and S.

Substituted radicals, such as substituted hydrocarbon radicals, for example substituted alkyl, alkenyl, alkynyl, aryl, phenyl and benzyl, or substituted heterocyclyl or heteroaryl, are, for example, a substituted radical which is derived from an unsubstituted parent compound, where the substituents are, for example, one or more, preferably 1, 2 or 3, radicals from the group consisting of halogen, alkoxy, haloalkoxy, alkylthio, hydroxyl, amino, nitro, carboxyl, cyano, azido, alkoxycarbonyl, alkylcarbonyl, formyl, carbamoyl, mono- and dialkylaminocarbonyl, substituted amino, such as acylamino, mono- and dialkylamino, and alkylsulfinyl, haloalkylsulfinyl, alkylsulfonyl, haloalkylsulfonyl and, in the case of cyclic radicals, also alkyl and haloalkyl, and unsaturated aliphatic radicals which correspond to the saturated hydrocarbon-containing radicals mentioned, such as alkenyl, alkynyl, alkenyloxy, alkynyloxy, etc. Among the radicals with carbon atoms, preference is given to those having 1 to 4 carbon atoms, in particular 1 or 2 carbon atoms. Preference is generally given to substituents from the group consisting of halogen, for example fluorine and chlorine, ($C_1$-$C_4$)-alkyl, preferably methyl or ethyl, ($C_1$-$C_4$)-haloalkyl, preferably trifluoromethyl, ($C_1$-$C_4$)-alkoxy, preferably methoxy or ethoxy, ($C_1$-$C_4$)-haloalkoxy, nitro and cyano. Particular preference is given here to the substituents methyl, methoxy and chlorine.

Unsubstituted or substituted phenyl is preferably phenyl which is unsubstituted or mono- or polysubstituted, preferably substituted up to three times, by identical or different radicals, preferably from the group consisting of halogen, ($C_1$-$C_4$-alkyl, ($C_1$-$C_4$)-alkoxy, ($C_1$-$C_4$)-haloalkyl, ($C_1$-$C_4$)-haloalkoxy and nitro, for example o-, m- and p-tolyl, dimethylphenyl, 2-, 3- and 4-chlorophenyl, 2-, 3- and 4-trifluoro- and -trichlorophenyl, 2,4-, 3,5-, 2,5- and 2,3-dichlorophenyl, o-, m- and p-methoxyphenyl.

Cycloalkyl is a carbocyclic saturated ring system having preferably 3-6 carbon atoms, for example cyclopropyl, cyclobutyl, cyclopentyl or cyclohexyl.

The carbon skeleton of the carbon-containing radicals, such as alkyl, alkoxy, haloalkyl, haloalkoxy, alkylamino and alkylthio and the corresponding unsaturated and/or substituted radicals may in each case be straight-chain or branched. In these radicals, preference is given to the lower carbon skeletons having, for example, 1 to 6 carbon atoms and, in the case of unsaturated groups, 2 to 6 carbon atoms, unless specified otherwise. Alkyl radicals, also in the composite meanings such as alkoxy, haloalkyl, etc., are, for example, methyl, ethyl, n- or isopropyl, n-, iso-, t- or 2-butyl, pentyls, hexyls, such as n-hexyl, isohexyl and 1,3-dimethylbutyl, heptyls, such as n-heptyl, 1-methylhexyl and 1,4-dimethylpentyl; alkenyl and alkynyl radicals have the meaning of the possible unsaturated radicals which correspond to the alkyl radicals; alkenyl is, for example, allyl, 1-methylprop-2-en-1-yl, 2-methyl-prop-2-en-1-yl, but-2-en-1-yl, but-3-en-1-yl, 1-methyl-but-3-en-1-yl and 1-methylbut-2-en-1-yl; alkynyl is, for example, propargyl, but-2-yn-1-yl, but-3-yn-1-yl, 1-methyl-but-3-yn-1-yl.

Halogen is, for example, fluorine, chlorine, bromine or iodine. Haloalkyl, -alkenyl and -alkynyl are alkyl, alkenyl and alkynyl, respectively, which are partially or fully substituted by halogen, preferably by fluorine, chlorine and/or bromine, in particular by fluorine or chlorine, for example $CF_3$, $CHF_2$, $CH_2F$, $CF_3CF_2$, $CH_2FCHCl$, $CCl_3$, $CHCl_2$, $CH_2CH_2Cl$; haloalkoxy is, for example, $OCF_3$, $OCHF_2$, $OCH_2F$, $CF_3CF_2O$, $OCH_2CF_3$ and $OCH_2CH_2Cl$; this applies correspondingly to haloalkenyl and other halogen-substituted radicals.

If, in the context of this description, the short form of the "common name" of an active compound is used, this embraces in each case all customary derivatives, such as esters and salts, and isomers, in particular optical isomers, especially the commercially available form or forms. If the "common name" refers to an ester or a salt, this embraces in each case also all other customary derivatives, such as other esters and salts, the free acids and neutral compounds, and isomers, in particular optical isomers, especially in the commercially available form or forms. The given chemical compound names refer to at least one of the compounds embraced by the "common name", frequently to a preferred compound.

For the purpose of the present invention, the ALS inhibitors contained in the liquid formulations according to the invention as component a) are to be understood as including, in addition to the neutral compounds, in particular in each case also their salts with inorganic and/or organic counterions. Thus, for example, sulfonamides are capable of forming salts in which the hydrogen of the —$SO_2$—NH— group is replaced by an agriculturally suitable cation. These salts are, for example, metal salts, in particular alkali metal salts or alkaline earth metal salts, in particular sodium salts and potassium salts, or else ammonium salts or salts with organic amines. Salts can also be formed by forming an adduct of an acid with basic groups, such as, for example, amino and alkylamino. Acids suitable for this purpose are strong inorganic and organic acids, for example HCl, HBr, $H_2SO_4$ or $HNO_3$.

Suitable agrochemically active compounds d), which may be present or not, are, for example, agrochemically active compounds different from component a), such as herbicides, fungicides, insecticides, plant growth regulators, safeners and the like. The agrochemically active compounds d) can be present in the organic solvent in suspended and/or dissolved form.

Suitable active compounds different from component a), which active compounds may be present in the liquid formulations according to the invention as component d), are, preferably, herbicidally active compounds, for example from the group of the carbamates, thiocarbamates, haloacetanilides, substituted phenoxy-, naphthoxy- and phenoxyphenoxycarboxylic acid derivatives, and also heteroaryloxyphenoxyalkanecarboxylic acid derivatives, such as quinolyloxy-, quinoxalyloxy-, pyridyloxy-, benzoxazolyloxy- and benzothiazolyloxyphenoxyalkanecarboxylic acid esters, cyclohexanedione derivatives, phosphorus-containing herbicides, for example of the glufosinate type or of the glyphosate type, and also S-(N-aryl-N-alkylcarbamoylmethyl)dithiophosphoric acid esters. Preference is given here to phenoxyphenoxy- and heteroaryloxyphenoxycarboxylic acid esters and salts, such as fenoxaprop, and also to herbicides such as bentazone, cyanazine, atrazine, diflufenican, dicamba, 2,4-D or hydroxybenzonitriles, such as bromoxynil and ioxynil, and other foliar herbicides, for example:

E) herbicides of the type of the phenoxyphenoxy- and heteroaryloxyphenoxycarboxylic acid derivatives, such as E1) phenoxyphenoxy- and benzyloxyphenoxycarboxylic acid derivatives, for example methyl 2-(4-(2,4-dichlorophenoxy)phenoxy)propionate (diclofop-methyl),
methyl 2-(4-(4-bromo-2-chlorophenoxy)phenoxy)propionate (DE-A 26 01 548),
methyl 2-(4-(4-bromo-2-fluorophenoxy)phenoxy)propionate (U.S. Pat. No. 4,808,750),
methyl 2-(4-(2-chloro-4-trifluoromethylphenoxy)phenoxy)propionate (DE-A 24 33 067),
methyl 2-(4-(2-fluoro-4-trifluoromethylphenoxy)phenoxy)propionate (U.S. Pat. No. 4,808,750),
methyl 2-(4-(2,4-dichlorobenzyl)phenoxy)propionate (DE-A 24 17 487),
ethyl 4-(4-(4-trifluoromethylphenoxy)phenoxy)pent-2-enoate,
methyl 2-(4-(4-trifluoromethylphenoxy)phenoxy)propionate (DE-A 24 33 067);

E2) "monocyclic" heteroaryloxyphenoxyalkanecarboxylic acid derivatives, for example
ethyl 2-(4-(3,5-dichloropyridyl-2-oxy)phenoxy)propionate (EP-A 0 002 925),
propargyl 2-(4-(3,5-dichloropyridyl-2-oxy)phenoxy)propionate (EP-A 0 003 114),
methyl 2-(4-(3-chloro-5-trifluoromethyl-2-pyridyloxy)phenoxy)propionate (EP-A 0 003 890),
ethyl 2-(4-(3-chloro-5-trifluoromethyl-2-pyridyloxy)phenoxy)propionate (EP-A 0 003 890),
propargyl 2-(4-(5-chloro-3-fluoro-2-pyridyloxy)phenoxy)propionate (EP-A 0 191 736),
butyl 2-(4-(5-trifluoromethyl-2-pyridyloxy)phenoxy)propionate (fluazifop-butyl);

E3) "bicyclic" heteroaryloxyphenoxyalkanecarboxylic acid derivatives, for example
methyl and ethyl 2-(4-(6-chloro-2-quinoxalyloxy)phenoxy)propionate (quizalofopmethyl and quizalofopethyl),
methyl 2-(4-(6-fluoro-2-quinoxalyloxy)phenoxy)propionate (see J. Pest. Sci. Vol. 10, 61 (1985)),
2-isopropylideneaminooxyethyl 2-(4-(6-chloro-2-quinoxalyloxy)phenoxy)propionate (propaquizafop),
ethyl 2-(4-(6-chlorobenzoxazol-2-yloxy)phenoxy)propionate (fenoxaprop-ethyl), its D(+) isomer (fenoxaprop-P-ethyl, EX) and ethyl 2-(4-(6-chlorobenzothiazol-2-yloxy)phenoxy)propionate (DE-A 26 40 730),
tetrahydro-2-furylmethyl 2-(4-(6-chloroquinoxalyloxy)phenoxy)propionate (EP-A 0 323 727);

F) chloroacetanilides, for example
N-methoxymethyl-2,6-diethylchloroacetanilide (alachlor),
N-(3-methoxyprop-2-yl)-2-methyl-6-ethylchloroacetanilide (metolachlor),
2,6-dimethyl-N-(3-methyl-1,2,4-oxadiazol-5-ylmethyl) chloroacetanilide,
N-(2,6-dimethylphenyl)-N-(1-pyrazolylmethyl)chloroacetamide (metazachlor);

G) thiocarbamates, for example
S-ethyl N,N-dipropylthiocarbamate (EPTC),
S-ethyl N,N-diisobutylthiocarbamate (butylate);

H) cyclohexanedione oximes, for example
methyl 3-(1-allyloxyiminobutyl)4-hydroxy-6-,6-dimethyl-2-oxocyclohex-3-ene-carboxylate (alloxydim),
2-(1-ethoxyiminobutyl)-5-(2-ethylthiopropyl)-3-hydroxycyclohex-2-ene-1-one (sethoxydim),
2-(1-ethoxyiminobutyl)-5-(2-phenylthiopropyl)-3-hydroxycyclohex-2-ene-1-one (cloproxydim),
2-(1-(3-chloroallyloxy)iminobutyl)-5-(2-ethylthiopropyl)-3-hydroxycyclohex-2-ene-1-one,
2-(1-(3-chloroallyloxy)iminopropyl)-5-(2-ethylthiopropyl)-3-hydroxycyclohex-2-ene-1-one (clethodim),
2-(1-ethoxyiminobutyl)-3-hydroxy-5-(thian-3-yl)cyclohex-2-enone (cycloxydim),
2-(1-ethoxyiminopropyl)-5-(2,4,6-trimethylphenyl)-3-hydroxycyclohex-2-ene-1-one (tralkoxydim);

I) benzoylcyclohexanediones, for example
2-(2-chloro-4-methylsulfonylbenzoyl)cyclohexane-1,3-dione (SC-0051, EP-A 0 137 963, sylcotrione), 2-(2-nitrobenzoyl)4,4-dimethylcyclohexane-1,3-dione (EP-A 0 274 634),
2-(2-nitro-4-methylsulfonylbenzoyl)4,4-dimethylcyclohexane-1,3-dione (WO 91/13548, mesotrione);

J) S-(N-aryl-N-alkylcarbamoylmethyl) dithiophosphonates, such as
S-[N-(4-chlorophenyl)-N-isopropylcarbamoylmethyl] O,O-dimethyl dithiophosphate (anilophos);

K) alkylazines, such as, for example, described in WO-A 97/08156,
WO-A-97/31904, DE-A-19826670, WO-A-98/15536, WO-A-8/15537,
WO-A-98/15538, WO-A-98/15539 and also DE-A-19828519, WO-A-98/34925,
WO-A-98/42684, WO-A-99/188100, WO-A-99/19309, WO-A-99/37627 and
WO-A-99/65882, preferably those of the formula (K)

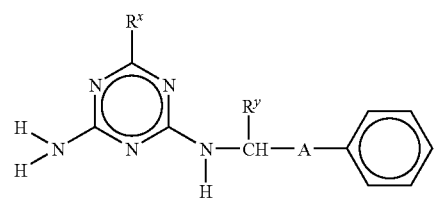

(K)

in which
$R^X$ is $(C_1-C_4)$-alkyl or $(C_1-C_4)$-haloalkyl;
$R^Y$ is $(C_1-C_4)$-alkyl, $(C_3-C_6)$-cycloalkyl or $(C_3-C_6)$-cycloalkyl-$(C_1-C_4)$-alkyl and
A is —$CH_2$—, —$CH_2$—$CH_2$—, —$CH_2$—$CH_2$—$CH_2$—, —O—, —$CH_2$—$CH_2$—O—, —$CH_2$—$CH_2$—$CH_2$—O—, particularly preferably those of the formulae K1-K7

(K1) 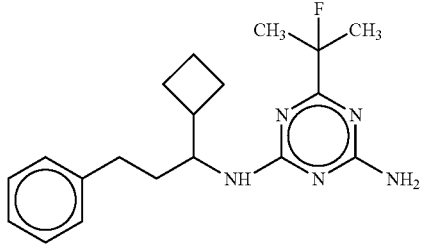

(K2) 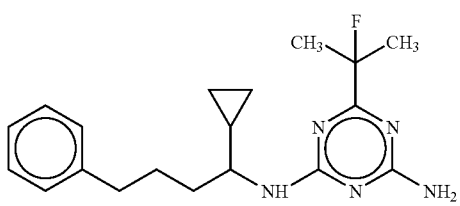

(K3) 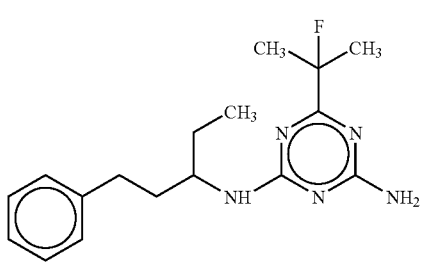

(K4) 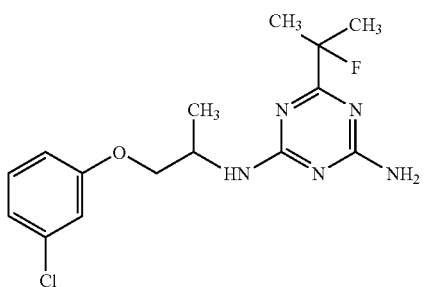

(K5) 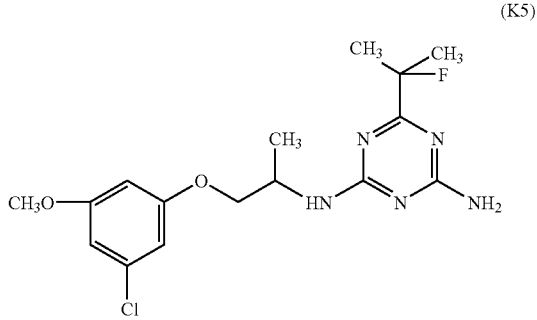

(K6) 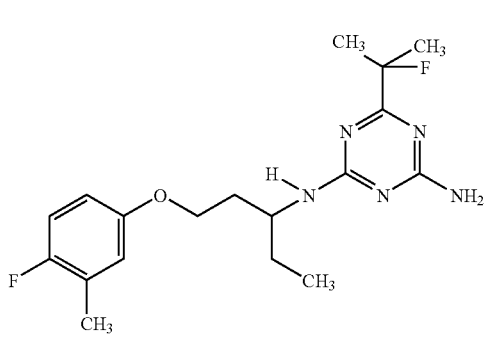

-continued (K7) 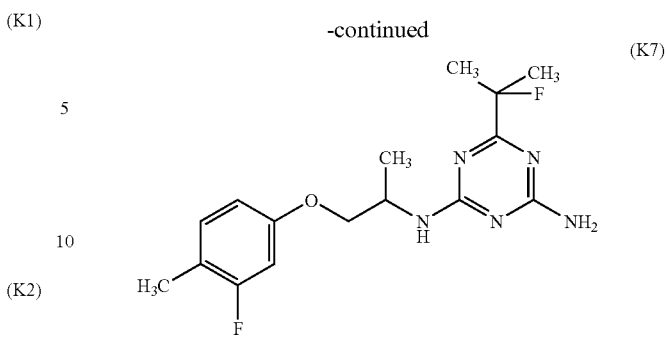

L) Phosphorus-containing herbicides, for example of the glusosinate type, such as glufosinate in a narrower sense, i.e. D,L-2-amino4-[hydroxy(methyl)phosphinyl]-butanoic acid, glufosinate monoammonium salt, L-glufosinate, L- or (2S)-2-amino-4-[hydroxy(methyl)phosphinyl]butanoic acid, L-glufosinate monoammonium salt or bialaphos (or bilanafos), i.e. L-2-amino4-[hydroxy(methyl)phosphinyl] butanoyl-L-alanyl-L-alanine, in particular its sodium salt, or of the glyphosate type, such as glyphosate, i.e. N-(phosphonomethyl)glycine, glyphosate monoisopropylammonium salt, glyphosate sodium salt or sulfosate, i.e. N-(phosphonomethyl)glycine trimesium salt=N-(phosphonomethyl)glycine trimethylsulfoxonium salt.

The herbicides of groups E to L are known, for example, from the abovementioned publications and from "The Pesticide Manual", 12th edition, 2000, The British Crop Protection Council, "Agricultural Chemicals Book II—Herbicides—", by W. T. Thompson, Thompson Publications, Fresno Calif., USA 1990 and "Farm Chemicals Handbook '90", Meister Publishing Company, Willoughby Ohio, USA, 1990.

The liquid formulations according to the invention may, as component d), also comprise safeners which are suitable for reducing or preventing damage to the crop plant. Suitable safeners are known, for example, from WO-A-96/14747 and the literature cited therein.

Suitable safeners are, for example, the following groups of compounds:

1) Compounds of the type of dichlorophenylpyrazoline-3-carboxylic acid (S1), preferably compounds such as ethyl 1-(2,4-dichlorophenyl)-5-(ethoxy-carbonyl)-5-methyl-2-pyrazoline-3-carboxylate (S1-1, mefenpyr-diethyl, PM pp. 781-782), and related compounds, as described in WO 91/07874.

2) Derivatives of dichlorophenylpyrazolecarboxylic acid, preferably compounds such as ethyl 1-(2,4-dichlorophenyl)-5-methylpyrazole-3-carboxylate (S1-2), ethyl 1-(2,4-dichlorophenyl)-5-isopropylpyrazole-3-carboxylate (S1-3), ethyl 1-(2,4-dichlorophenyl)-5-(1,1-dimethylethyl) pyrazole-3-carboxylate (S1-4), ethyl 1-(2,4-dichlorophenyl)-5-phenylpyrazole-3-carboxylate (S1-5) and related compounds, as described in EP-A-333 131 and EP-A-269 806.

3) Compounds of the type of the triazolecarboxylic acids (S1), preferably compounds such as fenchlorazole, i.e. ethyl 1-(2,4-dichlorophenyl5-trichloro-methyl-(1H)-1,2,4-triazole-3-carboxylate (S1-6), and related compounds (see EP-A-174 562 and EP-A-346 620).

4) Compounds of the type of the 5-benzyl- or 5-phenyl-2-isoxazoline-3-carboxylic acid, or the 5,5-diphenyl-2-isoxazoline-3-carboxylic acid, preferably compounds such as ethyl 5-(2,4-dichlorobenzyl)-2-isoxazoline-3-carboxylate (S1-7) or ethyl 5-phenyl-2-isoxazoline-3-carboxylate (S1-8) and related compounds, as described in WO 91/08202, or 5,5-diphenyl-2-isoxazolinecarboxylic acid and its ethyl ester (S1-9, isoxadifen-ethyl) or n-propyl ester (S1-10) or ethyl 5-(4-fluorophenyl)-5-phenyl-2-isoxazoline-3-carboxylate (S1-11), as described in the patent application (WO-A-95/07897).

5) Compounds of the type of the 8-quinolineoxyacetic acid (S2), preferably
   1-methylhex-1-yl (5-chloro-8-quinolineoxy)acetate (S2-1, cloquintocet-mexyl, PM pp. 263-264),
   1,3-dimethylbut-1-yl (5-chloro-8-quinolineoxy)acetate (S2-2),
   4-allyloxybutyl (5-chloro-8-quinolineoxy)acetate (S2-3),
   1-allyloxyprop-2-yl (5-chloro-8-quinolineoxy)acetate (S2-4),
   ethyl (5-chloro-8-quinolineoxy)acetate (S2-5),
   methyl (5-chloro-8-quinolineoxy)acetate (S2-6),
   allyl (5-chloro-8-quinolineoxy)acetate (S2-7),
   2-(2-propylideneiminooxy)-1-ethyl (5-chloro-8-quinolineoxy)acetate (S2-8),
   2-oxoprop-1-yl (5-chloro-8-quinolineoxy)acetate (S2-9)
   and related compounds, as described in EP-A-86 750, EP-A-94 349 and EP-A-191 736 or EP-A-0 492 366.

6) Compounds of the type of the (5-chloro-8-quinolineoxy) malonic acid, preferably compounds such as diethyl (5-chloro-8-quinolineoxy)malonate, diallyl (5-chloro-8-quinolineoxy)malonate, methyl ethyl (5-chloro-8-quinoline-oxy)malonate and related compounds, as described in EP-A-0 582 198.

7) Active compounds of the type of the phenoxyacetic or -propionic acid derivatives or the aromatic carboxylic acids, such as, for example,
   2,4-dichlorophenoxyacetic acid (esters) (2,4-D), 4-chloro-2-methylphenoxy-propionic esters (mecoprop), MCPA or 3,6-dichloro-2-methoxybenzoic acid (esters) (dicamba).

8) Active compounds of the type of the pyrimidines, such as "fenclorim" (PM, pp. 512-511) (=4,6-dichloro-2-phenylpyrimidine).

9) Active compounds of the type of the dichloroacetamides, which are frequently used as pre-emergence safeners (soil-acting safeners), such as, for example,
   "dichlormid" (PM, pp. 363-364 (=N,N-diallyl-2,2-dichloroacetamide),
   "R-29148" (=3-dichloroacetyl-2,2,5-trimethyl-1,3-oxazolidone from Stauffer),
   "benoxacor" (PM, pp. 102-103) (=4-dichloroacetyl-3,4-dihydro-3-methyl-2H-1,4-benzoxazine), p1 "PPG-1292" (=N-allyl-N-[(1,3-dioxolan-2-yl)methyl]dichloroacetamide from PPG Industries),
   "DK-24" (=N-allyl-N-[(allylaminocarbonyl)methyl] dichloroacetamide from Sagro-Chem),
   "AD-67" or "MON 4660" (=3-dichloroacetyl-1-oxa-3-azaspiro[4,5]decane from Nitrokemia or Monsanto),
   "dicyclonon" or "BAS145138" or "LAB145138" (=3-dichloroacetyl-2,5,5-tri-methyl-1,3-diazabicyclo[4.3.0]nonane from BASF) and
   "furilazol" or "MON 13900" (see PM, 637-638) (=(RS)-3-dichloroacetyl-5-(2-furyl)-2,2-dimethyloxazolidone).

10) Active compounds of the type of the dichloroacetone derivatives, such as, for example,
    "MG 191" (CAS-Reg. No. 96420-72-3) (=2-dichloromethyl-2-methyl-1,3-dioxolane from Nitrokemia).

11) Active compounds of the type of the oxyimino compounds, which are known as seed dressings, such as, for example,
    "oxabetrinil" (PM, pp. 902-903) (=(Z)-1,3-dioxolan-2-yl-methoxyimino-(phenyl)acetonitrile), which is known as seed dressing safener against metolachlor damage,
    "fluxofenim" (PM, pp. 613-614) (=1-(4-chlorophenyl)-2,2,2-trifluoro-1-ethanone O-(1,3-dioxolan-2-ylmethyl) oxime which is known as seed dressing safener against metolachlor damage, and
    "cyometrinil" or "CGA-43089" (PM, p. 1304) (=(Z)-cyanomethoxyimino-(phenyl)acetonitrile), which is known as seed dressing safener against metolachlor damage.

12) Active compounds of the type of the thiazolecarboxylic esters, which are known as seed dressings, such as, for example,
    "flurazole" (PM, pp. 590-591) (=benzyl 2-chloro4-trifluoromethyl-1,3-thiazole-5-carboxylate), which is known as seed dressing safener against alachlor and metolachlor damage.

13) Active compounds of the type of the naphthalenedicarboxylic acid derivatives, which are known as seed dressings, such as, for example,
    "naphthalic anhydride" (PM, p. 1342) (=1,8-naphthalenedicarboxylic anhydride), which is known as seed dressing safener for corn against thiocarbamate herbicide damage.

14) Active compounds of the type of the chromanacetic acid derivatives, such as, for example,
    "CL 304415" (CAS-Reg. No. 31541-57-8) (=2-84-carboxychroman4-yl)acetic acid from American Cyanamid).

15) Active compounds which, in addition to a herbicidal action against harmful plants, also have safener action on crop plants such as, for example,
    "dimepiperate" or "MY-93" (PM, pp. 404-405) (=S-1-methyl-1-phenylethyl piperidine-1-thiocarboxylate),
    "daimuron" or "SK 23" (PM,. p. 330) (=1-(1-methyl-1-phenylethyl)3-p-tolyl-urea),
    "cumyluron"="JC-940" (=3-(2-chlorophenylmethyl)-1-(1-methyl-1-phenyl-ethyl)urea, see JP-A-60087254),
    "methoxyphenone" or "NK 049" (=3,3'-dimethyl-4-methoxybenzophenone),
    "CSB" (=1-bromo4-(chloromethylsulfonyl)benzene) (CAS-Reg. No. 54091-06-4 from Kumiai),
    compounds of the type of the acylsulfamoylbenzamides, for example of formula (VIII) below, which are known, for example, from WO 99/16744.

(VIII)

| Compound No. | $R^{21}$ | $R^{22}$ |
|---|---|---|
| S3-1 | cyclopropyl | 2-OCH$_3$ |
| S3-2 | cyclopropyl | 2-OCH$_3$, 5-Cl |
| S3-3 | ethyl | 2-OCH$_3$ |
| S3-4 | isopropyl | 2-OCH$_3$, 5-Cl |
| S3-5 | isopropyl | 2-OCH$_3$ |

Preferred safeners are mefenpyr, fenchlorazole, isoxadifen, cloquintocet and their $C_1$-$C_{10}$-alkyl esters, and the safeners (S3-1), (S3-5) and benoxacor (S-4), in particular mefenpyr-diethyl (S1-1), fenchlorazole-ethyl (S1-6), isoxadifen-ethyl (S1-9), cloquintocet-mexyl (S2-1), (S3-1), (S3-5) and benoxacor (S-4).

If the liquid formulations according to the invention contain agrochemically active compounds d), their proportion by weight is generally from 0.1 to 60% by weight, in particular from 0.5 to 40% by weight. In the case of liquid active compounds d), their proportion by weight may also be higher, for example up to 80% by weight. The total content of active compounds in the liquid formulations according to the invention (sum of the components a)+d)) is generally between 1 and 80% by weight, in particular between 3 and 60% by weight.

Suitable organic solvents (component b) are, for example:
1) hydrocarbons (see, for example, Römpp Lexikon Chemie, 10th edition, volume 3, page 2202 (1997), Georg Thieme Verlag Stuttgart/New York), preferably those which are liquid under STP conditions. The hydrocarbons can be acyclic (aliphatic) hydrocarbons or cyclic hydrocarbons, for example aromatic or alicyclic (cycloaliphatic) hydrocarbons.

Examples of hydrocarbons b) are:
1a) aromatic hydrocarbons, for example
   aromatic hydrocarbons which are mono- or polysubstituted by alkyl (for example mono-, di- or trisubstituted by ($C_1$-$C_{10}$)-alkyl), for example benzenes, such as toluene, xylenes, mesitylene, ethylbenzene, or hydrocarbons having fused aromatic ring systems, such as naphthalenes, for example 1-methylnaphthalene, 2-methylnaphthalene or dimethylnaphthalene, or other fused aromatic hydrocarbons, such as indane or tetralin,
1b) cycloaliphatic hydrocarbons, for example
   saturated or unsaturated cycloaliphatic hydrocarbons which are optionally mono- or polysubstituted by alkyl (for example mono-, di- or trisubstituted by ($C_1$-$C_{10}$)-alkyl), such as cycloalkanes, cycloalkenes or cycloalkynes, for example cyclohexane or methylcyclopentane,
1c) aliphatic hydrocarbons, for example
   straight-chain or branched saturated or unsaturated aliphatic hydrocarbons, preferably $C_5$-$C_{16}$-aliphatic hydrocarbons, for example alkanes, alkenes or alkynes, such as pentane, hexane, octane, 2-methylbutane or 2,2,4-trimethylpentane.

The liquid formulations according to the invention may, as component b), also contain mixtures of one or more aromatic hydrocarbons and/or one or more cycloaliphatic hydrocarbons and/or one or more aliphatic hydrocarbons. Examples are mixtures of a plurality of aliphatic hydrocarbons, for example commercially available solvents of the Exxsol®D series, Isopar200 series or bayol® series, for example Bayol®82 (ExxonMobil Chemicals), or of the Isane®IP series or Hydroseal®G series (TotalFinaElf), or mixtures of aromatic and aliphatic hydrocarbons, for example commercially available solvents of the Solvesso® series, for example Solvesso®100, Solvesso®150 or Solvesso®200 (ExxonMobil Chemicals), of the Solvarex®/Solvaro® series (TotalFinaElf) or of the Caromax® series, for example Caromax®28 (Petrochem Carless).

2) Halogenated hydrocarbons, such as halogenated aromatic and aliphatic hydrocarbons, such as chlorobenzene or methylene chloride.
3) Polar solvents, for example aprotic polar solvents, such as ethers, esters of $C_1$-$C_9$-alkanoic acids which may be mono-, di- or polyfunctional, such as their mono-, di- or triesters, for example with $C_1$-$C_{18}$-alkyl alcohols, ketones having a low tendency to tautomerize, phophoric acid esters, amides, nitriles or sulfones, for example diisobutyl adipate, Rhodiasolv® RPDE (Rhodia), cyclohexanone, Jeffsol®PC (Huntsman), γ-butyrolactone, N-methylpyrrolidone, dimethyl sulfoxide, acetonitrile, tributylphosphatam or the Hostarex®PO series (Clariant), or protic polar solvents, such as alcohols, for example hexanol, heptanol, 2-ethylhexanol, glycerol, ethanolamine, fatty alcohols, such as the Agnique® FOH series (Clariant), or polyalkylene glycols, such as polyethylene glycols, for example from the Pluriol® E series or the Pluriol® AE series (BASF), carboxylic acids, for example acetic acid, adipic acid, or the Agnique® FAC series (Clariant), or amines, for example diethylamine or isobutylamine.

4) Fatty acid esters, for example of natural origin, for example natural oils, such as animal oils or vegetable oils, or of synthetic origin, for example the Edenor® series, for example Edenor® MEPa or Edenor® MESU, or the Agnique® ME series or Agnique® AE series (Cognis), the Salim® ME series (Salim), the Radia® series, for example Radia® 30167 (ICI), the Prilube® series, for example Prilube® 1530 (Petrofina), the Stepan® C series (Stepan) or the Witconol® 23 series (Witco). The fatty acid esters are preferably esters of $C_{10}$-$C_{22}$—, with preference $C_{12}$-$C_{20}$—, fatty acids. The $C_{10}$-$C_{22}$-fatty acid esters are, for example, esters of unsaturated or saturated $C_{10}$-$C_{22}$-fatty acids, in particular those having an even number of carbons, for example erucic acid, lauric acid, palmitic acid, and in particular $C_{18}$-fatty acids, such as stearic acid, oleic acid, linoleic acid or linolenic acid.

Examples of fatty acid esters such as $C_{10}$-$C_{22}$-fatty acid esters are glycerol and glycol esters of fatty acids such as $C_{10}$-$C_{22}$-fatty acids, or transesterification products thereof, for example fatty acid alkyl esters such as $C_{10}$-$C_{22}$-fatty acid $C_1$-$C_{20}$-alkyl esters, which can be obtained, for example, by transesterification of the abovementioned glycerol or glycol fatty acid esters such as $C_{10}$-$C_{22}$-fatty acid esters with $C_1$-$C_{20}$-alcohols (for example methanol, ethanol, propanol or butanol). The transesterification can be carried out by known methods, as described, for example, in Römpp Chemie Lexikon, 9th edition, volume 2, page 1343, Thieme Verlag Stuttgart.

Preferred fatty acid alkyl esters such as $C_{10}$-$C_{22}$-fatty acid $C_1$-$C_{20}$-alkyl esters are methyl esters, ethyl esters, propyl esters, butyl esters, 2-ethylhexyl esters and dodecyl esters. Preferred glycol and glycerol fatty acid esters such as $C_{10}$-$C_{22}$-fatty acid esters are the uniform or mixed glycol esters and glycerol esters of $C_{10}$-$C_{22}$-fatty acids, in particular of such fatty acids having an even number of carbon atoms, for example erucic acid, lauric acid, palmitic acid and in particular $C_{18}$-fatty acids such as stearic acid, oleic acid, linoleic acid or linolenic acid.

Animal oils b) are generally known and commercially available. For the purpose of the present invention, the term "animal oils" is to be understood as meaning, for example, oils of animal origin such as whale oil, cod-liver oil, musk oil or mink oil.

Vegetable oils b) are generally known and commercially available. For the purpose of the present invention, the term "vegetable oils" is to be understood as meaning, for example, oils of oleaginous plant species, such as soybean oil, rapeseed oil, corn oil, sunflower oil, cottonseed oil, linseed oil, coconut oil, palm oil, thistle oil, walnut oil, arachis oil, olive oil or castor oil, in particular rapeseed oil, where the vegetable oils also include their transesterification products, for example alkyl esters, such as rapeseed oil methyl ester or rapeseed oil ethyl ester.

The vegetable oils are preferably esters of $C_{10}$-$C_{22}$—, preferably $C_{12}$-$C_{20}$—, fatty acids. The $C_{10}$-$C_{22}$-fatty acid esters are, for example, esters of unsaturated or saturated $C_{10}$-$C_{22}$-fatty acids having, in particular, an even number of carbon atoms, for example erucic acid, lauric acid, palmitic acid and in particular $C_{18}$-fatty acids such as stearic acid, oleic acid, linoleic acid or linolenic acid.

Examples of vegetable oils are $C_{10}$-$C_{22}$-fatty acid esters of glycerol or glycol with $C_{10}$-$C_{22}$-fatty acids, or $C_{10}$-$C_{22}$-fatty acid $C_1$-$C_{20}$-alkyl esters which can be obtained, for example, by transesterification of the glycerol or glycol $C_{10}$-$C_{22}$-fatty acid esters mentioned above with $C_1$-$C_{20}$-alcohols (for example methanol, ethanol, propanol or butanol). The transesterification can be carried out by known methods as described, for example, in Römpp Chemie Lexikon, 9th edition, volume 2, page 1343, Thieme Verlag Stuttgart.

The vegetable oils can be contained in the liquid formulations according to the invention for example in the form of commercially available vegetable oils, in particular rapeseed oils, such as rapeseed oil methyl ester, for example Phytorob® B (Novance, France), Edenor® MESU and the Agnique® ME series (Cognis, Germany), the Radia® series (ICI), the Prilube® series (Petrofina), or biodiesel or in the form of commercially available, plant-oil-containing solvents, in particular those based on rapeseed oils, such as rapeseed oil methyl esters, for example Hasten® (Victorian Chemical Company, Australia, hereinbelow referred to as Hasten, main ingredient: rapeseed oil ethyl ester), Actirob® B (Novance, France, hereinbelow referred to as ActirobB, main ingredient: rapeseed oil methyl ester), Rako-Binol® (Bayer AG, Germany, hereinbelow referred to as Rako-Binol, main ingredient: rapeseed oil), Renol® (Stefes, Germany, hereinbelow referred to as Renol, vegetable oil ingredient: rapeseed oil methyl ester) or Stefes Mero® (Stefes, Germany, hereinbelow referred to as Mero, main ingredient: rapeseed oil methyl ester).

Examples of synthetic fatty acid esters are, for example, those derived from fatty acids having an odd number of carbon atoms, such as $C_{11}$-$C_{21}$-fatty acid esters.

Preferred organic solvents are hydrocarbons, in particular aromatic hydrocarbons and/or aliphatic hydrocarbons and fatty acid esters, such as vegetable oils, such as triglycerides of fatty acids having 10 to 22 carbon atoms, which may be saturated or else unsaturated, linear or branched and which may or may not carry further functional groups, such as corn oil, rapeseed oil, sunflower oil, cottonseed oil, linseed oil, soybean oil, coconut oil, palm oil, thistle oil or castor oil, and their transesterification products, such as fatty acid alkyl esters, and mixtures thereof.

The total proportion of organic solvents b) in the liquid formulations according to the invention is generally between 5 and 95% by weight, preferably in the range between 20 and 90% by weight. If liquid active compounds d) are used, the total proportion of solvents may also be below 5% by weight.

The inorganic salts c) contained in the liquid formulations according to the invention are preferably basic inorganic salts. These are to be understood as meaning salts which, in a 1% strength aqueous solution, have a pH>7, preferably weakly basic salts havig a pH between 7 and 11. Examples of such salts c) are salts which are not used as fertilizers, in particular salts which are different from sulfates, hydrogensulfates, phosphates, hydrogenphosphates and nitrates. Preferred salts c) are carbonates, bicarbonates, hydroxides, oxides, hypochlorites and sulfites, preferably carbonates and bicarbonates. As cations, the salts c) preferably contain metal ions, in particular alkali metal, alkaline earth metal and transition metal ions, preferably alkali metal and alkaline earth metal ions, such as sodium, potassium, magnesium or calcium. Thus, particularly preferred salts c) are alkali metal carbonates, bicarbonates, hydroxides, oxides, hypochlorites and sulfites, alkaline earth metal carbonates, bicarbonates, hydroxides, oxides, hypochlorites and sulfites, and transition metal carbonates, bicarbonates, hydroxides, oxides, hypochlorites and sulfites. Very particular preference is given to alkali metal salts, in particular alkali metal carbonates and alkali metal bicarbonates, such as $Na_2CO_3$, $K_2CO_3$, $NaHCO_3$ and $KHCO_3$. The inorganic salts c) may be present on their own or in a mixture.

The total proportion of component c) in the liquid formulations according to the invention is generally between 0.01 and 20% by weight, preferably in a range between 0.01 and 10% by weight, particularly preferably in a range between 0.05 and 5% by weight.

The sulfosuccinates (component e) optionally present in the liquid formulations according to the invention can, for example, be mono- or diesters of sulfosuccinic acid, preferably those of the formula (III)

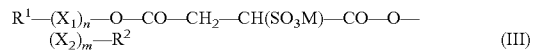
(III)

in which
$R^1$ is H or an unsubstituted or substituted $C_1$-$C_{30}$-hydrocarbon radical, such as $C_1$-$C_{30}$-alkyl or $C_7$-$C_{30}$-alkylaryl,
$R^2$ is H or an unsubstituted or substituted $C_1$-$C_{30}$-hydrocarbon radical, such as $C_1$-$C_{30}$-alkyl or $C_7$-$C_{30}$-alkylaryl, or a cation, for example a metal cation, such as an alkali metal or alkaline earth metal cation, or an ammonium cation, such as $NH_4$ or an alkyl-, alkylaryl- or poly(arylalkyl)-phenylammonium cation,
$X^1$, $X^2$ are identical or different and independently of one another are a spacer unit, such as a polyether unit or a polyester unit,
n,m are identical or different and independently of one another are zero or 1, preferably zero, and
M is a cation, for example a metal cation, such as an alkali metal or alkaline earth metal cation, or an ammonium cation, such as $NH_4$ or an alkyl-, alkylaryl- or poly(arylalkyl)phenylammonium cation.

Preference is given to sulfosuccinates of the formula (III) in which $R^1$ and $R^2$ are identical or different and independently of one another are linear, branched or cyclic, saturated or unsaturated $C_1$-$C_{20}$—, preferably $C_4$-$C_{18}$—, alkyl radicals, such as methyl, ethyl, butyl, hexyl, cyclohexyl, octyl, such as 2-ethylhexyl, decyl, tridecyl or octadecyl radicals, or $R^1$ and $R^2$ are $C_7$-$C_{20}$-alkylaryl radicals, such as nonylphenyl, 2,4,6-tri-sec-butylphenyl, 2,4,6-tris-(1-phenylethyl)phenyl, alkylbenzyl or a hydrocinnamic radical,
$X_1$ and $X_2$ are identical or different and independently of one another are polyether units, such as polyethylene glycols —$(C_2H_4O)_p$— or polypropylene glycols —$(C_3H_6O)_p$— where p=1 to p=20, in particular p=1 to p=12, or polyester units, such as polyhydroxybutyric acid —$(CH[CH_3]$-$CH_2$—$COO)_q$— or polylactic acid —$(CH[CH_3]$—$COO)_q$—where q=1 to q=15, in particular q=1 to q=8,
n, m are identical or different and independently of one another are zero or 1, preferably zero, and M is a cation, for example a metal cation, such as an alkali metal or alkaline earth metal cation, or an ammonium cation which may be alkyl-substituted.

Examples of sulfosuccinates present according to the invention are
a1) sulfosuccinate which is esterified once or twice with linear, cyclic or branched aliphatic, cycloaliphatic and/or aromatic alcohols, having, for example, 1 to 22 carbon atoms in the alkyl radical, preferably mono- or dialkali metal sulfosuccinate, in particular mono- or disodium sulfosuccinate, which is esterified once or twice with methanol, ethanol, (iso)propanol, (iso)butanol, (iso)pentanol, (iso)hexanol, cyclohexanol, (iso)heptanol, (iso)octanol (in particular: ethylhexanol), (iso)nonanol, (iso)decanol, (iso)undecanol, (iso)dodecanol or (iso)tridecanol, a2) sulfosuccinate which is esterified once or twice with (poly)alkylene oxide adducts of alcohols, having, for example, 1 to 22 carbon atoms in the alkyl radical and 1 to 200, preferably 2 to 200, alkylene oxide units in the (poly)alkylene oxide moiety, preferably mono- or dialkali metal sulfosuccinate, in particular mono- or disodium sulfosuccinate, which is esterified once or twice with dodecyl/tetradecyl alcohol plus 2-5 mol of ethylene oxide or with i-tridecyl plus 3 mol of ethylene oxide, a3) the dialkali metal salt, preferably the disodium salt, of maleic anhydride which has been reacted with one equivalent of an amine or an amino-terminated (poly)alkylene oxide adduct of an alcohol, an amine, a fatty acid, an ester or an amide and then sulfonated, having, for example, 1 to 22 carbon atoms in the alkyl radical and 1 to 200, preferably 2 to 200, oxyalkylene units in the (poly)alkylene oxide moiety, preferably the disodium salt of maleic anhydride which has been reacted with one equivalent of coconut fatty amine and then sulfonated, a4) the dialkali metal salt, preferably the disodium salt, of maleic anhydride which has been reacted with one equivalent of an amide or a (poly)alkylene oxide adduct of an amide and then sulfonated, having, for example, 1 to 22 carbon atoms in the alkyl radical and 1 to 200, preferably 2 to 200, oxyalkylene units in the (poly)alkylene oxide moiety, preferably the disodium salt of maleic anhydride which has been reacted with one equivalent of oleylamide+2 mol of ethylene oxide and then sulfonated, and/or a5) the tetraalkali metal salt, preferably the tetrasodium salt, of N-(1,2-dicarboxy-ethyl)-N-octadecylsulfosuccinamate.

Examples of sulfosuccinates of groups a1) to a5) which are commercially available and preferred within the context of the present invention are listed below:

a1) sodium dialkylsulfosuccinate, for example sodium di-($C_4$-$C_{18}$)-alkylsulfosuccinate, such as sodium diisooctylsulfosuccinate, preferably sodium di(2-ethylhexyl)sulfosuccinate, commercially available, for example, in the form of the Aerosol® brands (Cytec), the Agrilan® or Lankropol® brands (Akzo Nobel), the Empimin® brands (Albright&Wilson), the Cropol® brands (Croda), the Lutensit® brands (BASF), the Triton® brands (Union Carbide), the Geropon® brands (Rhodia) or the Imbirol®, Madeol® or Polirol® brands (Cesalpinia), a2) sodium alcohol polyethylene glycol ether sulfosuccinate, commercially available, for example, in the form of Geropon® ACR brands, a3) disodium alcohol polyethylene glycol ether semisulfosuccinate, commercially available, for example, in the form of the Aerosol® brands (Cytec), the Marlinat® or Sermul® brands (Condea), the Empicol® brands (Albright&Wilson), the Secosol® brands (Stepan), the Geropon® brands (Rhodia), the Disponil® or Texapon® brands (Cognis) or the Rolpon® brands (Cesalpinia), a4) disodium N-alkylsulfosuccinamate, commercially available, for example, in the form of the Aerosol® brands (Cytec), the Rewopol® or Rewoderm® brands (Rewo), the Empimin® brands (Albright&Wilson), the Geropon® brands (Rhodia) or the Polirol® brands (Cesalpinia), a5) disodium fatty acid amide polyethylene glycol ether semisulfosuccinate, commercially available, for example, in the form of the Elfanol® or Lankropol® brands (Akzo Nobel), the Rewoderm®, Rewocid® or Rewopol® brands (Rewo), the Emcol® brands (Witco), the Standapol® brands (Cognis) or the Rolpon® brands (Cesalpinia), and a6) tetrasodium N-(1,2-dicarboxyethyl)-N-octadecylsulfosuccinamate, commercially available, for example, in the form of Aerosol 22® (Cytec).

Sulfosuccinates are commercially available, for example, as AEROSOL® (CYTEC), AGRILAN® or LANKROPOL® (AKZO NOBEL), EMPIMIN® (HUNTSMAN), CROPOL® (CRODA), LUTENSIT® (BASF), TRITON® GR series (UNIONCARBIDE), IMBIROL®/MADEOL®/POLIROL® (CESALPINIA); as GEROPON®AR series or as GEROPON® SDS (RHODIA).

Preferred sulfosuccinates are, for example, the sodium, potassium anrd ammonium salts of bis(alkyl)sulfosuccinates, where the alkyl radicals are identical or different and contain 4 to 16 carbon atoms and are preferably butyl, hexyl, octyl, such as 2-ethylhexyl or decyl radicals, which may be straight-chain or branched. Alkali metl di(octyl)sulfosuccinates, such as sodium di(2-ethylhexyl)sulfosuccinate, are particularly preferred.

The total proportion of sulfosuccinates in the liquid formulations according to the invention is generally between 0.1-60% by weight, in particular 1-40% by weight.

Customary auxiliaries and additives (component f) which may also be contained in the liquid formulations according to the invention are, for example: surfactants, such as emulsifiers and dispersants, thickeners and thixotropic agents, adjuvants, wetting agents, anti-drift agents, adhesives, penetrants, preservatives and antifreeze agents, antioxidants, solubilizers, fillers, carriers and colorants, antifoams, fertilizers, evaporation inhibitors and agents which modify pH and viscosity.

Suitable emulsifiers and dispersants are, for example, non-ionic emulsifiers and dispersants, for example:

1) polyalkoxylated, preferably polyethoxylated, saturated and unsaturated aliphatic alcohols,
   having 8 to 24 carbon atoms in the alkyl radical, which is derived from the corresponding fatty acids or from petrochemical products, and
   having 1 to 100, preferably 2 to 50, ethylene oxide units (EO), it being possible for the free hydroxyl group to be alkoxylated,
   which are commercially available, for example as Genapol® X and Genapol® O series (Clariant), Crovol® M series (Croda) or as Lutensol® series (BASF), or are obtainable therefrom by etherification, for example Genapol®X060 methyl ether, 2) polyalkoxylated, preferably polyethoxylated, arylalkylphenols, such as, for example, 2,4,6-tris-(1-phenylethyl)phenol (tristyrylphenol) having an average degree of ethoxylation of between 10 and 80, preferably from 16 to 40, such as, for example SOPROPHOR® BSU (RHODIA) or HOE S 3474 (CLARIANT), 3) polyalkoxylated, preferably polyethoxylated, alkylphenols having one or more alkyl radicals, such as, for example, nonylphenol or tri-sec-butylphenol, and a degree of ethoxylation of between 2 and 40, preferably from 4 to 15, such as, for example, ARKOPAL® N series or SAPOGENAT® T series (CLARIANT), 4) polyalkoxylated, preferably polyethoxylated, hydroxyfatty acids or glycerides which contain hydroxyfatty acids, such as, for example, ricinine or castor oil, having a degree of ethoxylation of between 10 and 80, preferably from 25 to 40, such as, for example, the EMULSOGEN® EL series (CLARIANT) or the AGNIQUE® CSO series (COGNIS),
5) polyalkoxylated, preferably polyethoxylated, sorbitan esters, such as, for example, Atplus® 309 F (UNIQEMA) or the Alkamuls® series (Rhodia),
6) di- and tri-block copolymers, for example from alkylene oxides, for example from ethylene oxide and propylene oxide, having average molar masses between 200 and 10 000, preferably from 1000 to 4000, g/mol, the proportion by mass of the polyethoxylated block varying between 10 and 80%, such as, for example, the GENAPOL® PF series (CLARIANT), the PLURONIC® series (BASF), or the SYNPERONIC® PE series (UNIQEMA).

Preferred nonionic emulsifiers and dispersants are, for example, polyethoxylated alcohols, polyethoxylated triglycerides which contain hydroxyfatty acids and polyethylene oxide/polypropylene oxide block copolymers.

The total proportion of nonionic emulsifiers and dispersants in the liquid formulations according to the invention is generally between 0 and 20% by weight. If nonionic emulsifiers and dispersants are, in addition to their emulsifying/dispersing properties, also used for increasing the biological effectiveness, for example as penetrants or adhesives, their proportion in the liquid formulations according to the invention can be increased to up to 60% by weight.

Also suitable are ionic emulsifiers and dispersants, for example:
1) polyalkoxylated, preferably polyethoxylated, emulsifiers/dispersants (cf. component e) which are ionically modified, for example by conversion of the terminal free hydroxyl function of the polyethylene oxide block into a sulfate or phosphate ester (for example as alkali metal and alkaline earth metal salts), such as, for example, Genapol® LRO or dispersant 3618 (Clariant), Emulphor® (BASF) or Crafol® AP (Cognis),
2) alkali metal and alkaline earth metal salts of alkylarylsulfonic acids having a straight-chain or branched alkyl chain, such as phenylsulfonate CA or phenylsulfonate CAL (Clariant), Atlox® 3377BM (ICI), or the Empiphos® TM series (Huntsman),
3) polyelectrolytes, such as lignosulfonates, condensates of naphthalenesulfonate and formaldehyde, polystyrenesulfonate or sulfonated unsaturated or aromatic polymers (polystyrenes, polybutadienes or polyterpenes), such as the Tamol® series (BASF), Morwet® D425 (Witco), the Kraftsperse® series (Westvaco) or the Borresperse® series (Borregard).

Preferred ionic emulsifiers/dispersants are, for example, salts of alkylarylsulfonic acids and polyelectrolytes from the polycondensation of naphthalenesulfonate and formaldehyde.

The total proportion of ionic emulsifiers and dispersants of component f) in the liquid formulations according to the invention is generally between 0 and 20% by weight, in particular between 0 and 8% by weight.

Suitable thickeners and thixotropic agents are, for example:
1) modified natural silicates, such as chemically modified bentonites, hectorites, attapulgites, montmorillonites, smectites or other silicate minerals, such as BENTONE® (ELEMENTIS), ATTAGEL® (ENGELHARD), AGSORB® (OIL-DRI CORPORATION) or HECTORITE® (AKZO NOBEL),
2) synthetic silicates, such as silicates of the SIPERNAT®, AEROSIL® or DUROSIL® series (DEGUSSA), the CAB-O-SIL® series (CABOT) or the VAN GEL series (R. T. VANDERBILT),
3) thickeners based on synthetic polymers, such as thickeners of the THIXIN® or THIXATROL® series (ELEMENTIS),
4) thickeners based on natural polymers and natural oils, for example from the THIXIN® or THIXATROL® series (ELEMENTIS).

Preferred thickeners and thixotropic agents are, for example, modified phyllosilicates and thickeners based on synthetic polymers.

The proportion of thickeners and thixotropic agents in the liquid formulations according to the invention is generally between 0 and 5% by weight, in particular between 0.2 and 4% by weight.

Preference is given to liquid formulations according to the invention comprising:
a) 0.1 to 50% by weight, preferably 0.1 to 30% by weight, of one or more herbicidally active compounds from the group of the ALS inhibitors, preferably the sulfonamides,
b) 20 to 90% by weight of one or more organic solvents, preferably from the group of the hydrocarbons or the fatty acid esters,
c) 0.01 to 10% by weight of one or more inorganic salts, preferably basic inorganic salts,
d) 0 to 40% by weight, preferably 0.1 to 40% by weight, of one or more agrochemically active compounds different from a),
e) 0 to 40% by weight, preferably 0.1-40% by weight, of one or more sulfosuccinates, preferably di(alkyl)sulfosuccinates,
f) 0-60% by weight, preferably 1-60% by weight, of customary auxiliaries and additives, in particular 0 to 30% by weight of one or more nonionic emulsifiers and dispersants, 0 to 8% by weight of one or more ionic emulsifiers and dispersants and 0 to 4% by weight of one or more thickeners and thixotriopic agents.

In a preferred embodiment, the liquid formulation according to the invention comprises
a) one or more sulfonamides of the formula (I) and/or salts thereof, preferably A1, A2, A3, A4, A5, A6, A7, A8, A9, A10, A11, A12, A13 and/or A14,
b) an organic solvent from the group of the aliphatic hydrocarbons, the mixtures of aromatic and aliphatic hydrocarbons and the vegetable oils, such as rapeseed oil methyl ester,
c) one or more carbonates and/or bicarbonates, preferably an alkali metal carbonate and/or alkali metal bicarbonate, such as $Na_2CO_3$, $K_2CO_3$, $NaHCO_3$ or $KHCO_3$,
d) optionally one or more agrochemically active compounds different from a), for example a safener from the group consisting of S1-1, S1-9 and S2-1, and/or a herbicidally active compound from the group consisting of diflufenican, bromoxynil (in particular bromoxynil octanoate), 2,4-D (in particular 2,4-D esters, such as 2,4-D isobutyl ester) and fenoxaprop-P-ethyl,
e) optionally a sulfosuccinate, for example sodium di(2-ethylhexyl)sulfosuccinate, and
f) optionally one or more customary auxiliaires and additives.

Particularly preferred examples which may be mentioned are liquid formulations according to the invention comprising the compounds listed below; however, this does not limit the invention. Here, Solvesso is a solvent from the Solvesso® series, preferably Solvesso® 200, Bayol is a solvent from the Bayol® series, preferably Bayol®82, Edenor=Edenor® MESU and Actirob=Actirob® B.

A1+Solvesso+$Na_2CO_3$, A1+Bayol+$Na_2CO_3$, A1+rapeseed oil methyl ester, for example Edenor or Actirob+$Na_2CO_3$, A2+Solvesso+$Na_2CO_3$, A2+Bayol+$Na_2CO_3$, A2+rapeseed oil methyl ester, for example Edenor or Actirob+$Na_2CO_3$, A3+Solvesso+$Na_2CO_3$, A3+Bayol+$Na_2CO_3$, A3+rapeseed oil methyl ester, for example Edenor or Actirob+Na$_2$CO$_3$, A4+Solvesso+Na$_2$CO$_3$, A4+Bayol+Na$_2$CO$_3$, A4+rapeseed oil methyl ester, for example Edenor or Actirob+Na$_2$CO$_3$, A5+Solvesso+Na$_2$CO$_3$, A5+Bayol+Na$_2$CO$_3$, A5+rapeseed oil methyl ester, for example Edenor or Actirob+Na$_2$CO$_3$, A6+Solvesso+Na$_2$CO$_3$, A6+Bayol+Na$_2$CO$_3$, A6+rapeseed oil methyl ester, for example Edenor or Actirob+Na$_2$CO$_3$, A7+Solvesso+Na$_2$CO$_3$, A7+Bayol+Na$_2$CO$_3$, A7+rapeseed oil methyl ester, for example Edenor or Actirob+Na$_2$CO$_3$, A8+Solvesso+Na$_2$CO$_3$, A8+Bayol+Na$_2$CO$_3$, A8+rapeseed oil methyl ester, for example Edenor or Actirob+Na$_2$CO$_3$, A9+Solvesso+Na$_2$CO$_3$, A9+Bayol+Na$_2$CO$_3$, A9+rapeseed oil methyl ester, for example Edenor or Actirob+Na$_2$CO$_3$, A10+Solvesso+Na$_2$CO$_3$, A10+Bayol+Na$_2$CO$_3$, A10+rapeseed oil methyl ester, for example Edenor or Actirob+Na$_2$CO$_3$, A11+Solvesso+Na$_2$CO$_3$, A11+Bayol+Na$_2$CO$_3$, A11+rapeseed oil methyl ester, for example Edenor or Actirob+Na$_2$CO$_3$, A12+Solvesso+Na$_2$CO$_3$, A12+Bayol+Na$_2$CO$_3$, A12+rapeseed oil methyl ester, for example Edenor or Actirob+Na$_2$CO$_3$, A13+Solvesso+Na$_2$CO$_3$, A13+Bayol+Na$_2$CO$_3$, A13+rapeseed oil methyl ester, for example Edenor or Actirob+Na$_2$CO$_3$, A14+Solvesso+Na$_2$CO$_3$, A14+Bayol+Na$_2$CO$_3$, A14+rapeseed oil methyl ester, for example Edenor or Actirob+Na$_2$CO$_3$, A1+Solvesso+K$_2$CO$_3$, A1+Bayol+K$_2$CO$_3$, A1+rapeseed oil methyl ester, for example Edenor or Actirob+K$_2$CO$_3$, A2+Solvesso+K$_2$CO$_3$, A2+Bayol+K$_2$CO$_3$, A2+rapeseed oil methyl ester, for example Edenor or Actirob+K$_2$CO$_3$, A3+Solvesso+K$_2$CO$_3$, A3+Bayol+K$_2$CO$_3$, A3+rapeseed oil methyl ester, for example Edenor or Actirob+K$_2$CO$_3$, A4+Solvesso+K$_2$CO$_3$, A4+Bayol+K$_2$CO$_3$, A4+rapeseed oil methyl ester, for example Edenor or Actirob+K$_2$CO$_3$, A5+Solvesso+K$_2$CO$_3$, A5+Bayol+K$_2$CO$_3$, A5+rapeseed oil methyl ester, for example Edenor or Actirob+K$_2$CO$_3$, A6+Solvesso+K$_2$CO$_3$, A6+Bayol+K$_2$CO$_3$, A6+rapeseed oil methyl ester, for example Edenor or Actirob+K$_2$CO$_3$, A7+Solvesso+K$_2$CO$_3$, A7+Bayol+K$_2$CO$_3$, A7+rapeseed oil methyl ester, for example Edenor or Actirob+K$_2$CO$_3$, A8+Solvesso+K$_2$CO$_3$, A8+Bayol+K$_2$CO$_3$, A8+rapeseed oil methyl ester, for example Edenor or Actirob+K$_2$CO$_3$, A9+Solvesso+K$_2$CO$_3$, A9+Bayol+K$_2$CO$_3$, A9+rapeseed oil methyl ester, for example Edenor or Actirob+K$_2$CO$_3$, A10+Solvesso+K$_2$CO$_3$, A10+Bayol+K$_2$CO$_3$, A10+rapeseed oil methyl ester, for example Edenor or Actirob+K$_2$CO$_3$, A11+Solvesso+K$_2$CO$_3$, A11+Bayol+K$_2$CO$_3$, A11+rapeseed oil methyl ester, for example Edenor or Actirob+K$_2$CO$_3$, A12+Solvesso+K$_2$CO$_3$, A12+Bayol+K$_2$CO$_3$, A12+rapeseed oil methyl ester, for example Edenor or Actirob+K$_2$CO$_3$, A13+Solvesso+K$_2$CO$_3$, A13+Bayol+K$_2$CO$_3$, A13+rapeseed oil methyl ester, for example Edenor or Actirob+K$_2$CO$_3$, A14+Solvesso+K$_2$CO$_3$, A14+Bayol+K$_2$CO$_3$, A14+rapeseed oil methyl ester, for example Edenor or Actirob+K$_2$CO$_3$, A1+Solvesso+NaHCO$_3$, A1+Bayol+NaHCO$_3$, A1+rapeseed oil methyl ester, for example Edenor or Actirob+NaHCO$_3$, A2+Solvesso+NaHCO$_3$, A2+Bayol+NaHCO$_3$, A2+rapeseed oil methyl ester, for example Edenor or Actirob+NaHCO$_3$, A3+Solvesso+NaHCO$_3$, A3+Bayol+NaHCO$_3$, A3+rapeseed oil methyl ester, for example Edenor or Actirob+NaHCO$_3$, A4+Solvesso+NaHCO$_3$, A4+Bayol+NaHCO$_3$, A4+rapeseed oil methyl ester, for example Edenor or Actirob+NaHCO$_3$, A5+Solvesso+NaHCO$_3$, A5+Bayol+NaHCO$_3$, A5+rapeseed oil methyl ester, for example Edenor or Actirob+NaHCO$_3$, A6+Solvesso+NaHCO$_3$, A6+Bayol+NaHCO$_3$, A6+rapeseed oil methyl ester, for example Edenor or Actirob+NaHCO$_3$, A7+Solvesso+NaHCO$_3$, A7+Bayol+NaHCO$_3$, A7+rapeseed oil methyl ester, for example Edenor or Actirob+NaHCO$_3$, A8+Solvesso+NaHCO$_3$, A8+Bayol+NaHCO$_3$, A8+rapeseed oil methyl ester, for example Edenor or Actirob+NaHCO$_3$, A9+Solvesso+NaHCO$_3$, A9+Bayol+NaHCO$_3$, A9+rapeseed oil methyl ester, for example Edenor or Actirob+NaHCO$_3$, A10+Solvesso+NaHCO$_3$, A10+Bayol+NaHCO$_3$, A10+rapeseed oil methyl ester, for example Edenor or Actirob+NaHCO$_3$, A11+Solvesso+NaHCO$_3$, A11+Bayol+NaHCO$_3$, A11+rapeseed oil methyl ester, for example Edenor or Actirob+NaHCO$_3$, A12+Solvesso+NaHCO$_3$, A12+Bayol+NaHCO$_3$, A12+rapeseed oil methyl ester, for example Edenor or Actirob+NaHCO$_3$, A13+Solvesso+NaHCO$_3$, A13+Bayol+NaHCO$_3$, A13+rapeseed oil methyl ester, for example Edenor or Actirob+NaHCO$_3$, A14+Solvesso+NaHCO$_3$, A14+Bayol+NaHCO$_3$, A14+rapeseed oil methyl ester, for example Edenor or Actirob+NaHCO$_3$, A1+Solvesso+KHCO$_3$, A1+Bayol+KHCO$_3$, A1+rapeseed oil methyl ester, for example Edenor or Actirob+KHCO$_3$, A2+Solvesso+KHCO$_3$, A2+Bayol+KHCO$_3$, A2+rapeseed oil methyl ester, for example Edenor or Actirob+KHCO$_3$, A3+Solvesso+KHCO$_3$, A3+Bayol+KHCO$_3$, A3+rapeseed oil methyl ester, for example Edenor or Actirob+KHCO$_3$, A4+Solvesso+KHCO$_3$, A4+Bayol+KHCO$_3$, A4+rapeseed oil methyl ester, for example Edenor or Actirob+KHCO$_3$, A5+Solvesso+KHCO$_3$, A5+Bayol+KHCO$_3$, A5+rapeseed oil methyl ester, for example Edenor or Actirob+KHCO$_3$, A6+Solvesso+KHCO$_3$, A6+Bayol+KHCO$_3$, A6+rapeseed oil methyl ester, for example Edenor or Actirob+KHCO$_3$, A7+Solvesso+KHCO$_3$, A7+Bayol+KHCO$_3$, A7+rapeseed oil methyl ester, for example Edenor or Actirob+KHCO$_3$, A8+Solvesso+KHCO$_3$, A8+Bayol+KHCO$_3$, A8+rapeseed oil methyl ester, for example Edenor or Actirob+KHCO$_3$, A9+Solvesso+KHCO$_3$, A9+Bayol+KHCO$_3$, A9+rapeseed oil methyl ester, for example Edenor or Actirob+KHCO$_3$, A10+Solvesso+KHCO$_3$, A10+Bayol+KHCO$_3$, A10+rapeseed oil methyl ester, for example Edenor or Actirob+KHCO$_3$, A11+Solvesso+KHCO$_3$, A11+Bayol+KHCO$_3$, A11+rapeseed oil methyl ester, for example Edenor or Actirob+KHCO$_3$, A12+Solvesso+KHCO$_3$, A12+Bayol+KHCO$_3$, A12+rapeseed oil methyl ester, for example Edenor or Actirob+KHCO$_3$, A13+Solvesso+KHCO$_3$, A13+Bayol+KHCO$_3$, A13+rapeseed oil methyl ester, for example Edenor or Actirob+KHCO$_3$, A14+Solvesso+KHCO$_3$, A14+Bayol+KHCO$_3$, A14+rapeseed oil methyl ester, for example Edenor or Actirob+KHCO$_3$;

A1+Solvesso+Na$_2$CO$_3$+S1-1, A1+Bayol+Na$_2$CO$_3$+S1-1, A1+rapeseed oil methyl ester, for example Edenor or Actirob+Na$_2$CO$_3$+S1-1, A2+Solvesso+Na$_2$CO$_3$+S1-1, A2+Bayol+Na$_2$CO$_3$+S1-1, A2+rapeseed oil methyl ester, for example Edenor or Actirob+Na$_2$CO$_3$+S1-1, A3+Solvesso+Na$_2$CO$_3$+S1-1, A3+Bayol+Na$_2$CO$_3$+S1-1, A3+rapeseed oil methyl ester, for example Edenor or Actirob+Na$_2$CO$_3$+S1-1, A4+Solvesso+Na$_2$CO$_3$+S1-1, A4+Bayol+Na$_2$CO$_3$+S1-1, A4+rapeseed oil methyl ester, for example Edenor or Actirob+Na$_2$CO$_3$+S1-1, A5+Solvesso+Na$_2$CO$_3$+S1-1, A5+Bayol+Na$_2$CO$_3$+S1-1, A5+rapeseed oil methyl ester, for example Edenor or Actirob+Na$_2$CO$_3$+S1-1, A6+Solvesso+Na$_2$CO$_3$+S1-1, A6+Bayol+Na$_2$CO$_3$+S1-1, A6+rapeseed oil methyl ester, for example Edenor or Actirob+Na$_2$CO$_3$+S1-1, A7+Solvesso+Na$_2$CO$_3$+S1-1, A7+Bayol+Na$_2$CO$_3$+S1-1, A7+rapeseed oil methyl ester, for example Edenor or Actirob+Na$_2$CO$_3$+S1-1, A8+Solvesso+Na$_2$CO$_3$+S1-1, A8+Bayol+Na$_2$CO$_3$+S1-1, A8+rapeseed oil methyl ester, for example Edenor or Actirob+Na$_2$CO$_3$+S1-1, A9+Solvesso+Na$_2$CO$_3$+S1-1, A9+Bayol+Na$_2$CO$_3$+S1-1, A9+rapeseed oil methyl ester, for example Edenor or Actirob+Na$_2$CO$_3$+S1-1, A10+Solvesso+Na$_2$CO$_3$+S1-1, A10+Bayol+Na$_2$CO$_3$+S1-1, A10+rapeseed oil methyl ester, for example Edenor or Actirob+Na$_2$CO$_3$+S1-1, A11+Solvesso+Na$_2$CO$_3$+S1-1, A11+Bayol+Na$_2$CO$_3$+S1-1, A11+rapeseed oil methyl ester, for example Edenor or Actirob+Na$_2$CO$_3$+S1-1, A12+

Solvesso+Na₂CO₃+S1-1, A12+Bayol+Na₂CO₃+S1-1, A12+rapeseed oil methyl ester, for example Edenor or Actirob+Na₂CO₃+S1-1, A13+Solvesso+Na₂CO₃+S1-1, A13+Bayol+Na₂CO₃+S1-1, A13+rapeseed oil methyl ester, for example Edenor or Actirob+Na₂CO₃+S1-1, A14+Solvesso+Na₂CO₃+S1-1, A14+Bayol+Na₂CO₃S1-1, A14+rapeseed oil methyl ester, for example Edenor or Actirob+Na₂CO₃+S1-1, A1+Solvesso+K₂CO₃+S1-1, A1+Bayol+K₂CO₃+S1-1, A1+rapeseed oil methyl ester, for example Edenor or Actirob+K₂CO₃+S1-1, A2+Solvesso+K₂CO₃+S1-1, A2+Bayol+K₂CO₃+S1-1, A2+rapeseed oil methyl ester, for example Edenor or Actirob+K₂CO₃+S1-1, A3+Solvesso+K₂CO₃+S1-1, A3+Bayol+K₂CO₃+S1-1, A3+rapeseed oil methyl ester, for example Edenor or Actirob+K₂CO₃+S1-1, A4+Solvesso+K₂CO₃+S1-1, A4+Bayol+K₂CO₃+S1-1, A4+rapeseed oil methyl ester, for example Edenor or Actirob+K₂CO₃+S1-1, A5+Solvesso+K₂CO₃+S1-1, A5+Bayol+K₂CO₃+S1-1, A5+rapeseed oil methyl ester, for example Edenor or Actirob+K₂CO₃+S1-1, A6+Solvesso+K₂CO₃+S1-1, A6+Bayol+K₂CO₃+S1-1, A6+rapeseed oil methyl ester, for example Edenor or Actirob+K₂CO₃+S1-1, A7+Solvesso+K₂CO₃+S1-1, A7+Bayol+K₂CO₃+S1-1, A7+rapeseed oil methyl ester, for example Edenor or Actirob+K₂CO₃+S1-1, A8+Solvesso+K₂CO₃+S1-1, A8+Bayol+K₂CO₃+S1-1, A8+rapeseed oil methyl ester, for example Edenor or Actirob+K₂CO₃+S1-1, A9+Solvesso+K₂CO₃+S1-1, A9+Bayol+K₂CO₃+S1-1, A9+rapeseed oil methyl ester, for example Edenor or Actirob+K₂CO₃+S1-1, A10+Solvesso+K₂CO₃+S1-1, A10+Bayol+K₂CO₃+S1-1, A10+rapeseed oil methyl ester, for example Edenor or Actirob+K₂CO₃+S1-1, A11+Solvesso+K₂CO₃+S1-1, A11+Bayol+K₂CO₃+S1-1, A11+rapeseed oil methyl ester, for example Edenor or Actirob+K₂CO₃+S1-1, A12+Solvesso+K₂CO₃+S1-1, A12+Bayol+K₂CO₃+S1-1, A12+rapeseed oil methyl ester, for example Edenor or Actirob+K₂CO₃+S1-1, A13+Solvesso+K₂CO₃+S1-1, A13+Bayol+K₂CO₃+S1-1, A13+rapeseed oil methyl ester, for example Edenor or Actirob+K₂CO₃+S1-1, A14+Solvesso+K₂CO₃+S1-1, A14+Bayol+K₂CO₃+S1-1, A14+rapeseed oil methyl ester, for example Edenor or Actirob+K₂CO₃+S1-1, A1+Solvesso+NaHCO₃+S1-1, A1+Bayol+NaHCO₃+S1-1, A1+rapeseed oil methyl ester, for example Edenor or Actirob+NaHCO₃+S1-1, A2+Solvesso+NaHCO₃+S1-1, A2+Bayol+NaHCO₃+S1-1, A2+rapeseed oil methyl ester, for example Edenor or Actirob+NaHCO₃+S1-1, A3+Solvesso+NaHCO₃+S1-1, A3+Bayol+NaHCO₃+S1-1, A3+rapeseed oil methyl ester, for example Edenor or Actirob+NaHCO₃+S1-1, A4+Solvesso+NaHCO₃+S1-1, A4+Bayol+NaHCO₃+S1-1, A4+rapeseed oil methyl ester, for example Edenor or Actirob+NaHCO₃+S1-1, A5+Solvesso+NaHCO₃+S1-1, A5+Bayol+NaHCO₃+S1-1, A5+rapeseed oil methyl ester, for example Edenor or Actirob+NaHCO₃+S1-1, A6+Solvesso+NaHCO₃+S1-1, A6+Bayol+NaHCO₃+S1-1, A6+rapeseed oil methyl ester, for example Edenor or Actirob+NaHCO₃+S1-1, A7+Solvesso+NaHCO₃+S1-1, A7+Bayol+NaHCO₃+S1-1, A7+rapeseed oil methyl ester, for example Edenor or Actirob+NaHCO₃+S1-1, A8+Solvesso+NaHCO₃+S1-1, A8+Bayol+NaHCO₃+S1-1, A8+rapeseed oil methyl ester, for example Edenor or Actirob+NaHCO₃+S1-1, A9+Solvesso+NaHCO₃+S1-1, A9+Bayol+NaHCO₃+S1-1, A9+rapeseed oil methyl ester, for example Edenor or Actirob+NaHCO₃+S1-1, A10+Solvesso+NaHCO₃+S1-1, A10+Bayol+NaHCO₃+S1-1, A10+rapeseed oil methyl ester, for example Edenor or Actirob+NaHCO₃+S1-1, A11+Solvesso+NaHCO₃+S1-1, A11+Bayol+NaHCO₃+S1-1, A11+rapeseed oil methyl ester, for example Edenor or Actirob+NaHCO₃+S1-1, A12+Solvesso+NaHCO₃+S1-1, A12+Bayol+NaHCO₃+S1-1, A12+rapeseed oil methyl ester, for example Edenor or Actirob+NaHCO₃+S1-1, A13+Solvesso+NaHCO₃+S1-1, A13+Bayol+NaHCO₃+S1-1, A13+rapeseed oil methyl ester, for example Edenor or Actirob+NaHCO₃+S1-1, A14+Solvesso+NaHCO₃+S1-1, A14+Bayol+NaHCO₃+S1-1, A14+rapeseed oil methyl ester, for example Edenor or Actirob+NaHCO₃+S1-1, A1+Solvesso+KHCO₃+S1-1, A1+Bayol+KHCO₃+S1-1, A1+rapeseed oil methyl ester, for example Edenor or Actirob+KHCO₃+S1-1, A2+Solvesso+KHCO₃+S1-1, A2+Bayol+KHCO₃+S1-1, A2+rapeseed oil methyl ester, for example Edenor or Actirob+KHCO₃+S1-1, A3+Solvesso+KHCO₃+S1-1, A3+Bayol+KHCO₃+S1-1, A3+rapeseed oil methyl ester, for example Edenor or Actirob+KHCO₃+S1-1, A4+Solvesso+KHCO₃+S1-1, A4+Bayol+KHCO₃+S1-1, A4+rapeseed oil methyl ester, for example Edenor or Actirob+KHCO₃+S1-1, A5+Solvesso+KHCO₃+S1-1, A5+Bayol+KHCO₃+S1-1, A5+rapeseed oil methyl ester, for example Edenor or Actirob+KHCO₃+S1-1, A6+Solvesso+KHCO₃+S1-1, A6+Bayol+KHCO₃+S1-1, A6+rapeseed oil methyl ester, for example Edenor or Actirob+KHCO₃+S1-1, A7+Solvesso+KHCO₃+S1-1, A7+Bayol+KHCO₃+S1-1, A7+rapeseed oil methyl ester, for example Edenor or Actirob+KHCO₃+S1-1; A8+Solvesso+KHCO₃+S1-1, A8+Bayol+KHCO₃+S1-1, A8+rapeseed oil methyl ester, for example Edenor or Actirob+KHCO₃+S1-1; A9+Solvesso+KHCO₃+S1-1, A9+Bayol+KHCO₃+S1-1, A9+rapeseed oil methyl ester, for example Edenor or Actirob+KHCO₃+S1-1; A10+Solvesso+KHCO₃+S1-1, A10+Bayol+KHCO₃+S1-1, A10+rapeseed oil methyl ester, for example Edenor or Actirob+KHCO₃+S1-1; A11+Solvesso+KHCO₃+S1-1, A11+Bayol+KHCO₃+S1-1, A11+rapeseed oil methyl ester, for example Edenor or Actirob+KHCO₃+S1-1; A12+Solvesso+KHCO₃+S1-1, A12+Bayol+KHCO₃+S1-1, A12+rapeseed oil methyl ester, for example Edenor or Actirob+KHCO₃+S1-1; A13+Solvesso+KHCO₃+S1-1, A13+Bayol+KHCO₃+S1-1, A13+rapeseed oil methyl ester, for example Edenor or Actirob+KHCO₃+S1-1; A14+Solvesso+KHCO₃+S1-1, A14+Bayol+KHCO₃+S1-1, A14+rapeseed oil methyl ester, for example Edenor or Actirob+KHCO₃+S1-1;

A1+Solvesso+Na₂CO₃+S1-9, A1+Bayol+Na₂CO₃+S1-9, A1+rapeseed oil methyl ester, for example Edenor or Actirob+Na₂CO₃+S1-9, A2+Solvesso+Na₂CO₃+S1-9, A2+Bayol+Na₂CO₃+S1-9, A2+rapeseed oil methyl ester, for example Edenor or Actirob+Na₂CO₃+S1-9, A3+Solvesso+Na₂CO₃+S1-9, A3+Bayol+Na₂CO₃+S1-9, A3+rapeseed oil methyl ester, for example Edenor or Actirob+Na₂CO₃+S1-9, A4+Solvesso+Na₂CO₃+S1-9, A4+Bayol+Na₂CO₃+S1-9, A4+rapeseed oil methyl ester, for example Edenor or Actirob+Na₂CO₃+S1-9, A5+Solvesso+Na₂CO₃+S1-9, A5+Bayol+Na₂CO₃+S1-9, A5+rapeseed oil methyl ester, for example Edenor or Actirob+Na₂CO₃+S1-9, A6+Solvesso+Na₂CO₃+S1-9, A6+Bayol+Na₂CO₃+S1-9, A6+rapeseed oil methyl ester, for example Edenor or Actirob+Na₂CO₃+S1-9, A7+Solvesso+Na₂CO₃+S1-9, A7+Bayol+Na₂CO₃+S1-9, A7+rapeseed oil methyl ester, for example Edenor or Actirob+Na₂CO₃+S1-9, A8+Solvesso+Na₂CO₃+S1-9, A8+Bayol+Na₂CO₃+S1-9, A8+rapeseed oil methyl ester, for example Edenor or Actirob+Na₂CO₃+S1-9, A9+Solvesso+Na₂CO₃+S1-9, A9+Bayol+Na₂CO₃+S1-9, A9+rapeseed oil methyl ester, for example Edenor or Actirob+Na₂CO₃+S1-9, A10+Solvesso+Na₂CO₃+S1-9, A10+Bayol+Na₂CO₃+S1-9, A10+rapeseed oil methyl ester, for example Edenor or Actirob+Na₂CO₃+S1-9, A11+Solvesso+Na₂CO₃+S1-9, A11+Bayol+Na₂CO₃+S1-9, A11+rapeseed oil methyl ester, for example Edenor or Actirob+Na₂CO₃+S1-9, A12+

Solvesso+Na$_2$CO$_3$+S1-9, A12+Bayol+Na$_2$CO$_3$+S1-9, A12+rapeseed oil methyl ester, for example Edenor or Actirob+Na$_2$CO$_3$+S1-9, A13+Solvesso+Na$_2$CO$_3$+S1-9, A13+Bayol+Na$_2$CO$_3$+S1-9, A13+rapeseed oil methyl ester, for example Edenor or Actirob+Na$_2$CO$_3$+S1-9, A14+Solvesso+Na$_2$CO$_3$+S1-9, A14+Bayol+Na$_2$CO$_3$+S1-9, A14+rapeseed oil methyl ester, for example Edenor or Actirob+Na$_2$CO$_3$+S1-9, A1+Solvesso+K$_2$CO$_3$+S1-9, A1+Bayol+K$_2$CO$_3$+S1-9, A1+rapeseed oil methyl ester, for example Edenor or Actirob+K$_2$CO$_3$+S1-9, A2+Solvesso+K$_2$CO$_3$+S1-9, A2+Bayol+K$_2$CO$_3$+S1-9, A2+rapeseed oil methyl ester, for example Edenor or Actirob+K$_2$CO$_3$+S1-9, A3+Solvesso+K$_2$CO$_3$+S1-9, A3+Bayol+K$_2$CO$_3$+S1-9, A3+rapeseed oil methyl ester, for example Edenor or Actirob+K$_2$CO$_3$+S1-9, A4+Solvesso+K$_2$CO$_3$+S1-9, A4+Bayol+K$_2$CO$_3$+S1-9, A4+rapeseed oil methyl ester, for example Edenor or Actirob+K$_2$CO$_3$+S1-9, A5+Solvesso+K$_2$CO$_3$+S1-9, A5+Bayol+K$_2$CO$_3$+S1-9, A5+rapeseed oil methyl ester, for example Edenor or Actirob+K$_2$CO$_3$+S1-9, A6+Solvesso+K$_2$CO$_3$+S1-9, A6+Bayol+K$_2$CO$_3$+S1-9, A6+rapeseed oil methyl ester, for example Edenor or Actirob+K$_2$CO$_3$+S1-9, A7+Solvesso+K$_2$CO$_3$+S1-9, A7+Bayol+K$_2$CO$_3$+S1-9, A7+rapeseed oil methyl ester, for example Edenor or Actirob+K$_2$CO$_3$+S1-9, A8+Solvesso+K$_2$CO$_3$+S1-9, A8+Bayol+K$_2$CO$_3$+S1-9, A8+rapeseed oil methyl ester, for example Edenor or Actirob+K$_2$CO$_3$+S1-9, A9+Solvesso+K$_2$CO$_3$+S1-9, A9+Bayol+K$_2$CO$_3$+S1-9, A9+rapeseed oil methyl ester, for example Edenor or Actirob+K$_2$CO$_3$+S1-9, A10+Solvesso+K$_2$CO$_3$+S1-9, A10+Bayol+K$_2$CO$_3$+S1-9, A10+rapessed oil methyl ester, for example Edenor or Actirob+K$_2$CO$_3$+S1-9, A11+Solvesso+K$_2$CO$_3$+S1-9, A11+Bayol+K$_2$CO$_3$+S1-9, A11+rapeseed oil methyl ester, for example Edenor or Actirob+K$_2$CO$_3$+S1-9, A12+Solvesso+K$_2$CO$_3$+S1-9, A12+Bayol+K$_2$CO$_3$+S1-9, A12+rapeseed oil methyl ester, for example Edenor or Actirob+K$_2$CO$_3$+S1-9, A13+Solvesso+K$_2$CO$_3$+S1-9, A13+Bayol+K$_2$CO$_3$+S1-9, A13+rapeseed oil methyl ester, for example Edenor or Actirob+K$_2$CO$_3$+S1-9, A14+Solvesso+K$_2$CO$_3$+S1-9, A14+Bayol+K$_2$CO$_3$+S1-9, A14+rapeseed oil methyl ester, for example Edenor or Actirob+K$_2$CO$_3$+S1-9, A1+Solvesso+NaHCO$_3$+S1-9, A1+Bayol+NaHCO$_3$+S1-9, A1+-rapeseed oil methyl ester, for example Edenor or Actirob+NaHCO$_3$+S1-9, A2+Solvesso+NaHCO$_3$+S1-9, A2+Bayol+NaHCO$_3$+S1-9, A2+rapeseed oil methyl ester, for example Edenor or Actirob+NaHCO$_3$+S1-9, A3+Solvesso+NaHCO$_3$+S1-9, A3+Bayol+NaHCO$_3$+S1-9, A3+rapeseed oil methyl ester, for example Edenor or Actirob+NaHCO$_3$+S1-9, A4+Solvesso+NaHCO$_3$+S1-9, A4+Bayol+NaHCO$_3$+S1-9, A4+rapeseed oil methyl ester, for example Edenor or Actirob+NaHCO$_3$+S1-9, A5+Solvesso+NaHCO$_3$+S1-9, A5+Bayol+NaHCO$_3$+S1-9, A5+rapeseed oil methyl ester, for example Edenor or Actirob+NaHCO$_3$+S1-9, A6+Solvesso+NaHCO$_3$+S1-9, A6+Bayol+NaHCO$_3$+S1-9, A6+rapeseed oil methyl ester, for example Edenor or Actirob+NaHCO$_3$+S1-9, A7+Solvesso+NaHCO$_3$+S1-9, A7+Bayol+NaHCO$_3$+S1-9, A7+rapeseed oil methyl ester, for example Edenor or Actirob+NaHCO$_3$+S1-9, A8+Solvesso+NaHCO$_3$+S1-9, A8+Bayol+NaHCO$_3$+S1-9, A8+rapeseed oil methyl ester, for example Edenor or Actirob+NaHCO$_3$+S1-9, A9+Solvesso+NaHCO$_3$+S1-9, A9+Bayol+NaHCO$_3$+S1-9, A9+rapeseed oil methyl ester, for example Edenor or Actirob+NaHCO$_3$+S1-9, A10+Solvesso+NaHCO$_3$+S1-9, A10+Bayol+NaHCO$_3$+S1-9, A10+rapeseed oil methyl ester, for example Edenor or Actirob+NaHCO$_3$+S1-9, A11+Solvesso+NaHCO$_3$+S1-9, A11+Bayol+NaHCO$_3$+S1-9, A11+rapeseed oil methyl ester, for example Edenor or Actirob+NaHCO$_3$+S1-9, A12+Solvesso+NaHCO$_3$+S1-9, A12+Bayol+NaHCO$_3$+S1-9, A12+rapeseed oil methyl ester, for example Edenor or Actirob+NaHCO$_3$+S1-9, A13+Solvesso+NaHCO$_3$+S1-9, A13+Bayol+NaHCO$_3$+S1-9, A13+rapeseed oil methyl ester, for example Edenor or Actirob+NaHCO$_3$+S1-9, A14+Solvesso+NaHCO$_3$+S1-9, A14+Bayol+NaHCO$_3$+-S1-9, A14+rapeseed oil methyl ester, for example Edenor or Actirob+NaHCO$_3$+S1-9, A1+Solvesso+KHCO$_3$+S1-9, A1+Bayol+KHCO$_3$+S1-9, A1+rapeseed oil methyl ester, for example Edenor or Actirob+KHCO$_3$+S1-9, A2+Solvesso+KHCO$_3$+S1-9, A2+Bayol+KHCO$_3$+S1-9, A2+rapeseed oil methyl ester, for example Edenor or Actirob+KHCO$_3$+S1-9, A3+Solvesso+KHCO$_3$+S1-9, A3+Bayol+KHCO$_3$+S1-9, A3+rapeseed oil methyl ester, for example Edenor or Actirob+KHCO$_3$+S1-9, A4+Solvesso+KHCO$_3$+S1-9, A4+Bayol+KHCO$_3$+S1-9, A4+rapeseed oil methyl ester, for example Edenor or Actirob+KHCO$_3$+S1-9, A5+Solvesso+KHCO$_3$+S1-9, A5+Bayol+KHCO$_3$+S1-9, A5+rapeseed oil methyl ester, for example Edenor or Actirob+KHCO$_3$+S1-9, A6+Solvesso+KHCO$_3$+S1-9, A6+Bayol+KHCO$_3$+S1-9, A6+rapeseed oil methyl ester, for example Edenor or Actirob+KHCO$_3$+S1-9, A7+Solvesso+KHCO$_3$+S1-9, A7+Bayol+KHCO$_3$+S1-9, A7+rapeseed oil methyl ester, for example Edenor or Actirob+KHCO$_3$+S1-9, A8+Solvesso+KHCO$_3$+S1-9, A8+Bayol+KHCO$_3$+S1-9, A8+rapeseed oil methyl ester, for example Edenor or Actirob+KHCO$_3$+S1-9, A9+Solvesso+KHCO$_3$+S1-9, A9+Bayol+KHCO$_3$+S1-9, A9+rapeseed oil methyl ester, for example Edenor or Actirob+KHCO$_3$+S1-9, A10+Solvesso+KHCO$_3$+S1-9, A10+Bayol+KHCO$_3$+S1-9, A10+rapeseed oil methyl ester, for example Edenor or Actirob+KHCO$_3$+S1-9, A11+Solvesso+KHCO$_3$+S1-9, A11+Bayol+KHCO$_3$+S1-9, A11+rapeseed oil methyl ester, for example Edenor or Actirob+KHCO$_3$+S1-9, A12+Solvesso+KHCO$_3$+S1-9, A12+Bayol+KHCO$_3$+S1-9, A12+rapeseed oil methyl ester, for example Edenor or Actirob+KHCO$_3$+S1-9, A13+Solvesso+KHCO$_3$+S1-9, A13+Bayol+KHCO$_3$+S1-9, A13+rapeseed oil methyl ester, for example Edenor or Actirob+KHCO$_3$+S1-9, A14+Solvesso+KHCO$_3$+S1-9, A14+Bayol+KHCO$_3$+S1-9, A14+rapeseed oil methyl ester, for example Edenor or Actirob+KHCO$_3$+S1-9;

A1+Solvesso+Na$_2$CO$_3$+S2-1, A1+Bayol+Na$_2$CO$_3$+S2-1, A1+rapeseed oil methyl ester, for example Edenor or Actirob+Na$_2$CO$_3$+S2-1, A2+Solvesso+Na$_2$CO$_3$+S2-1, A2+Bayol+Na$_2$CO$_3$+S2-1, A2+rapeseed oil methyl ester, for example Edenor or Actirob+Na$_2$CO$_3$+S2-1, A3+Solvesso+Na$_2$CO$_3$+S2-1, A3+Bayol+Na$_2$CO$_3$+S2-1, A3+rapeseed oil methyl ester, for example Edenor or Actirob+Na$_2$CO$_3$+S2-1, A4+Solvesso+Na$_2$CO$_3$+S2-1, A4+Bayol+Na$_2$CO$_3$+S2-1, A4+rapeseed oil methyl ester, for example Edenor or Actirob+Na$_2$CO$_3$+S2-1, A5+Solvesso+Na$_2$CO$_3$+S2-1, A5+Bayol+Na$_2$CO$_3$+S2-1, A5+rapeseed oil methyl ester, for example Edenor or Actirob+Na$_2$CO$_3$+S2-1, A6+Solvesso+Na$_2$CO$_3$+S2-1, A6+Bayol+Na$_2$CO$_3$+S2-1, A6+rapeseed oil methyl ester, for example Edenor or Actirob+Na$_2$CO$_3$+S2-1, A7+Solvesso+Na$_2$CO$_3$+S2-1, A7+Bayol+Na$_2$CO$_3$+S2-1, A7+rapeseed oil methyl ester, for example Edenor or Actirob+Na$_2$CO$_3$+S2-1, A8+Solvesso+Na$_2$CO$_3$+S2-1, A8+Bayol+Na$_2$CO$_3$+S2-1, A8+rapeseed oil methyl ester, for example Edenor or Actirob+Na$_2$CO$_3$+S2-1, A9+Solvesso+Na$_2$CO$_3$+S2-1, A9+Bayol+Na$_2$CO$_3$+S2-1, A9+rapeseed oil methyl ester, for example Edenor or Actirob+Na$_2$CO$_3$+S2-1, A10+Solvesso+Na$_2$CO$_3$+S2-1, A10+Bayol+Na$_2$CO$_3$+S2-1, A10+rapeseed oil methyl ester, for example Edenor or Actirob+Na$_2$CO$_3$+S2-1, A11+Solvesso+Na$_2$CO$_3$+S2-1, A11+Bayol+Na$_2$CO$_3$+S2-1, A11+rapeseed oil methyl ester, for example Edenor or Actirob+Na$_2$CO$_3$+S2-1, A12+

Solvesso+Na$_2$CO$_3$+S2-1, A12+Bayol+Na$_2$CO$_3$+S2-1, A12+rapeseed oil methyl ester, for example Edenor or Actirob+Na$_2$CO$_3$+S2-1, A13+Solvesso+Na$_2$CO$_3$+S2-1, A13+Bayol+Na$_2$CO$_3$+S2-1, A13+rapeseed oil methyl ester, for example Edenor or Actirob+Na$_2$CO$_3$+S2-1, A14+Solvesso+Na$_2$CO$_3$+S2-1, A14+Bayol+Na$_2$CO$_3$+S2-1, A14+rapeseed oil methyl ester, for example Edenor or Actirob+Na$_2$CO$_3$+S2-1, A1+Solvesso+K$_2$CO$_3$+S2-1, A1+Bayol+K$_2$CO$_3$+S2-1, A1+rapeseed oil methyl ester, for example Edenor or Actirob+K$_2$CO$_3$+S2-1, A2+Solvesso+K$_2$CO$_3$+S2-1, A2+Bayol+K$_2$CO$_3$+S2-1, A2+rapeseed oil methyl ester, for example Edenor or Actirob+K$_2$CO$_3$+S2-1, A3+Solvesso+K$_2$CO$_3$+S2-1, A3+Bayol+K$_2$CO$_3$+S2-1, A3+rapeseed oil methyl ester, for example Edenor or Actirob+K$_2$CO$_3$+S2-1, A4+Solvesso+K$_2$CO$_3$+S2-1, A4+Bayol+K$_2$CO$_3$+S2-1, A4+rapeseed oil methyl ester, for example Edenor or Actirob+K2CO$_3$+S2-1, A5+Solvesso+K$_2$CO$_3$+S2-1, A5+Bayol+K$_2$CO$_3$+S2-1, A5+rapeseed oil methyl ester, for example Edenor or Actirob+K$_2$CO$_3$+S2-1, A6+Solvesso+K$_2$CO$_3$+S2-1, A6+Bayol+K$_2$CO$_3$+S2-1, A6+rapeseed oil methyl ester, for example Edenor or Actirob+K$_2$CO$_3$+S2-1, A7+Solvesso+K$_2$CO$_3$+S2-1, A7+Bayol+K$_2$CO$_3$+S2-1, A7+rapeseed oil methyl ester, for example Edenor or Actirob+K$_2$CO$_3$+S2-1, A8+Solvesso+K$_2$CO$_3$+S2-1, A8+Bayol+K$_2$CO$_3$+S2-1, A8+rapeseed oil methyl ester, for example Edenor or Actirob+K$_2$CO$_3$+S2-1, A9+Solvesso+K$_2$CO$_3$+S2-1, A9+Bayol+K$_2$CO$_3$+S2-1, A9+rapeseed oil methyl ester, for example Edenor or Actirob+K$_2$CO$_3$+S2-1, A10+Solvesso+K$_2$CO$_3$+S2-1, A10+Bayol+K$_2$CO$_3$+S2-1, A10+rapeseed oil methyl ester, for example Edenor or Actirob+K$_2$CO$_3$+S2-1, A11+Solvesso+K$_2$CO$_3$+S2-1, A11+Bayol+K$_2$CO$_3$+S2-1, A11+rapeseed oil methyl ester, for example Edenor or Actirob+K$_2$CO$_3$+S2-1, A12+Solvesso+K$_2$CO$_3$+S2-1, A12+Bayol+K$_2$CO$_3$+S2-1, A12+rapeseed oil methyl ester, for example Edenor or Actirob+K$_2$CO$_3$+S2-1, A13+Solvesso+K$_2$CO$_3$+S2-1, A13+Bayol+K$_2$CO$_3$+S2-1, A13+rapeseed oil methyl ester, for example Edenor or Actirob+K$_2$CO$_3$+S2-1, A14+Solvesso+K$_2$CO$_3$+S2-1, A14+Bayol+K$_2$CO$_3$+S2-1, A14+rapeseed oil, methyl ester, for example Edenor or Actirob+K$_2$CO$_3$+S2-1, A1+Solvesso+NaHCO$_3$+S2-1, A1+Bayol+NaHCO$_3$+S2-1, A1+rapeseed oil methyl ester, for example Edenor or Actirob+NaHCO$_3$+S2-1, A2+Solvesso+NaHCO$_3$+S2-1, A2+Bayol+NaHCO$_3$+S2-1, A2+rapeseed oil methyl ester, for example Edenor or Actirob+NaHCO$_3$+S2-1, A3+Solvesso+NaHCO$_3$+S2-1, A3+Bayol+NaHCO$_3$+S2-1, A3+rapeseed oil methyl ester, for example Edenor or Actirob+NaHCO$_3$+S2-1, A4+Solvesso+NaHCO$_3$+S2-1, A4+Bayol+NaHCO$_3$+S2-1, A4+rapeseed oil methyl ester, for example Edenor or Actirob+NaHCO$_3$+S2-1, A5+Solvesso+NaHCO$_3$+S2-1, A5+Bayol+NaHCO$_3$+S2-1, A5+rapeseed oil methyl ester, for example Edenor or Actirob+NaHCO$_3$+S2-1, A6+Solvesso+NaHCO$_3$+S2-1, A6+Bayol+NaHCO$_3$+S2-1, A6+rapeseed oil methyl ester, for example Edenor or Actirob+NaHCO$_3$+S2-1, A7+Solvesso+NaHCO$_3$+S2-1, A7+Bayol+NaHCO$_3$+S2-1, A7+rapeseed oil methyl ester, for example Edenor or Actirob+NaHCO$_3$+S2-1, A8+Solvesso+NaHCO$_3$+S2-1, A8+Bayol+NaHCO$_3$+S2-1, A8+rapeseed oil methyl ester, for example Edenor or Actirob+NaHCO$_3$+S2-1, A9+Solvesso+NaHCO$_3$+S2-1, A9+Bayol+NaHCO$_3$+S2-1, A9+rapeseed oil methyl ester, for example Edenor or Actirob+NaHCO$_3$+S2-1, A10+Solvesso+NaHCO$_3$+S2-1, A10+Bayol+NaHCO$_3$+S2-1, A10+rapeseed oil methyl ester, for example Edenor or Actirob+NaHCO$_3$+S2-1, A11+Solvesso+NaHCO$_3$+S2-1, A11+Bayol+NaHCO$_3$+S2-1, A11+rapeseed oil methyl ester, for example Edenor or Actirob+NaHCO$_3$+S2-1, A12+Solvesso+NaHCO$_3$+S2-1, A12+Bayol+NaHCO$_3$+S2-1, A12+rapeseed oil methyl ester, for example Edenor or Actirob+NaHCO$_3$+S2-1, A13+Solvesso+NaHCO$_3$+S2-1, A13+Bayol+NaHCO$_3$+S2-1, A13+rapeseed oil methyl ester, for example Edenor or Actirob+NaHCO$_3$+S2-1, A14+Solvesso+NaHCO$_3$+S2-1, A14+Bayol+NaHCO$_3$+S2-1, A14+rapeseed oil methyl ester, for example Edenor or Actirob+NaHCO$_3$+-S2-1, A1+Solvesso+KHCO$_3$+S2-1, A1+Bayol+KHCO$_3$+S2-1, A1+rapeseed oil methyl ester, for example Edenor or Actirob+KHCO$_3$+S2-1, A2+Solvesso+KHCO$_3$+S2-1, A2+Bayol+KHCO$_3$+S2-1, A2+rapeseed oil methyl ester, for example Edenor or Actirob+KHCO$_3$+S2-1, A3+Solvesso+KHCO$_3$+S2-1, A3+Bayol+KHCO$_3$+S2-1, A3+rapeseed oil methyl ester, for example Edenor or Actirob+KHCO$_3$+S2-1, A4+Solvesso+KHCO$_3$+S2-1, A4+Bayol+KHCO$_3$+S2-1, A4+rapeseed oil methyl ester, for example Edenor or Actirob+KHCO$_3$+S2-1, A5+Solvesso+KHCO$_3$+S2-1, A5+Bayol+KHCO$_3$+S2-1, A5+rapeseed oil methyl ester, for example Edenor or Actirob+KHCO$_3$+S2-1, A6+Solvesso+KHCO$_3$+S2-1, A6+Bayol+KHCO$_3$+S2-1, A6+rapeseed oil methyl ester, for example Edenor or Actirob+KHCO$_3$+S2-1, A7+Solvesso+KHCO$_3$+S2-1, A7+Bayol+KHCO$_3$+S2-1, A7+rapeseed oil methyl ester, for example Edenor or Actirob+KHCO$_3$+S2-1, A8+Solvesso+KHCO$_3$+S2-1, A8+Bayol+KHCO$_3$+S2-1, A8+rapeseed oil methyl ester, for example Edenor or Actirob+KHCO$_3$+S2-1, A9+Solvesso+KHCO$_3$+S2-1, A9+Bayol+KHCO$_3$+S2-1, A9+rapeseed oil methyl ester, for example Edenor or Actirob+KHCO$_3$+S2-1, A10+Solvesso+KHCO$_3$+S2-1, A10+Bayol+KHCO$_3$+S2-1, A10+rapeseed oil methyl ester, for example Edenor or Actirob+KHCO$_3$+S2-1, A11+Solvesso+KHCO$_3$+S2-1, A11+Bayol+KHCO$_3$+S2-1, A11+rapeseed oil methyl ester, for example Edenor or Actirob+KHCO$_3$+S2-1, A12+Solvesso+KHCO$_3$+S2-1, A12+Bayol+KHCO$_3$+S2-1, A12+rapeseed oil methyl ester, for example Edenor or Actirob+KHCO$_3$+S2-1, A13+Solvesso+KHCO$_3$+S2-1, A13+Bayol+KHCO$_3$+S2-1, A13+rapeseed oil methyl ester, for example Edenor or Actirob+KHCO$_3$+S2-1, A14+Solvesso+KHCO$_3$+S2-1, A14+Bayol+KHCO$_3$+S2-1, A14+rapeseed oil methyl ester, for example Edenor or Actirob+KHCO$_3$+S2-1;

A1+Solvesso+Na$_2$CO$_3$+sodium di(2-ethylhexyl)sulfosuccinate, A1+Bayol+Na$_2$CO$_3$+sodium di(2-ethylhexyl)sulfosuccinate, A1+rapeseed oil methyl ester, for example Edenor or Actirob+Na$_2$CO$_3$+sodium di(2-ethylhexyl)sulfosuccinate, A2+Solvesso+Na$_2$CO$_3$+sodium di(2-ethylhexyl)sulfosuccinate, A2+Bayol+Na$_2$CO$_3$+sodium di(2-ethylhexyl)sulfosuccinate, A2+rapeseed oil methyl ester, for example Edenor or Actirob+Na$_2$CO$_3$+sodium di(2-ethylhexyl)sulfosuccinate, A3+Solvesso+Na$_2$CO$_3$+sodium di(2-ethylhexyl)sulfosuccinate, A3+Bayol+Na$_2$CO$_3$+sodium di(2-ethylhexyl)sulfosuccinate, A3+rapeseed oil methyl ester, for example Edenor or Actirob+Na$_2$CO$_3$+sodium di(2-ethylhexyl)sulfosuccinate, A4+Solvesso+Na$_2$CO$_3$+sodium di(2-ethylhexyl)sulfosuccinate, A4+Bayol+Na$_2$CO$_3$+sodium di(2-ethylhexyl)sulfosuccinate, A4+rapeseed oil methyl ester, for example Edenor or Actirob+Na$_2$CO$_3$+sodium di(2-ethylhexyl)sulfosuccinate, A5+Solvesso+Na$_2$CO$_3$+sodium di(2-ethylhexyl)sulfosuccinate, A5+Bayol+Na$_2$CO$_3$+sodium di(2-ethylhexyl)sulfosuccinate, A5+rapeseed oil methyl ester, for example Edenor or Actirob+Na$_2$CO$_3$+sodium di(2-ethylhexyl)sulfosuccinate, A6+Solvesso+Na$_2$CO$_3$+sodium di(2-ethylhexyl)sulfosuccinate, A6+Bayol+Na$_2$CO$_3$+sodium di(2-ethylhexyl)sulfosuccinate, A6+rapeseed oil methyl ester, for example Edenor or Actirob+Na$_2$CO$_3$+sodium di(2-ethylhexyl)sulfosuccinate, A7+Solvesso+Na$_2$CO$_3$+sodium di(2-ethylhexyl)sulfosuccinate, A7+Bayol+Na$_2$CO$_3$ +sodium di(2-ethylhexyl)sulfosuccinate, A7+rapeseed oil methyl ester, for example Edenor or Actirob+Na$_2$CO$_3$+sodium di(2-ethylhexyl)sulfosuccinate, A8+Solvesso+Na$_2$CO$_3$+sodium di(2-ethylhexyl)sulfosuccinate, A8+Bayol+Na$_2$CO$_3$+sodium di(2-ethylhexyl)sulfosuccinate, A8+rapeseed oil methyl ester, for example Edenor or Actirob+Na$_2$CO$_3$+sodium di(2-ethylhexyl)sulfosuccinate, A9+Solvesso+Na$_2$CO$_3$+sodium di(2-ethylhexyl)sulfosuccinate, A9+Bayol+Na$_2$CO$_3$+sodium di(2-ethylhexyl)sulfosuccinate, A9+rapeseed oil methyl ester, for example Edenor or Actirob+Na$_2$CO$_3$+sodium di(2-ethylhexyl)sulfosuccinate, A10+Solvesso+Na$_2$CO$_3$+sodium di(2-ethylhexyl)sulfosuccinate, A10+Bayol+Na$_2$CO$_3$+sodium di(2-ethylhexyl)sulfosuccinate, A10+rapeseed oil methyl ester, for example Edenor or Actirob+Na$_2$CO$_3$+sodium di(2-ethylhexyl) sulfosuccinate, A11+Solvesso+Na$_2$CO$_3$+sodium di(2-ethylhexyl)sulfosuccinate, A11+Bayol+Na$_2$CO$_3$+sodium di(2-ethylhexyl)sulfosuccinate, A11+rapeseed oil methyl ester, for example Edenor or Actirob+Na$_2$CO$_3$+sodium di(2-ethylhexyl)sulfosuccinate, A12+Solvesso+Na$_2$CO$_3$+sodium di(2-ethylhexyl)sulfosuccinate, A12+Bayol+Na$_2$CO$_3$+sodium di(2-ethylhexyl)sulfosuccinate, A12+rapeseed oil methyl ester, for example Edenor or Actirob+Na$_2$CO$_3$+sodium di(2-ethylhexyl)sulfosuccinate, A13+Solvesso+Na$_2$CO$_3$+sodium di(2-ethylhexyl)sulfosuccinate, A13+Bayol+Na$_2$CO$_3$+sodium di(2-ethylhexyl)sulfosuccinate, A13+rapeseed oil methyl ester, for example Edenor or Actirob+Na$_2$CO$_3$+sodium di(2-ethylhexyl)sulfosuccinate, A14+Solvesso+Na$_2$CO$_3$+sodium di(2-ethylhexyl)sulfosuccinate, A14+Bayol+Na$_2$CO$_3$+sodium di(2-ethylhexyl)sulfosuccinate, A14+rapeseed oil methyl ester, for example Edenor or Actirob+Na$_2$CO$_3$+sodium di(2-ethylhexyl) sulfosuccinate, A1+Solvesso+K$_2$CO$_3$+sodium di(2-ethylhexyl)sulfosuccinate, A1+Bayol+K$_2$CO$_3$+sodium di(2-ethylhexyl)sulfosuccinate, A1+rapeseed oil methyl ester, for example Edenor or Actirob+K$_2$CO$_3$+sodium di(2-ethylhexyl)sulfosuccinate, A2+Solvesso+K$_2$CO$_3$+sodium di(2-ethylhexyl)sulfosuccinate, A2+Bayol+K$_2$CO$_3$+sodium di(2-ethylhexyl)sulfosuccinate, A2+rapeseed oil methyl ester, for example Edenor or Actirob+K$_2$CO$_3$+sodium di(2-ethylhexyl)sulfosuccinate, A3+Solvesso+K$_2$CO$_3$+sodium di(2-ethylhexyl)sulfosuccinate, A3+Bayol+K$_2$CO$_3$+sodium di(2-ethylhexyl)sulfosuccinate, A3+rapeseed oil methyl ester, for example Edenor or Actirob+K$_2$CO$_3$+sodium di(2-ethylhexyl)sulfosuccinate, A4+Solvesso+K$_2$CO$_3$+sodium di(2-ethylhexyl)sulfosuccinate, A4+Bayol+K$_2$CO$_3$+sodium di(2-ethylhexyl)sulfosuccinate, A4+rapeseed oil methyl ester, for example Edenor or Actirob+K$_2$CO$_3$+sodium di(2-ethylhexyl)sulfosuccinate, A5+Solvesso+K$_2$CO$_3$+sodium di(2-ethylhexyl)sulfosuccinate, A5+Bayol+K$_2$CO$_3$+sodium di(2-ethylhexyl)sulfosuccinate, A5+rapeseed oil methyl ester, for example Edenor or Actirob+K$_2$CO$_3$+sodium di(2-ethylhexyl)sulfosuccinate, A6+Solvesso+K$_2$CO$_3$+sodium di(2-ethylhexyl)sulfosuccinate, A6+Bayol+K$_2$CO$_3$+sodium di(2-ethylhexyl)sulfosuccinate, A6+rapeseed oil methyl ester, for example Edenor or Actirob+K$_2$CO$_3$+sodium di(2-ethylhexyl)sulfosuccinate, A7+Solvesso+K$_2$CO$_3$+sodium di(2-ethylhexyl)sulfosuccinate, A7+Bayol+K$_2$CO$_3$+sodium di(2-ethylhexyl)sulfosuccinate, A7+rapeseed oil methyl ester, for example Edenor or Actirob+K$_2$CO$_3$+sodium di(2-ethylhexyl)sulfosuccinate, A8+Solvesso+K$_2$CO$_3$+sodium di(2-ethylhexyl)sulfosuccinate, A8+Bayol+K$_2$CO$_3$+sodium di(2-ethylhexyl)sulfosuccinate, A8+rapeseed oil methyl ester, for example Edenor or Actirob+K$_2$CO$_3$+sodium di(2-ethylhexyl)sulfosuccinate, A9+Solvesso+K$_2$CO$_3$+sodium di(2-ethylhexyl)sulfosuccinate, A9+Bayol+K$_2$CO$_3$+sodium di(2-ethylhexyl)sulfosuccinate, A9+rapeseed oil methyl ester, for example Edenor or Actirob+K$_2$CO$_3$+sodium di(2-ethylhexyl)sulfosuccinate, A10+Solvesso+K$_2$CO$_3$+sodium di(2-ethylhexyl)sulfosuccinate, A10+Bayol+K$_2$CO$_3$+sodium di(2-ethylhexyl)sulfosuccinate, A10+rapeseed oil methyl ester, for example Edenor or Actirob+K$_2$CO$_3$+sodium di(2-ethylhexyl)sulfosuccinate, A11+Solvesso+K$_2$CO$_3$+sodium di(2-ethylhexyl)sulfosuccinate, A11+Bayol+K$_2$CO$_3$+sodium di(2-ethylhexyl)sulfosuccinate, A11+rapeseed oil methyl ester, for example Edenor or Actirob+K$_2$CO$_3$+sodium di(2-ethylhexyl)sulfosuccinate, A12+Solvesso+K$_2$CO$_3$+sodium di(2-ethylhexyl)sulfosuccinate, A12+Bayol+K$_2$CO$_3$+sodium di(2-ethylhexyl)sulfosuccinate, A12+rapeseed oil methyl ester, for example Edenor or Actirob+K$_2$CO$_3$+sodium di(2-ethylhexyl)sulfosuccinate, A13+Solvesso+K$_2$CO$_3$+sodium di(2-ethylhexyl)sulfosuccinate, A13+Bayol+K$_2$CO$_3$+sodium di(2-ethylhexyl)sulfosuccinate, A13+rapeseed oil methyl ester, for example Edenor or Actirob+K$_2$CO$_3$+sodium di(2-ethylhexyl)sulfosuccinate, A14+Solvesso+K$_2$CO$_3$+sodium di(2-ethylhexyl)sulfosuccinate, A14+Bayol+K$_2$CO$_3$+sodium di(2-ethylhexyl)sulfosuccinate, A14+rapeseed oil methyl ester, for example Edenor or Actirob+K$_2$CO$_3$+sodium di(2-ethylhexyl)sulfosuccinate, A1+Solvesso+NaHCO$_3$+sodium di(2-ethylhexyl)sulfosuccinate, A1+Bayol+NaHCO$_3$+sodium di(2-ethylhexyl)sulfosuccinate, A1+rapeseed oil methyl ester, for example Edenor or Actirob+NaHCO$_3$+sodium di(2-ethylhexyl)sulfosuccinate, A2+Solvesso+NaHCO$_3$+sodium di(2-ethylhexyl)sulfosuccinate, A2+Bayol+NaHCO$_3$+sodium di(2-ethylhexyl)sulfosuccinate, A2+rapeseed oil methyl ester, for example Edenor or Actirob+NaHCO$_3$+sodium di(2-ethylhexyl)sulfosuccinate, A3+Solvesso+NaHCO$_3$+sodium di(2-ethylhexyl)sulfosuccinate, A3+Bayol+NaHCO$_3$+sodium di(2-ethylhexyl)sulfosuccinate, A3+rapeseed oil methyl ester, for example Edenor or Actirob+NaHCO$_3$+sodium di(2-ethylhexyl)sulfosuccinate, A4+Solvesso+NaHCO$_3$+sodium di(2-ethylhexyl)sulfosuccinate, A4+Bayol+NaHCO$_3$+sodium di(2-ethylhexyl) sulfosuccinate, A4+rapeseed oil methyl ester, for example Edenor or Actirob+NaHCO$_3$+sodium di(2-ethylhexyl)sulfosuccinate, A5+Solvesso+NaHCO$_3$+sodium di(2-ethylhexyl) sulfosuccinate, A5+Bayol+NaHCO$_3$+sodium di(2-ethylhexyl)sulfosuccinate, A5+rapeseed oil methyl ester, for example Edenor or Actirob+NaHCO$_3$+sodium di(2-ethylhexyl)sulfosuccinate, A6+Solvesso+NaHCO$_3$+sodium di(2-ethylhexyl)sulfosuccinate, A6+Bayol+NaHCO$_3$+sodium di(2-ethylhexyl)sulfosuccinate, A6+rapeseed oil methyl ester, for example Edenor or Actirob+NaHCO$_3$+sodium di(2-ethylhexyl)sulfosuccinate, A7+Solvesso+NaHCO$_3$+sodium di(2-ethylhexyl)sulfosuccinate, A7+Bayol+NaHCO$_3$+sodium di(2-ethylhexyl)sulfosuccinate, A7+rapeseed oil methyl ester, for example Edenor or Actirob+NaHCO$_3$+sodium di(2-ethylhexyl)sulfosuccinate, A8+Solvesso+NaHCO$_3$+sodium di(2-ethylhexyl)sulfosuccinate, A8+Bayol+NaHCO$_3$+sodium di(2-ethylhexyl)sulfosuccinate, A8+rapeseed oil methyl ester, for example Edenor or Actirob+NaHCO$_3$+sodium di(2-ethylhexyl)sulfosuccinate, A9+Solvesso+NaHCO$_3$+sodium di(2-ethylhexyl)sulfosuccinate, A9+Bayol+NaHCO$_3$+sodium di(2-ethylhexyl)sulfosuccinate, A9+rapeseed oil methyl ester, for example Edenor or Actirob+NaHCO$_3$+sodium di(2-ethylhexyl)sulfosuccinate, A10+Solvesso+NaHCO$_3$+sodium di(2-ethylhexyl)sulfosuccinate, A10+Bayol+NaHCO$_3$+sodium di(2-ethylhexyl) sulfosuccinate, A10+rapeseed oil methyl ester, for example Edenor or Actirob+NaHCO$_3$+sodium di(2-ethylhexyl)sulfosuccinate, A11+Solvesso+NaHCO$_3$+sodium di(2-ethylhexyl)sulfosuccinate, A11+Bayol+NaHCO$_3$+sodium di(2-ethylhexyl)sulfosuccinate, A11+rapeseed oil methyl ester, for example Edenor or Actirob+NaHCO$_3$+sodium di(2-ethylhexyl)sulfosuccinate, A12+Solvesso+NaHCO$_3$+sodium di(2-ethylhexyl)sulfosuccinate, A12+Bayol+NaHCO₃+sodium di(2-ethylhexyl)sulfosuccinate, A12+rapeseed oil methyl ester, for example Edenor or Actirob+NaHCO₃+sodium di(2-ethylhexyl)sulfosuccinate, A13+Solvesso+NaHCO₃+sodium di(2-ethylhexyl)sulfosuccinate, A13+Bayol+NaHCO₃+sodium di(2-ethylhexyl)sulfosuccinate, A13+rapeseed oil methyl ester, for example Edenor or Actirob+NaHCO₃+sodium di(2-ethylhexyl)sulfosuccinate, A14+Solvesso+NaHCO₃+sodium di(2-ethylhexyl)sulfosuccinate, A14+Bayol+NaHCO₃+sodium di(2-ethylhexyl)sulfosuccinate, A14+rapeseed oil methyl ester, for example Edenor or Actirob+NaHCO₃+sodium di(2-ethylhexyl)sulfosuccinate, A1+Solvesso+KHCO₃+sodium di(2-ethylhexyl)sulfosuccinate, A1+Bayol+KHCO₃+sodium di(2-ethylhexyl)sulfosuccinate, A1+rapeseed oil methyl ester, for example Edenor or Actirob+KHCO₃+sodium di(2-ethylhexyl)sulfosuccinate, A2+Solvesso+KHCO₃+sodium di(2-ethylhexyl)sulfosuccinate, A2+Bayol+KHCO₃+sodium di(2-ethylhexyl)sulfosuccinate, A2+rapeseed oil methyl ester, for example Edenor or Actirob+KHCO₃+sodium di(2-ethylhexyl)sulfosuccinate,. A3+Solvesso+KHCO₃+sodium di(2-ethylhexyl)sulfosuccinate, A3+Bayol+KHCO₃+sodium di(2-ethylhexyl)sulfosuccinate, A3+rapeseed oil methyl ester, for example Edenor or Actirob+KHCO₃+sodium di(2-ethylhexyl)sulfosuccinate, A4+Solvesso+KHCO₃+sodium di(2-ethylhexyl)sulfosuccinate, A4+Bayol+KHCO₃+sodium di(2-ethylhexyl)sulfosuccinate, A4+rapeseed oil methyl ester, for example Edenor or Actirob+KHCO₃+sodium di(2-ethylhexyl)sulfosuccinate, A5+Solvesso+KHCO₃+sodium di(2-ethylhexyl)sulfosuccinate, A5+Bayol+KHCO₃+sodium di(2-ethylhexyl)sulfosuccinate, A5+rapeseed oil methyl ester, for example Edenor or Actirob+KHCO₃+sodium di(2-ethylhexyl)sulfosuccinate, A6+Solvesso+KHCO₃+sodium di(2-ethylhexyl)sulfosuccinate, A6+Bayol+KHCO₃+sodium di(2-ethylhexyl)sulfosuccinate, A6+rapeseed oil methyl ester, for example Edenor or Actirob+KHCO₃+sodium di(2-ethylhexyl)sulfosuccinate, A7+Solvesso+KHCO₃+sodium di(2-ethylhexyl)sulfosuccinate, A7+Bayol+KHCO₃+sodium di(2-ethylhexyl)sulfosuccinate, A7+rapeseed oil methyl ester, for example Edenor or Actirob+KHCO₃+sodium di(2-ethylhexyl)sulfosuccinate, A8+Solvesso+KHCO₃+sodium di(2-ethylhexyl)sulfosuccinate, A8+Bayol+KHCO₃+sodium di(2-ethylhexyl)sulfosuccinate, A8+rapeseed oil methyl ester, for example Edenor or Actirob+KHCO₃+sodium di(2-ethylhexyl)sulfosuccinate, A9+Solvesso+KHCO₃+sodium di(2-ethylhexyl)sulfosuccinate, A9+Bayol+KHCO₃+sodium di(2-ethylhexyl)sulfosuccinate, A9+rapeseed oil methyl ester, for example Edenor or Actirob+KHCO₃+sodium di(2-ethylhexyl)sulfosuccinate, A10+Solvesso+KHCO₃+sodium di(2-ethylhexyl)sulfosuccinate, A10+Bayol+KHCO₃+sodium di(2-ethylhexyl)sulfosuccinate, A10+rapeseed oil methyl ester, for example Edenor or Actirob+KHCO₃+sodium di(2-ethylhexyl)sulfosuccinate, A11+Solvesso+KHCO₃+sodium di(2-ethylhexyl)sulfosuccinate, A11+Bayol+KHCO₃+sodium di(2-ethylhexyl)sulfosuccinate, A11+rapeseed oil methyl ester, for example Edenor or Actirob+KHCO₃+sodium di(2-ethylhexyl)sulfosuccinate, A12+Solvesso+KHCO₃+sodium di(2-ethylhexyl)sulfosuccinate, A12+Bayol+KHCO₃+sodium di(2-ethylhexyl)sulfosuccinate, A12+rapeseed oil methyl ester, for example Edenor or Actirob+KHCO₃+sodium di(2-ethylhexyl)sulfosuccinate, A13+Solvesso+KHCO₃+sodium di(2-ethylhexyl)sulfosuccinate, A13+Bayol+KHCO₃+sodium di(2-ethylhexyl)sulfosuccinate, A13+rapeseed oil methyl ester, for example Edenor or Actirob+KHCO₃+sodium di(2-ethylhexyl)sulfosuccinate, A14+Solvesso+KHCO₃+sodium di(2-ethylhexyl)sulfosuccinate, A14+Bayol+KHCO₃+sodium di(2-ethylhexyl)sulfosuccinate, A14+rapeseed oil methyl ester, for example Edenor or Actirob+KHCO₃+sodium di(2-ethylhexyl)sulfosuccinate;

A1+Solvesso+Na₂CO₃+S1-1+sodium di(2-ethylhexyl)sulfosuccinate, A1+Bayol+Na₂CO₃+S1-1+sodium di(2-ethylhexyl)sulfosuccinate, A1+rapeseed oil methyl ester, for example Edenor or Actirob+Na₂CO₃+S1-1+sodium di(2-ethylhexyl)sulfosuccinate, A2+Solvesso+Na₂CO₃+S1-1+sodium di(2-ethylhexyl)sulfosuccinate, A2+Bayol+Na₂CO₃+S1-1+sodium di(2-ethylhexyl)sulfosuccinate, A2+rapeseed oil methyl ester, for example Edenor or Actirob+Na₂CO₃+S1-1+sodium di(2-ethylhexyl)sulfosuccinate, A3+Solvesso+Na₂CO₃+S1-1+sodium di(2-ethylhexyl)sulfosuccinate, A3+Bayol+Na₂CO₃+S1-1+sodium di(2-ethylhexyl)sulfosuccinate, A3+rapeseed oil methyl ester, for example Edenor or Actirob+Na₂CO₃+S1-1+sodium di(2-ethylhexyl)sulfosuccinate, A4+Solvesso+Na₂CO₃+S1-1+sodium di(2-ethylhexyl)sulfosuccinate, A4+Bayol+Na₂CO₃+S1-1+sodium di(2-ethylhexyl)sulfosuccinate, A4+rapeseed oil methyl ester, for example Edenor or Actirob+Na₂CO₃+S1-1+sodium di(2-ethylhexyl)sulfosuccinate, A5+Solvesso+Na₂CO₃+S1-1+sodium di(2-ethylhexyl)sulfosuccinate, A5+Bayol+Na₂CO₃+S1-1+sodium di(2-ethylhexyl)sulfosuccinate, A5+rapeseed oil methyl ester, for example Edenor or Actirob+Na₂CO₃+S1-1+sodium di(2-ethylhexyl)sulfosuccinate, A6+Solvesso+Na₂CO₃+S1-1+sodium di(2-ethylhexyl)sulfosuccinate, A6+Bayol+Na₂CO₃+S1-1+sodium di(2-ethylhexyl)sulfosuccinate, A6+rapeseed oil methyl ester, for example Edenor or Actirob+Na₂CO₃+S1-1+sodium di(2-ethylhexyl)sulfosuccinate, A7+Solvesso+Na₂CO₃+S1-1+sodium di(2-ethylhexyl)sulfosuccinate, A7+Bayol+Na₂CO₃+S1-1+sodium di(2-ethylhexyl)sulfosuccinate, A7+rapeseed oil methyl ester, for example Edenor or Actirob+Na₂CO₃+S1-1+sodium di(2-ethylhexyl)sulfosuccinate, A8+Solvesso+Na₂CO₃+S1-1+sodium di(2-ethylhexyl)sulfosuccinate, A8+Bayol+Na₂CO₃+S1-1+sodium di(2-ethylhexyl)sulfosuccinate, A8+rapeseed oil methyl ester, for example Edenor or Actirob+Na₂CO₃+S1-1+sodium di(2-ethylhexyl)sulfosuccinate, A9+Solvesso+Na₂CO₃+S1-1+sodium di(2-ethylhexyl)sulfosuccinate, A9+Bayol+Na₂CO₃+S1-1+sodium di(2-ethylhexyl)sulfosuccinate, A9+rapeseed oil methyl ester, for example Edenor or Actirob+Na₂CO₃+S1-1+sodium di(2-ethylhexyl)sulfosuccinate, A10+Solvesso+Na₂CO₃+S1-1+sodium di(2-ethylhexyl)sulfosuccinate, A10+Bayol+Na₂CO₃+S1-1+sodium di(2-ethylhexyl)sulfosuccinate, A10+rapeseed oil methyl ester, for example Edenor or Actirob+Na₂CO₃+S1-1+sodium di(2-ethylhexyl)sulfosuccinate, A11+Solvesso+Na₂CO₃+S1-1+sodium di(2-ethylhexyl)sulfosuccinate, A11+Bayol+Na₂CO₃+S1-1+sodium di(2-ethylhexyl)sulfosuccinate, A11+rapeseed oil methyl ester, for example Edenor or Actirob+Na₂CO₃+S1-1+sodium di(2-ethylhexyl)sulfosuccinate, A12+Solvesso+Na₂CO₃+S1-1+sodium di(2-ethylhexyl)sulfosuccinate, A12+Bayol+Na₂CO₃+S1-1+sodium di(2-ethylhexyl)sulfosuccinate, A12+rapeseed oil methyl ester, for example Edenor or Actirob+Na₂CO₃+S1-1+sodium di(2-ethylhexyl)sulfosuccinate, A13+Solvesso+Na₂CO₃+S1-1+sodium di(2-ethylhexyl)sulfosuccinate, A13+Bayol+Na₂CO₃+S1-1+sodium di(2-ethylhexyl)sulfosuccinate, A13+rapeseed oil methyl ester, for example Edenor or Actirob+Na₂CO₃+S1-1+sodium di(2-ethylhexyl)sulfosuccinate, A14+Solvesso+Na₂CO₃+S1-1+sodium di(2-ethylhexyl)sulfosuccinate, A14+Bayol+Na₂CO₃+S1-1+sodium di(2-ethylhexyl)sulfosuccinate, A14+rapeseed oil methyl ester, for example Edenor or Actirob+Na₂CO₃+S1-1+sodium di(2-ethylhexyl)sulfosuccinate, A1+Solvesso+K₂CO₃+S1-1+sodium di(2-ethylhexyl)sulfosuccinate, A1+Bayol+K₂CO₃+S1-1+sodium di(2-ethylhexyl)sulfosuccinate, A1+rapeseed oil methyl ester, for example Edenor or Actirob+K₂CO₃+S1-1+sodium di(2-ethylhexyl)sulfosuccinate, A2+Solvesso+K₂CO₃+S1-1+sodium di(2-ethylhexyl)sulfosuccinate, A2+Bayol+K₂CO₃+S1-1+sodium di(2-ethylhexyl)sulfosuccinate, A2+rapeseed oil methyl ester, for example Edenor or Actirob+K₂CO₃+S1-1+sodium di(2-ethylhexyl)sulfosuccinate, A3+Solvesso+K₂CO₃+S1-1+sodium di(2-ethylhexyl)sulfosuccinate, A3+Bayol+K₂CO₃+S1-1+sodium di(2-ethylhexyl)sulfosuccinate, A3+rapeseed oil methyl ester, for example Edenor or Actirob+K₂CO₃+S1-1+sodium di(2-ethylhexyl)sulfosuccinate, A4+Solvesso+K₂CO₃+S1-1+sodium di(2-ethylhexyl)sulfosuccinate, A4+Bayol+K₂CO₃+S1-1+sodium di(2-ethylhexyl)sulfosuccinate, A4+rapeseed oil methyl ester, for example Edenor or Actirob+K₂CO₃+S1-1+sodium di(2-ethylhexyl)sulfosuccinate, A5+Solvesso+K₂CO₃+S1-1+sodium di(2-ethylhexyl)sulfosuccinate, A5+Bayol+K₂CO₃+S1-1+sodium di(2-ethylhexyl)sulfosuccinate, A5+rapeseed oil methyl ester, for example Edenor or Actirob+K₂CO₃+S1-1+sodium di(2-ethylhexyl)sulfosuccinate, A6+Solvesso+K₂CO₃+S1-1+sodium di(2-ethylhexyl)sulfosuccinate, A6+Bayol+K₂CO₃+S1-1+sodium di(2-ethylhexyl)sulfosuccinate, A6+rapeseed oil methyl ester, for example Edenor or Actirob+K₂CO₃+S1-1+sodium di(2-ethylhexyl)sulfosuccinate, A7+Solvesso+K₂CO₃+S1-1+sodium di(2-ethylhexyl)sulfosuccinate, A7+Bayol+K₂CO₃+S1-1+sodium di(2-ethylhexyl)sulfosuccinate, A7+rapeseed oil methyl ester, for example Edenor or Actirob+K₂CO₃+S1-1+sodium di(2-ethylhexyl)sulfosuccinate, A8+Solvesso+K₂CO₃+S1-1+sodium di(2-ethylhexyl)sulfosuccinate, A8+Bayol+K₂CO₃+S1-1+sodium di(2-ethylhexyl)sulfosuccinate, A8+rapeseed oil methyl ester, for example Edenor or Actirob+K₂CO₃+S1-1+sodium di(2-ethylhexyl)sulfosuccinate, A9+Solvesso+K₂CO₃+S1-1+sodium di(2-ethylhexyl)sulfosuccinate, A9+Bayol+K₂CO₃+S1-1+sodium di(2-ethylhexyl)sulfosuccinate, A9+rapeseed oil methyl ester, for example Edenor or Actirob+K₂CO₃+S1-1+sodium di(2-ethylhexyl)sulfosuccinate, A10+Solvesso+K₂CO₃+S1-1+sodium di(2-ethylhexyl)sulfosuccinate, A10+Bayol+K₂CO₃+S1-1+sodium di(2-ethylhexyl)sulfosuccinate, A10+rapeseed oil methyl ester, for example Edenor or Actirob+K₂CO₃+S1-1+sodium di(2-ethylhexyl)sulfosuccinate, A11+Solvesso+K₂CO₃+S1-1+sodium di(2-ethylhexyl)sulfosuccinate, A11+Bayol+K₂CO₃+S1-1+sodium di(2-ethylhexyl)sulfosuccinate, A11+rapeseed oil methyl ester, for example Edenor or Actirob+K₂CO₃+S1-1+sodium di(2-ethylhexyl)sulfosuccinate, A12+Solvesso+K₂CO₃+S1-1+sodium di(2-ethylhexyl)sulfosuccinate, A12+Bayol+K₂CO₃+S1-1+sodium di(2-ethylhexyl)sulfosuccinate, A12+rapeseed oil methyl ester, for example Edenor or Actirob+K₂CO₃+S1-1+sodium di(2-ethylhexyl)sulfosuccinate, A13+Solvesso+K₂CO₃+S1-1+sodium di(2-ethylhexyl)sulfosuccinate, A13+Bayol+K₂CO₃+S1-1+sodium di(2-ethylhexyl)sulfosuccinate, A13+rapeseed oil methyl ester, for example Edenor or Actirob+K₂CO₃+S1-1+sodium di(2-ethylhexyl)sulfosuccinate, A14+Solvesso+K₂CO₃+S1-1+sodium di(2-ethylhexyl)sulfosuccinate, A14+Bayol+K₂CO₃+S1-1+sodium di(2-ethylhexyl)sulfosuccinate, A14+rapeseed oil methyl ester, for example Edenor or Actirob+K₂CO₃+S1-1+sodium di(2-ethylhexyl)sulfosuccinate, A1+Solvesso+NaHCO₃+S1-1+sodium di(2-ethylhexyl)sulfosuccinate, A1+Bayol+NaHCO₃+S1-1+sodium di(2-ethylhexyl)sulfosuccinate, A1+rapeseed oil methyl ester, for example Edenor or Actirob+NaHCO₃+S1-1+sodium di(2-ethylhexyl)sulfosuccinate, A2+Solvesso+NaHCO₃+S1-1+sodium di(2-ethylhexyl)sulfosuccinate, A2+Bayol+NaHCO₃+S1-1+sodium di(2-ethylhexyl)sulfosuccinate, A2+rapeseed oil methyl ester, for example Edenor or Actirob+NaHCO₃+S1-1+sodium di(2-ethylhexyl)sulfosuccinate, A3+Solvesso+NaHCO₃+S1-1+sodium di(2-ethylhexyl)sulfosuccinate, A3+Bayol+NaHCO₃+S1-1+sodium di(2-ethylhexyl)sulfosuccinate, A3+rapeseed oil methyl ester, for example Edenor or Actirob+NaHCO₃+S1-1+sodium di(2-ethylhexyl)sulfosuccinate, A4+Solvesso+NaHCO₃+S1-1+sodium di(2-ethylhexyl)sulfosuccinate, A4+Bayol+NaHCO₃+S1-1+sodium di(2-ethylhexyl)sulfosuccinate, A4+rapeseed oil methyl ester, for example Edenor or Actirob+NaHCO₃+S1-1+sodium di(2-ethylhexyl)sulfosuccinate, A5+Solvesso+NaHCO₃+S1-1+sodium di(2-ethylhexyl)sulfosuccinate, A5+Bayol+NaHCO₃+S1-1+sodium di(2-ethylhexyl)sulfosuccinate, A5+rapeseed oil methyl ester, for example Edenor or Actirob+NaHCO₃+S1-1+sodium di(2-ethylhexyl)sulfosuccinate, A6+Solvesso+NaHCO₃+S1-1+sodium di(2-ethylhexyl)sulfosuccinate, A6+Bayol+NaHCO₃+S1-1+sodium di(2-ethylhexyl)sulfosuccinate, A6+rapeseed oil methyl ester, for example Edenor or Actirob+NaHCO₃+S1-1+sodium di(2-ethylhexyl)sulfosuccinate, A7+Solvesso+NaHCO₃+S1-1+sodium di(2-ethylhexyl)sulfosuccinate, A7+Bayol+NaHCO₃+S1-1+sodium di(2-ethylhexyl)sulfosuccinate, A7+rapeseed oil methyl ester, for example Edenor or Actirob+NaHCO₃+S1-1+sodium di(2-ethylhexyl)sulfosuccinate, A8+Solvesso+NaHCO₃+S1-1+sodium di(2-ethylhexyl)sulfosuccinate, A8+Bayol+NaHCO₃+S1-1+sodium di(2-ethylhexyl)sulfosuccinate, A8+rapeseed oil methyl ester, for example Edenor or Actirob+NaHCO₃+S1-1+sodium di(2-ethylhexyl)sulfosuccinate, A9+Solvesso+NaHCO₃+S1-1+sodium di(2-ethylhexyl)sulfosuccinate, A9+Bayol+NaHCO₃+S1-1+sodium di(2-ethylhexyl)sulfosuccinate, A9+rapeseed oil methyl ester, for example Edenor or Actirob+NaHCO₃+S1-1+sodium di(2-ethylhexyl)sulfosuccinate, A10+Solvesso+NaHCO₃+S1-1+sodium di(2-ethylhexyl)sulfosuccinate, A10+Bayol+NaHCO₃+S1-1+sodium di(2-ethylhexyl)sulfosuccinate, A10+rapeseed oil methyl ester, for example Edenor or Actirob+NaHCO₃+S1-1+sodium di(2-ethylhexyl)sulfosuccinate, A11+Solvesso+NaHCO₃+S1-1+sodium di(2-ethylhexyl)sulfosuccinate, A11+Bayol+NaHCO₃+S1-1+sodium-di(2-ethylhexyl)sulfosuccinate, A11+rapeseed oil methyl ester, for example Edenor or Actirob+NaHCO₃+S1-1+sodium di(2-ethylhexyl)sulfosuccinate, A12+Solvesso+NaHCO₃+S1-1+sodium di(2-ethylhexyl)sulfosuccinate, A12+Bayol+NaHCO₃+S1-1+sodium di(2-ethylhexyl)sulfosuccinate, A12+rapeseed oil methyl ester, for example Edenor or Actirob+NaHCO₃+S1-1+sodium di(2-ethylhexyl)sulfosuccinate, A13+Solvesso+NaHCO₃+S1-1+sodium di(2-ethylhexyl)sulfosuccinate, A13+Bayol+NaHCO₃+S1-1+sodium di(2-ethylhexyl)sulfosuccinate, A13+rapeseed oil methyl ester, for example Edenor or Actirob+NaHCO₃+S1-1+sodium di(2-ethylhexyl)sulfosuccinate, A14+Solvesso+NaHCO₃+S1-1+sodium di(2-ethylhexyl)sulfosuccinate, A14+Bayol+NaHCO₃+S1-1+sodium di(2-ethylhexyl)sulfosuccinate, A14+rapeseed oil methyl ester, for example Edenor or Actirob+NaHCO₃+S1-1+sodium di(2-ethylhexyl)sulfosuccinate, A1+Solvesso+KHCO₃+S1-1+sodium di(2-ethylhexyl)sulfosuccinate, A1+Bayol+KHCO₃+S1-1+sodium di(2-ethylhexyl)sulfosuccinate, A1+rapeseed oil methyl ester, for example Edenor or Actirob+KHCO₃+S1-1+sodium di(2-ethylhexyl)sulfosuccinate, A2+Solvesso+KHCO₃+S1-1+sodium di(2-ethylhexyl)sulfosuccinate, A2+Bayol+KHCO₃+S1-1+sodium di(2-ethylhexyl)sulfosuccinate, A2+rapeseed oil methyl ester, for example Edenor or Actirob+KHCO₃+S1-1+sodium di(2-ethylhexyl)sulfosuccinate, A3+Solvesso+KHCO₃+S1-1+sodium di(2-ethylhexyl)sulfosuccinate, A3+Bayol+KHCO₃+S1-1+sodium di(2-ethylhexyl)sulfosuccinate, A3+rapeseed oil methyl ester, for example Edenor or Actirob+KHCO$_3$+S1-1+sodium di(2-ethylhexyl)sulfosuccinate, A4+Solvesso+KHCO$_3$+S1-1+sodium di(2-ethylhexyl)sulfosuccinate, A4+Bayol+KHCO$_3$+S1-1+sodium di(2-ethylhexyl)sulfosuccinate, A4+rapeseed oil methyl ester, for example Edenor or Actirob+KHCO$_3$+S1-1+sodium di(2-ethylhexyl)sulfosuccinate, A5+Solvesso+KHCO$_3$+S1-1+sodium di(2-ethylhexyl)sulfosuccinate, A5+Bayol+KHCO$_3$+S1-1+sodium di(2-ethylhexyl)sulfosuccinate, A5+rapeseed oil methyl ester, for example Edenor or Actirob+KHCO$_3$+S1-1+sodium di(2-ethylhexyl)sulfosuccinate, A6+Solvesso+KHCO$_3$+S1-1+sodium di(2-ethylhexyl)sulfosuccinate, A6+Bayol+KHCO$_3$+S1-1+sodium di(2-ethylhexyl)sulfosuccinate, A6+rapeseed oil methyl ester, for example Edenor or Actirob+KHCO$_3$+S1-1+sodium di(2-ethyl hexyl)sulfosuccinate, A7+Solvesso+KHCO$_3$+S1-1+sodium di(2-ethylhexyl)sulfosuccinate, A7+Bayol+KHCO$_3$+S1-1+sodium di(2-ethylhexyl)sulfosuccinate, A7+rapeseed oil methyl ester, for example Edenor or Actirob+KHCO$_3$+S1-1+sodium di(2-ethylhexyl)sulfosuccinate, A8+Solvesso+KHCO$_3$+S1-1+sodium di(2-ethylhexyl)sulfosuccinate, A8+Bayol+KHCO$_3$+S1-1+sodium di(2-ethylhexyl)sulfosuccinate, A8+rapeseed oil methyl ester, for example Edenor or Actirob+KHCO$_3$+S1-1+sodium di(2-ethylhexyl)sulfosuccinate, A9+Solvesso+KHCO$_3$+S1-1+sodium di(2-ethylhexyl)sulfosuccinate, A9+Bayol+KHCO$_3$+S1-1+sodium di(2-ethylhexyl)sulfosuccinate, A9+rapeseed oil methyl ester, for example Edenor or Actirob+KHCO$_3$+S1-1+sodium di(2-ethylhexyl)sulfosuccinate, A10+Solvesso+KHCO$_3$+S1-1+sodium di(2-ethylhexyl)sulfosuccinate, A10+Bayol+KHCO$_3$+S1-1+sodium di(2-ethylhexyl)sulfosuccinate, A10+rapeseed oil methyl ester, for example Edenor or Actirob+KHCO$_3$+S1-1+sodium di(2-ethylhexyl)sulfosuccinate, A11+Solvesso+KHCO$_3$+S1-1+sodium di(2-ethylhexyl)sulfosuccinate, A11+Bayol+KHCO$_3$+S1-1+sodium di(2-ethylhexyl)sulfosuccinate, A11+rapeseed oil methyl ester, for example Edenor or Actirob+KHCO$_3$+S1-1+sodium di(2-ethylhexyl)sulfosuccinate, A12+Solvesso+KHCO$_3$+S1-1+sodium di(2-ethylhexyl)sulfosuccinate, A12+Bayol+KHCO$_3$+S1-1+sodium di(2-ethylhexyl)sulfosuccinate, A12+rapeseed oil methyl ester, for example Edenor or Actirob+KHCO$_3$+S1-1+sodium di(2-ethylhexyl)sulfosuccinate, A13+Solvesso+KHCO$_3$+S1-1+sodium di(2-ethylhexyl)sulfosuccinate, A13+Bayol+KHCO$_3$+S1-1+sodium di(2-ethylhexyl)sulfosuccinate, A13+rapeseed oil methyl ester, for example Edenor or Actirob+KHCO$_3$+S1-1+sodium di(2-ethylhexyl)sulfosuccinate, A14+Solvesso+KHCO$_3$+S1-1+sodium di(2-ethylhexyl)sulfosuccinate, A14+Bayol+KHCO$_3$+S1-1+sodium di(2-ethylhexyl)sulfosuccinate, A14+rapeseed oil methyl ester, for example Edenor or Actirob+KHCO$_3$+S1-1+sodium di(2-ethylhexyl)sulfosuccinate;

A1+Solvesso+Na$_2$CO$_3$+S1-9+sodium di(2-ethylhexyl)sulfosuccinate, A1+Bayol+Na$_2$CO$_3$+S1-9+sodium di(2-ethylhexyl)sulfosuccinate, A1+rapeseed oil methyl ester, for example Edenor or Actirob+Na$_2$CO$_3$+S1-9+sodium di(2-ethylhexyl)sulfosuccinate, A2+Solvesso+Na$_2$CO$_3$+S1-9+sodium di(2-ethylhexyl)sulfosuccinate, A2+Bayol+Na$_2$CO$_3$+S1-9+sodium di(2-ethylhexyl)sulfosuccinate, A2+rapeseed oil methyl ester, for example Edenor or Actirob+Na$_2$CO$_3$+S1-9+sodium di(2-ethylhexyl)sulfosuccinate, A3+Solvesso+Na$_2$CO$_3$+S1-9+sodium di(2-ethylhexyl)sulfosuccinate, A3+Bayol+Na$_2$CO$_3$+S1-9+sodium di(2-ethylhexyl)sulfosuccinate, A3+rapeseed oil methyl ester, for example Edenor or Actirob+Na$_2$CO$_3$+S1-9+sodium di(2-ethylhexyl)sulfosuccinate, A4+Solvesso+Na$_2$CO$_3$+S1-9+sodium di(2-ethylhexyl)sulfosuccinate, A4+Bayol+Na$_2$CO$_3$+S1-9+sodium di(2-ethylhexyl)sulfosuccinate, A4+rapeseed oil methyl ester, for example Edenor or Actirob+Na$_2$CO$_3$+S1-9+sodium di(2-ethylhexyl)sulfosuccinate, A5+Solvesso+Na$_2$CO$_3$+S1-9+sodium di(2-ethylhexyl)sulfosuccinate, A5+Bayol+Na$_2$CO$_3$+S1-9+sodium di(2-ethylhexyl)sulfosuccinate, A5+rapeseed oil methyl ester, for example Edenor or Actirob+Na$_2$CO$_3$+S1-9+sodium di(2-ethylhexyl)sulfosuccinate, A6+Solvesso+Na$_2$CO$_3$+S1-9+sodium di(2-ethylhexyl)sulfosuccinate, A6+Bayol+Na$_2$CO$_3$+S1-9+sodium di(2-ethylhexyl)sulfosuccinate, A6+rapeseed oil methyl ester, for example Edenor or Actirob+Na$_2$CO$_3$+S1-9+sodium di(2-ethylhexyl)sulfosuccinate, A7+Solvesso+Na$_2$CO$_3$+S1-9+sodium di(2-ethylhexyl)sulfosuccinate, A7+Bayol+Na$_2$CO$_3$+S1-9+sodium di(2-ethylhexyl)sulfosuccinate, A7+rapeseed oil methyl ester, for example Edenor or Actirob+Na$_2$CO$_3$+S1-9+sodium di(2-ethylhexyl)sulfosuccinate, A8+Solvesso+Na$_2$CO$_3$+S1-9+sodium di(2-ethylhexyl)sulfosuccinate, A8+Bayol+Na$_2$CO$_3$+S1-9+sodium di(2-ethylhexyl)sulfosuccinate, A8+rapeseed oil methyl ester, for example Edenor or Actirob+Na$_2$CO$_3$+S1-9+sodium di(2-ethylhexyl)sulfosuccinate, A9+Solvesso+Na$_2$CO$_3$+S1-9+sodium di(2-ethylhexyl)sulfosuccinate, A9+Bayol+Na$_2$CO$_3$+S1-9+sodium di(2-ethylhexyl)sulfosuccinate, A9+rapeseed oil methyl ester, for example Edenor or Actirob+Na$_2$CO$_3$+S1-9+sodium di(2-ethylhexyl)sulfosuccinate, A10+Solvesso+Na$_2$CO$_3$+S1-9+sodium di(2-ethylhexyl)sulfosuccinate, A10+Bayol+Na$_2$CO$_3$+S1-9+sodium di(2-ethylhexyl)sulfosuccinate, A10+rapeseed oil methyl ester, for example Edenor or Actirob+Na$_2$CO$_3$+S1-9+sodium di(2-ethylhexyl)sulfosuccinate, A11+Solvesso+Na$_2$CO$_3$+S1-9+sodium di(2-ethylhexyl)sulfosuccinate, A11+Bayol+Na$_2$CO$_3$+S1-9+sodium di(2-ethylhexyl)sulfosuccinate, A11+rapeseed oil methyl ester, for example Edenor or Actirob+Na$_2$CO$_3$+S1-9+sodium di(2-ethylhexyl)sulfosuccinate, A12+Solvesso+Na$_2$CO$_3$+S1-9+sodium di(2-ethylhexyl)sulfosuccinate, A12+Bayol+Na$_2$CO$_3$+S1-9+sodium di(2-ethylhexyl)sulfosuccinate, A12+rapeseed oil methyl ester, for example Edenor or Actirob+Na$_2$CO$_3$+S1-9+sodium di(2-ethylhexyl)sulfosuccinate, A13+Solvesso+Na$_2$CO$_3$+S1-9+sodium di(2-ethylhexyl)sulfosuccinate, A13+Bayol+Na$_2$CO$_3$+S1-9+sodium di(2-ethylhexyl)sulfosuccinate, A13+rapeseed oil methyl ester, for example Edenor or Actirob+Na$_2$CO$_3$+S1-9+sodium di(2-ethylhexyl)sulfosuccinate, A14+Solvesso+Na$_2$CO$_3$+S1-9+sodium di(2-ethylhexyl)sulfosuccinate, A14+Bayol+Na$_2$CO$_3$+S1-9+sodium di(2-ethylhexyl)sulfosuccinate, A14+rapeseed oil methyl ester, for example Edenor or Actirob+Na$_2$CO$_3$+S1-9+sodium di(2-ethylhexyl)sulfosuccinate, A1+Solvesso+-K$_2$CO$_3$+-S1-9+sodium di(2-ethylhexyl)-sulfosuccinate, A1+Bayol+K$_2$CO$_3$+S1-9+sodium di(2-ethylhexyl)sulfosuccinate, A1+rapeseed oil methyl ester, for example Edenor or Actirob+K$_2$CO$_3$+S1-9+sodium di(2-ethylhexyl)sulfosuccinate, A2+Solvesso+K$_2$CO$_3$+S1-9+sodium di(2-ethylhexyl)sulfosuccinate, A2+Bayol+K$_2$CO$_3$+S1-9+sodium di(2-ethylhexyl)sulfosuccinate, A2+rapeseed oil methyl ester, for example Edenor or Actirob+K$_2$CO$_3$+S1-9+sodium di(2-ethylhexyl)sulfosuccinate, A3+Solvesso+K$_2$CO$_3$+S1-9+sodium di(2-ethylhexyl)sulfosuccinate, A3+Bayol+K$_2$CO$_3$+S1-9+sodium di(2-ethylhexyl)sulfosuccinate, A3+rapeseed oil methyl ester, for example Edenor or Actirob+K$_2$CO$_3$+S1-9+sodium di(2-ethylhexyl)sulfosuccinate, A4+Solvesso+K$_2$CO$_3$+S1-9+sodium di(2-ethylhexyl)sulfosuccinate, A4+Bayol+K$_2$CO$_3$+S1-9+sodium di(2-ethylhexyl)sulfosuccinate, A4+rapeseed oil methyl ester, for example Edenor or Actirob+K$_2$CO$_3$+S1-9+sodium di(2-ethylhexyl)sulfosuccinate, A5+Solvesso+K$_2$CO$_3$+S1-9+sodium di(2-ethylhexyl)sulfosuccinate, A5+Bayol+K$_2$CO$_3$+S1-9+sodium di(2-ethylhexyl)sulfosuccinate, A5+rapeseed oil methyl ester, for example Edenor or Actirob+K₂CO₃+S1-9+sodium di(2-ethylhexyl)sulfosuccinate, A6+Solvesso+K₂CO₃+S1-9+sodium di(2-ethylhexyl)sulfosuccinate, A6+Bayol+K₂CO₃+S1-9+sodium di(2-ethylhexyl)sulfosuccinate, A6+rapeseed oil methyl ester, for example Edenor or Actirob+K₂CO₃+S1-9+sodium di(2-ethylhexyl)sulfosuccinate, A7+Solvesso+K₂CO₃+S1-9+sodium di(2-ethylhexyl)sulfosuccinate, A7+Bayol+K₂CO₃+S1-9+sodium di(2-ethylhexyl)sulfosuccinate, A7+rapeseed oil methyl ester, for example Edenor or Actirob+K₂CO₃+S1-9+sodium di(2-ethylhexyl)sulfosuccinate, A8+Solvesso+K₂CO₃+S1-9+sodium di(2-ethylhexyl)sulfosuccinate, A8+Bayol+K₂CO₃+S1-9+sodium di(2-ethylhexyl)sulfosuccinate, A8+rapeseed oil methyl ester, for example Edenor or Actirob+K₂CO₃+S1-9+sodium di(2-ethylhexyl)sulfosuccinate, A9+Solvesso+K₂CO₃+S1-9+sodium di(2-ethylhexyl)sulfosuccinate, A9+Bayol+K₂CO₃+S1-9+sodium di(2-ethylhexyl)sulfosuccinate, A9+rapeseed oil methyl ester, for example Edenor or Actirob+K₂CO₃+S1-9+sodium di(2-ethylhexyl)sulfosuccinate, A10+Solvesso+K₂CO₃+S1-9+sodium di(2-ethylhexyl)sulfosuccinate, A10+Bayol+K₂CO₃+S1-9+sodium di(2-ethylhexyl)sulfosuccinate, A10+rapeseed oil methyl ester, for example Edenor or Actirob+K₂CO₃+S1-9+sodium di(2-ethylhexyl)sulfosuccinate, A11+Solvesso+K₂CO₃+S1-9+sodium di(2-ethylhexyl)sulfosuccinate, A11+Bayol+K₂CO₃+S1-9+sodium di(2-ethylhexyl)sulfosuccinate, A11+rapeseed oil methyl ester, for example Edenor or Actirob+K₂CO₃+S1-9+sodium di(2-ethylhexyl)sulfosuccinate, A12+Solvesso+K₂CO₃+S1-9+sodium di(2-ethylhexyl)sulfosuccinate, A12+Bayol+K₂CO₃+S1-9+sodium di(2-ethylhexyl)sulfosuccinate, A12+rapeseed oil methyl ester, for example Edenor or Actirob+K₂CO₃+S1-9+sodium di(2-ethylhexyl)sulfosuccinate, A13+Solvesso+K₂CO₃+S1-9+sodium di(2-ethylhexyl)sulfosuccinate, A13+Bayol+K₂CO₃+S1-9+sodium di(2-ethylhexyl)sulfosuccinate, A13+rapeseed oil methyl ester, for example Edenor or Actirob+K₂CO₃+S1-9+sodium di(2-ethylhexyl)sulfosuccinate, A14+Solvesso+K₂CO₃+S1-9+sodium di(2-ethylhexyl)sulfosuccinate, A14+Bayol+K₂CO₃+S1-9+sodium di(2-ethylhexyl)sulfosuccinate, A14+rapeseed oil methyl ester, for example Edenor or Actirob+K₂CO₃+S1-9+sodium di(2-ethylhexyl)sulfosuccinate, A1+Solvesso+NaHCO₃+S1-9+sodium di(2-ethylhexyl)sulfosuccinate, A1+Bayol+NaHCO₃+S1-9+sodium di(2-ethylhexyl)sulfosuccinate, A1+rapeseed oil methyl ester, for example Edenor or Actirob+NaHCO₃+S1-9+sodium di(2-ethylhexyl)sulfosuccinate, A2+Solvesso+NaHCO₃+S1-9+sodium di(2-ethylhexyl)sulfosuccinate, A2+Bayol+NaHCO₃+S1-9+sodium di(2-ethylhexyl)sulfosuccinate, A2+rapeseed oil methyl ester, for example Edenor or Actirob+NaHCO₃+S1-9+sodium di(2-ethylhexyl)sulfosuccinate, A3+Solvesso+NaHCO₃+S1-9+sodium di(2-ethylhexyl)sulfosuccinate, A3+Bayol+NaHCO₃+S1-9+sodium di(2-ethylhexyl)sulfosuccinate, A3+rapeseed oil methyl ester, for example Edenor or Actirob+NaHCO₃+S1-9+sodium di(2-ethylhexyl)sulfosuccinate, A4+Solvesso+NaHCO₃+S1-9+sodium di(2-ethylhexyl)sulfosuccinate, A4+Bayol+NaHCO₃+S1-9+sodium di(2-ethylhexyl)sulfosuccinate, A4+rapeseed oil methyl ester, for example Edenor or Actirob+NaHCO₃+S1-9+sodium di(2-ethylhexyl)sulfosuccinate, A5+Solvesso+NaHCO₃+S1-9+sodium di(2-ethylhexyl)sulfosuccinate, A5+Bayol+NaHCO₃+S1-9+sodium di(2-ethylhexyl)sulfosuccinate, A5+rapeseed oil methyl ester, for example Edenor or Actirob+NaHCO₃+S1-9+sodium di(2-ethylhexyl)sulfosuccinate, A6+Solvesso+NaHCO₃+S1-9+sodium di(2-ethylhexyl)sulfosuccinate, A6+Bayol+NaHCO₃+S1-9+sodium di(2-ethylhexyl)sulfosuccinate, A6+rapeseed oil methyl ester, for example Edenor or Actirob+NaHCO₃+S1-9+sodium di(2-ethylhexyl)sulfosuccinate, A7+Solvesso+NaHCO₃+S1-9+sodium di(2-ethylhexyl)sulfosuccinate, A7+Bayol+NaHCO₃+S1-9+sodium di(2-ethylhexyl)sulfosuccinate, A7+rapeseed oil methyl ester, for example Edenor or Actirob+NaHCO₃+S1-9+sodium di(2-ethylhexyl)sulfosuccinate, A8+Solvesso+NaHCO₃+S1-9+sodium di(2-ethylhexyl)sulfosuccinate, A8+Bayol+NaHCO₃+S1-9+sodium di(2-ethylhexyl)sulfosuccinate, A8+rapeseed oil methyl ester, for example Edenor or Actirob+NaHCO₃+S1-9+sodium di(2-ethylhexyl)sulfosuccinate, A9+Solvesso+NaHCO₃+S1-9+sodium di(2-ethylhexyl)sulfosuccinate, A9+Bayol+NaHCO₃+S1-9+sodium di(2-ethylhexyl)sulfosuccinate, A9+rapeseed oil methyl ester, for example Edenor or Actirob+NaHCO₃+S1-9+sodium di(2-ethylhexyl)sulfosuccinate, A10+Solvesso+NaHCO₃+S1-9+sodium di(2-ethylhexyl)sulfosuccinate, A10+Bayol+NaHCO₃+S1-9+sodium di(2-ethylhexyl)sulfosuccinate, A10+rapeseed oil methyl ester, for example Edenor or Actirob+NaHCO₃+S1-9+sodium di(2-ethylhexyl)sulfosuccinate, A11+Solvesso+NaHCO₃+S1-9+sodium di(2-ethylhexyl)sulfosuccinate, A11+Bayol+NaHCO₃+S1-9+sodium di(2-ethylhexyl)sulfosuccinate, A11+rapeseed oil methyl ester, for example Edenor or Actirob+NaHCO₃+S1-9+sodium di(2-ethylhexyl)sulfosuccinate, A12+Solvesso+NaHCO₃+S1-9+sodium di(2-ethylhexyl)sulfosuccinate, A12+Bayol+NaHCO₃+S1-9+sodium di(2-ethylhexyl)sulfosuccinate, A12+rapeseed oil methyl ester, for example Edenor or Actirob+NaHCO₃+S1-9+sodium di(2-ethylhexyl)sulfosuccinate, A13+Solvesso+NaHCO₃+S1-9+sodium di(2-ethylhexyl)sulfosuccinate, A13 3+Bayol+NaHCO₃+S1-9+sodium di(2-ethylhexyl)sulfosuccinate, A13+rapeseed oil methyl ester, for example Edenor or Actirob+NaHCO₃+S1-9+sodium di(2-ethylhexyl)sulfosuccinate, A14+Solvesso+NaHCO₃+S1-9+sodium di(2-ethylhexyl)sulfosuccinate, A14+Bayol+NaHCO₃+S1-9+sodium di(2-ethylhexyl)sulfosuccinate, A14+rapeseed oil methyl ester, for example Edenor or Actirob+NaHCO₃+S1-9+sodium di(2-ethylhexyl)sulfosuccinate, A1+Solvesso+KHCO₃+S1-9+sodium di(2-ethylhexyl)sulfosuccinate, A1+Bayol+KHCO₃+S1-9+sodium di(2-ethylhexyl)sulfosuccinate, A1+rapeseed oil methyl ester, for example Edenor or Actirob+KHCO₃+S1-9+sodium di(2-ethylhexyl)sulfosuccinate, A2+Solvesso+KHCO₃+S1-9+sodium di(2-ethylhexyl)sulfosuccinate, A2+Bayol+KHCO₃+S1-9+sodium di(2-ethylhexyl)sulfosuccinate, A2+rapeseed oil methyl ester, for example Edenor or Actirob+KHCO₃+S1-9+sodium di(2-ethylhexyl)sulfosuccinate, A3+Solvesso+KHCO₃+S1-9+sodium di(2-ethylhexyl)sulfosuccinate, A3+Bayol+KHCO₃+S1-9+sodium di(2-ethylhexyl)sulfosuccinate, A3+rapeseed oil methyl ester, for example Edenor or Actirob+KHCO₃+S1-9+sodium di(2-ethylhexyl)sulfosuccinate, A4+Solvesso+KHCO₃+S1-9+sodium di(2-ethylhexyl)sulfosuccinate, A4+Bayol+KHCO₃+S1-9+sodium di(2-ethylhexyl)sulfosuccinate, A4+rapeseed oil methyl ester, for example Edenor or Actirob+KHCO₃+S1-9+sodium di(2-ethylhexyl)sulfosuccinate, A5+Solvesso+KHCO₃+S1-9+sodium di(2-ethylhexyl)sulfosuccinate, A5+Bayol+KHCO₃+S1-9+sodium di(2-ethylhexyl)sulfosuccinate, A5+rapeseed oil methyl ester, for example Edenor or Actirob+KHCO₃+S1-9+sodium di(2-ethylhexyl)sulfosuccinate, A6+Solvesso+KHCO₃+S1-9+sodium di(2-ethylhexyl)sulfosuccinate, A6+Bayol+KHCO₃+S1-9+sodium di(2-ethylhexyl)sulfosuccinate, A6+rapeseed oil methyl ester, for example Edenor or Actirob+KHCO₃+S1-9+sodium di(2-ethylhexyl)sulfosuccinate, A7+Solvesso+KHCO₃+S1-9+sodium di(2-ethylhexyl)sulfosuccinate, A7+Bayol+KHCO₃+S1-9+sodium di(2-ethylhexyl)sulfosuccinate, A7+rapeseed oil methyl ester, for example Edenor or Actirob+KHCO₃+S1-9+sodium di(2-ethylhexyl)sulfosuccinate, A8+Solvesso+KHCO$_3$+S1-9+sodium di(2-ethylhexyl)sulfosuccinate, A8+Bayol+KHCO$_3$+S1-9+sodium di(2-ethylhexyl)sulfosuccinate, A8+rapeseed oil methyl ester, for example Edenor or Actirob+KHCO$_3$+S1-9+sodium di(2-ethylhexyl)sulfosuccinate, A9+Solvesso+KHCO$_3$+S1-9+sodium di(2-ethylhexyl)sulfosuccinate, A9+Bayol+KHCO$_3$+S1-9+sodium di(2-ethylhexyl)sulfosuccinate, A9+rapeseed oil methyl ester, for example Edenor or Actirob+KHCO$_3$+S1-9+sodium di(2-ethylhexyl)sulfosuccinate, A10+Solvesso+KHCO$_3$+S1-9+sodium di(2-ethylhexyl)sulfosuccinate, A10+Bayol+KHCO$_3$+S1-9+sodium di(2-ethylhexyl)sulfosuccinate, A10+rapeseed oil methyl ester, for example Edenor or Actirob+KHCO$_3$+S1-9+sodium di(2-ethylhexyl)sulfosuccinate, A11+Solvesso+KHCO$_3$+S1-9+sodium di(2-ethylhexyl)sulfosuccinate, A11+Bayol+KHCO$_3$+S1-9+sodium di(2-ethylhexyl)sulfosuccinate, A11+rapeseed oil methyl ester, for example Edenor or Actirob+KHCO$_3$+S1-9+sodium di(2-ethylhexyl)sulfosuccinate, A12+Solvesso+KHCO$_3$+S1-9+sodium di(2-ethylhexyl)sulfosuccinate, A12+Bayol+KHCO$_3$+S1-9+sodium di(2-ethylhexyl)sulfosuccinate, A12+rapeseed oil methyl ester, for example Edenor or Actirob+KHCO$_3$+S1-9+sodium di(2-ethylhexyl)sulfosuccinate, A13+Solvesso+KHCO$_3$+S1-9+sodium di(2-ethylhexyl)sulfosuccinate, A13+Bayol+KHCO$_3$+S1-9+sodium di(2-ethylhexyl)sulfosuccinate, A13+rapeseed oil methyl ester, for example Edenor or Actirob+KHCO$_3$+S1-9+sodium di(2-ethylhexyl)sulfosuccinate, A14+Solvesso+KHCO$_3$+S1-9+sodium di(2-ethylhexyl)sulfosuccinate, A14+Bayol+KHCO$_3$+S1-9+sodium di(2-ethylhexyl)sulfosuccinate, A14+rapeseed oil methyl ester, for example Edenor or Actirob+KHCO$_3$+S1-9+sodium di(2-ethylhexyl)sulfosuccinate; A1+Solvesso+Na$_2$CO$_3$+S2-1+sodium di(2-ethylhexyl)sulfosuccinate, A1+Bayol+Na$_2$CO$_3$+S2-1+sodium di(2-ethylhexyl)sulfosuccinate, A1+rapeseed oil methyl ester, for example Edenor or Actirob+Na$_2$CO$_3$+S2-1+sodium di(2-ethylhexyl)sulfosuccinate, A2+Solvesso+Na$_2$CO$_3$+S2-1+sodium di(2-ethylhexyl)sulfosuccinate, A2+Bayol+Na$_2$CO$_3$+S2-1+sodium di(2-ethylhexyl)sulfosuccinate, A2+rapeseed oil methyl ester, for example Edenor or Actirob+Na$_2$CO$_3$+S2-1+sodium di(2-ethylhexyl)sulfosuccinate, A3+Solvesso+Na$_2$CO$_3$+S2-1+sodium di(2-ethylhexyl)sulfosuccinate, A3+Bayol+Na$_2$CO$_3$+S2-1+sodium di(2-ethylhexyl)sulfosuccinate, A3+rapeseed oil methyl ester, for example Edenor or Actirob+Na$_2$CO$_3$+S2-1+sodium di(2-ethylhexyl)sulfosuccinate, A4+Solvesso+Na$_2$CO$_3$+S2-1+sodium di(2-ethylhexyl)sulfosuccinate, A4+Bayol+Na$_2$CO$_3$+S2-1+sodium di(2-ethylhexyl)sulfosuccinate, A4+rapeseed oil methyl ester, for example Edenor or Actirob+Na$_2$CO$_3$+S2-1+sodium di(2-ethylhexyl)sulfosuccinate, A5+Solvesso+Na$_2$CO$_3$+S2-1+sodium di(2-ethylhexyl)sulfosuccinate, A5+Bayol+Na$_2$CO$_3$+S2-1+sodium di(2-ethylhexyl)sulfosuccinate, A5+rapeseed oil methyl ester, for example Edenor or Actirob+Na$_2$CO$_3$+S2-1+sodium di(2-ethylhexyl)sulfosuccinate, A6+Solvesso+Na$_2$CO$_3$+S2-1+sodium di(2-ethylhexyl)sulfosuccinate, A6+Bayol+Na$_2$CO$_3$+S2-1+sodium di(2-ethylhexyl)sulfosuccinate, A6+rapeseed oil methyl ester, for example Edenor or Actirob+Na$_2$CO$_3$+S2-1+sodium di(2-ethylhexyl)sulfosuccinate, A7+Solvesso+Na$_2$CO$_3$+S2-1+sodium di(2-ethylhexyl)sulfosuccinate, A7+Bayol+Na$_2$CO$_3$+S2-1+sodium di(2-ethylhexyl)sulfosuccinate, A7+rapeseed oil methyl ester, for example Edenor or Actirob+Na$_2$CO$_3$+S2-1+sodium di(2-ethylhexyl)sulfosuccinate, A8+Solvesso+Na$_2$CO$_3$+S2-1+sodium di(2-ethylhexyl)sulfosuccinate, A8+Bayol+Na$_2$CO$_3$+S2-1+sodium di(2-ethylhexyl)sulfosuccinate, A8+rapeseed oil methyl ester, for example Edenor or Actirob+Na$_2$CO$_3$+S2-1+sodium di(2-ethylhexyl)sulfosuccinate, A9+Solvesso+Na$_2$CO$_3$+S2-1+sodium di(2-ethylhexyl)sulfosuccinate, A9+Bayol+Na$_2$CO$_3$+S2-1+sodium di(2-ethylhexyl)sulfosuccinate, A9+rapeseed oil methyl ester, for example Edenor or Actirob+Na$_2$CO$_3$+S2-1+sodium di(2-ethylhexyl)sulfosuccinate, A10+Solvesso+Na$_2$CO$_3$+S2-1+sodium di(2-ethylhexyl)sulfosuccinate, A10+Bayol+Na$_2$CO$_3$+S2-1+sodium di(2-ethylhexyl)sulfosuccinate, A10+rapeseed oil methyl ester, for example Edenor or Actirob+Na$_2$CO$_3$+S2-1+sodium di(2-ethylhexyl)sulfosuccinate, A11+Solvesso+Na$_2$CO$_3$+S2-1+sodium di(2-ethylhexyl)sulfosuccinate, A11+Bayol+Na$_2$CO$_3$+S2-1+sodium di(2-ethylhexyl)sulfosuccinate, A11+rapeseed oil methyl ester, for example Edenor or Actirob+Na$_2$CO$_3$+S2-1+sodium di(2-ethylhexyl)sulfosuccinate, A12+Solvesso+Na$_2$CO$_3$+S2-1+sodium di(2-ethylhexyl)sulfosuccinate, A12+Bayol+Na$_2$CO$_3$+S2-1+sodium di(2-ethylhexyl)sulfosuccinate, A12+rapeseed oil methyl ester, for example Edenor or Actirob+Na$_2$CO$_3$+S2-1+sodium di(2-ethylhexyl)sulfosuccinate, A13+Solvesso+Na$_2$CO$_3$+S2-1+sodium di(2-ethylhexyl)sulfosuccinate, A13+Bayol+Na$_2$CO$_3$+S2-1+sodium di(2-ethylhexyl)sulfosuccinate, A13+rapeseed oil methyl ester, for example Edenor or Actirob+Na$_2$CO$_3$+S2-1+sodium di(2-ethylhexyl)sulfosuccinate, A14+Solvesso+Na$_2$CO$_3$+S2-1+sodium di(2-ethylhexyl)sulfosuccinate, A14+Bayol+Na$_2$CO$_3$+S2-1+sodium di(2-ethylhexyl)sulfosuccinate, A14+rapeseed oil methyl ester, for example Edenor or Actirob+Na$_2$CO$_3$+S2-1+sodium di(2-ethylhexyl)sulfosuccinate, A1+Solvesso+K$_2$CO$_3$+S2-1+sodium di(2-ethylhexyl)sulfosuccinate, A1+Bayol+K$_2$CO$_3$+S2-1+sodium di(2-ethylhexyl)sulfosuccinate, A1+rapeseed oil methyl ester, for example Edenor or Actirob+K$_2$CO$_3$+S2-1+sodium di(2-ethylhexyl)sulfosuccinate, A2+Solvesso+K$_2$CO$_3$+S2-1+sodium di(2-ethylhexyl)sulfosuccinate, A2+Bayol+K$_2$CO$_3$+S2-1+sodium di(2-ethylhexyl)sulfosuccinate, A2+rapeseed oil methyl ester, for example Edenor or Actirob+K$_2$CO$_3$+S2-1+sodium di(2-ethylhexyl)sulfosuccinate, A3+Solvesso+K$_2$CO$_3$+S2-1+sodium di(2-ethylhexyl)sulfosuccinate, A3+Bayol+K$_2$CO$_3$+S2-1+sodium di(2-ethylhexyl)sulfosuccinate, A3+rapeseed oil methyl ester, for example Edenor or Actirob+K$_2$CO$_3$+S2-1+sodium di(2-ethylhexyl)sulfosuccinate, A4+Solvesso+K$_2$CO$_3$+S2-1+sodium di(2-ethylhexyl)sulfosuccinate, A4+Bayol+K$_2$CO$_3$+S2-1+sodium di(2-ethylhexyl)sulfosuccinate, A4+rapeseed oil methyl ester, for example Edenor or Actirob+K$_2$CO$_3$+S2-1+sodium di(2-ethylhexyl)sulfosuccinate, A5+Solvesso+K$_2$CO$_3$+S2-1+sodium di(2-ethylhexyl)sulfosuccinate, A5+Bayol+K$_2$CO$_3$+S2-1+sodium di(2-ethylhexyl)sulfosuccinate, A5+rapeseed oil methyl ester, for example Edenor or Actirob+K$_2$CO$_3$+S2-1+sodium di(2-ethylhexyl)sulfosuccinate, A6+Solvesso+K$_2$CO$_3$+S2-1+sodium di(2-ethylhexyl)sulfosuccinate, A6+Bayol+K$_2$CO$_3$+S2-1+sodium di(2-ethylhexyl)sulfosuccinate, A6+rapeseed oil methyl ester, for example Edenor or Actirob+K$_2$CO$_3$+S2-1+sodium di(2-ethylhexyl)sulfosuccinate, A7+Solvesso+K$_2$CO$_3$+S2-1+sodium di(2-ethylhexyl)sulfosuccinate, A7+Bayol+K$_2$CO$_3$+S2-1+sodium di(2-ethylhexyl)sulfosuccinate, A7+rapeseed oil methyl ester, for example Edenor or Actirob+K$_2$CO$_3$+S2-1+sodium di(2-ethylhexyl)sulfosuccinate, A8+Solvesso+K$_2$CO$_3$+S2-1+sodium di(2-ethylhexyl)sulfosuccinate, A8+Bayol+K$_2$CO$_3$+S2-1+sodium di(2-ethylhexyl)sulfosuccinate, A8+rapeseed oil methyl ester, for example Edenor or Actirob+K$_2$CO$_3$+S2-1+sodium di(2-ethylhexyl)sulfosuccinate, A9+Solvesso+K$_2$CO$_3$+S2-1+sodium di(2-ethylhexyl)sulfosuccinate, A9+Bayol+K$_2$CO$_3$+S2-1+sodium di(2-ethylhexyl)sulfosuccinate, A9+rapeseed oil methyl ester, for example Edenor or Actirob+K$_2$CO$_3$+S2-1+sodium di(2-ethylhexyl)sulfosuccinate, A10+Solvesso+K$_2$CO$_3$+S2-1+sodium di(2-ethylhexyl)sulfosuccinate, A10+

Bayol+K$_2$CO$_3$+S2-1+sodium di(2-ethylhexyl)sulfosuccinate, A10+rapeseed oil methyl ester, for example Edenor or Actirob+K$_2$CO$_3$+S2-1+sodium di(2-ethylhexyl)sulfosuccinate, A11+Solvesso+K$_2$CO$_3$+S2-1+sodium di(2-ethylhexyl)sulfosuccinate, A11+Bayol+K$_2$CO$_3$+S2-1+sodium di(2-ethylhexyl)sulfosuccinate, A11+rapeseed oil methyl ester, for example Edenor or Actirob+K$_2$CO$_3$+S2-1+sodium di(2-ethylhexyl)sulfosuccinate, A12+Solvesso+K$_2$CO$_3$+S2-1+sodium di(2-ethylhexyl)sulfosuccinate, A12+Bayol+K$_2$CO$_3$+S2-1+sodium di(2-ethylhexyl)sulfosuccinate, A12+rapeseed oil methyl ester, for example Edenor or Actirob+K$_2$CO$_3$+S2-1+sodium di(2-ethylhexyl)sulfosuccinate, A13+Solvesso+K$_2$CO$_3$+S2-1+sodium di(2-ethylhexyl)sulfosuccinate, A13+Bayol+K$_2$CO$_3$+S2-1+sodium di(2-ethylhexyl)sulfosuccinate, A13+rapeseed oil methyl ester, for example Edenor or Actirob+K$_2$CO$_3$+S2-1+sodium di(2-ethylhexyl)sulfosuccinate, A14+Solvesso+K$_2$CO$_3$+S2-1+sodium di(2-ethylhexyl)sulfosuccinate, A14+Bayol+K$_2$CO$_3$+S2-1+sodium di(2-ethylhexyl)sulfosuccinate, A14+rapeseed oil methyl ester, for example Edenor or Actirob+K$_2$CO$_3$+S2-1+sodium di(2-ethylhexyl)sulfosuccinate, A1+Solvesso+NaHCO$_3$+S2-1+sodium di(2-ethylhexyl)sulfosuccinate, A1+Bayol+NaHCO$_3$+S2-1+sodium di(2-ethylhexyl)sulfosuccinate, A1+rapeseed oil methyl ester, for example Edenor or Actirob+NaHCO$_3$+S2-1+sodium di(2-ethylhexyl)sulfosuccinate, A2+Solvesso+NaHCO$_3$+S2-1+sodium di(2-ethylhexyl)sulfosuccinate, A2+Bayol+NaHCO$_3$+S2-1+sodium di(2-ethylhexyl)sulfosuccinate, A2+rapeseed oil methyl ester, for example Edenor or Actirob+NaHCO$_3$+S2-1+sodium di(2-ethylhexyl)sulfosuccinate, A3+Solvesso+NaHCO$_3$+S2-1+sodium di(2-ethylhexyl)sulfosuccinate, A3+Bayol+NaHCO$_3$+S2-1+sodium di(2-ethylhexyl)sulfosuccinate, A3+rapeseed oil methyl ester, for example Edenor or Actirob+NaHCO$_3$+S2-1+sodium di(2-ethylhexyl)sulfosuccinate, A4+Solvesso+NaHCO$_3$+S2-1+sodium di(2-ethylhexyl)sulfosuccinate, A4+Bayol+NaHCO$_3$+S2-1+sodium di(2-ethylhexyl)sulfosuccinate, A4+rapeseed oil methyl ester, for example Edenor or Actirob+NaHCO$_3$+S2-1+sodium di(2-ethylhexyl)sulfosuccinate, A5+Solvesso+NaHCO$_3$+S2-1+sodium di(2-ethylhexyl)sulfosuccinate, A5+Bayol+NaHCO$_3$+S2-1+sodium di(2-ethylhexyl)sulfosuccinate, A5+rapeseed oil methyl ester, for example Edenor or Actirob+NaHCO$_3$+S2-1+sodium di(2-ethylhexyl)sulfosuccinate, A6+Solvesso+NaHCO$_3$+S2-1+sodium di(2-ethylhexyl)sulfosuccinate, A6+Bayol+NaHCO$_3$+S2-1+sodium di(2-ethylhexyl)sulfosuccinate, A6+rapeseed oil methyl ester, for example Edenor or Actirob+NaHCO$_3$+S2-1+sodium di(2-ethylhexyl)sulfosuccinate, A7+Solvesso+NaHCO$_3$+S2-1+sodium di(2-ethylhexyl)sulfosuccinate, A7+Bayol+NaHCO$_3$+S2-1+sodium di(2-ethylhexyl)sulfosuccinate, A7+rapeseed oil methyl ester, for example Edenor or Actirob+NaHCO$_3$+S2-1+sodium di(2-ethylhexyl)sulfosuccinate, A8+Solvesso+NaHCO$_3$+S2-1+sodium di(2-ethylhexyl)sulfosuccinate, A8+Bayol+NaHCO$_3$+S2-1+sodium di(2-ethylhexyl)sulfosuccinate, A8+rapeseed oil methyl ester, for example Edenor or Actirob+NaHCO$_3$+S2-1+sodium di(2-ethylhexyl)sulfosuccinate, A9+Solvesso+NaHCO$_3$+S2-1+sodium di(2-ethylhexyl)sulfosuccinate, A9+Bayol+NaHCO$_3$+S2-1+sodium di(2-ethylhexyl)sulfosuccinate, A9+rapeseed oil methyl ester, for example Edenor or Actirob+NaHCO$_3$+S2-1+sodium.di(2-ethylhexyl)sulfosuccinate, A10+Solvesso+NaHCO$_3$+S2-1+sodium di(2-ethylhexyl)sulfosuccinate, A10+Bayol+NaHCO$_3$+S2-1+sodium di(2-ethylhexyl)sulfosuccinate, A10+rapeseed oil methyl ester, for example Edenor or Actirob+NaHCO$_3$+S2-1+sodium di(2-ethylhexyl)sulfosuccinate, A11+Solvesso+NaHCO$_3$+S2-1+sodium di(2-ethylhexyl)sulfosuccinate, A11+Bayol+NaHCO$_3$+S2-1+sodium di(2-ethylhexyl)sulfosuccinate, A11+rapeseed oil methyl ester, for example Edenor or Actirob+NaHCO$_3$+S2-1+sodium di(2-ethylhexyl)sulfosuccinate, A12+Solvesso+NaHCO$_3$+S2-1+sodium di(2-ethylhexyl)sulfosuccinate, A12+Bayol+NaHCO$_3$+S2-1+sodium di(2-ethylhexyl)sulfosuccinate, A12+rapeseed oil methyl ester, for example Edenor or Actirob+NaHCO$_3$+S2-1+sodium di(2-ethylhexyl)sulfosuccinate, A13+Solvesso+NaHCO$_3$+S2-1+sodium di(2-ethylhexyl)sulfosuccinate, A13+Bayol+NaHCO$_3$+S2-1+sodium di(2-ethylhexyl)sulfosuccinate, A13+rapeseed oil methyl ester, for example Edenor or Actirob+NaHCO$_3$+S2-1+sodium di(2-ethylhexyl)sulfosuccinate, A14+Solvesso+NaHCO$_3$+S2-1+sodium di(2-ethylhexyl)sulfosuccinate, A14+Bayol+NaHCO$_3$+S2-1+sodium di(2-ethylhexyl)sulfosuccinate, A14+rapeseed oil methyl ester, for example Edenor or Actirob+NaHCO$_3$+S2-1+sodium di(2-ethylhexyl)sulfosuccinate, A1+Solvesso+KHCO$_3$+S2-1+sodium di(2-ethylhexyl)sulfosuccinate, A1+Bayol+KHCO$_3$+S2-1+sodium di(2-ethylhexyl)sulfosuccinate, A1+rapeseed oil methyl ester, for example Edenor or Actirob+KHCO$_3$+S2-1+sodium di(2-ethylhexyl)sulfosuccinate, A2+Solvesso+KHCO$_3$+S2-1+sodium di(2-ethylhexyl)sulfosuccinate, A2+Bayol+KHCO$_3$+S2-1+sodium di(2-ethylhexyl)sulfosuccinate, A2+rapeseed oil methyl ester, for example Edenor or Actirob+KHCO$_3$+S2-1+sodium di(2-ethylhexyl)sulfosuccinate, A3+Solvesso+KHCO$_3$+S2-1+sodium di(2-ethylhexyl)sulfosuccinate, A3+Bayol+KHCO$_3$+S2-1+sodium di(2-ethylhexyl)sulfosuccinate, A3+rapeseed oil methyl ester, for example Edenor or Actirob+KHCO$_3$+S2-1+sodium di(2-ethylhexyl)sulfosuccinate, A4+Solvesso+KHCO$_3$+S2-1+sodium di(2-ethylhexyl)sulfosuccinate, A4+Bayol+KHCO$_3$+S2-1+sodium di(2-ethylhexyl)sulfosuccinate, A4+rapeseed oil methyl ester, for example Edenor or Actirob+KHCO$_3$+S2-1+sodium di(2-ethylhexyl)sulfosuccinate, A5+Solvesso+KHCO$_3$+S2-1+sodium di(2-ethylhexyl)sulfosuccinate, A5+Bayol+KHCO$_3$+S2-1+sodium di(2-ethylhexyl)sulfosuccinate, A5+rapeseed oil methyl ester, for example Edenor or Actirob+KHCO$_3$+S2-1+sodium di(2-ethylhexyl)sulfosuccinate, A6+Solvesso+KHCO$_3$+S2-1+sodium di(2-ethylhexyl)sulfosuccinate, A6+Bayol+KHCO$_3$+S2-1+sodium di(2-ethylhexyl)sulfosuccinate, A6+rapeseed oil methyl ester, for example Edenor or Actirob+KHCO$_3$+S2-1+sodium di(2-ethylhexyl)sulfosuccinate, A7+Solvesso+KHCO$_3$+S2-1+sodium di(2-ethylhexyl)sulfosuccinate, A7+Bayol+KHCO$_3$+S2-1+sodium di(2-ethylhexyl)sulfosuccinate, A7+rapeseed oil methyl ester, for example Edenor or Actirob+KHCO$_3$+S2-1+sodium di(2-ethylhexyl)sulfosuccinate, A8+Solvesso+KHCO$_3$+S2-1+sodium di(2-ethylhexyl)sulfosuccinate, A8+Bayol+KHCO$_3$+S2-1+sodium di(2-ethylhexyl)sulfosuccinate, A8+rapeseed oil methyl ester, for example Edenor or Actirob+KHCO$_3$+S2-1+sodium di(2-ethylhexyl)sulfosuccinate, A9+Solvesso+KHCO$_3$+S2-1+sodium di(2-ethylhexyl)sulfosuccinate, A9+Bayol+KHCO$_3$+S2-1+sodium di(2-ethylhexyl)sulfosuccinate, A9+rapeseed oil methyl ester, for example Edenor or Actirob+KHCO$_3$+S2-1+sodium di(2-ethylhexyl)sulfosuccinate, A10+Solvesso+KHCO$_3$+S2-1+sodium di(2-ethylhexyl)sulfosuccinate, A10+Bayol+KHCO$_3$+S2-1+sodium di(2-ethylhexyl)sulfosuccinate, A10+rapeseed oil methyl ester, for example Edenor or Actirob+KHCO$_3$+S2-1+sodium di(2-ethylhexyl)sulfosuccinate, A11+Solvesso+KHCO$_3$+S2-1+sodium di(2-ethylhexyl)sulfosuccinate, A11+Bayol+KHCO$_3$+S2-1+sodium di(2-ethylhexyl)sulfosuccinate, A11+rapeseed oil methyl ester, for example Edenor or Actirob+KHCO$_3$+S2-1+sodium di(2-ethylhexyl)sulfosuccinate, A12+Solvesso+KHCO$_3$+S2-1+sodium di(2-ethylhexyl)sulfosuccinate, A12+Bayol+KHCO$_3$+S2-1+sodium di(2-ethylhexyl)sulfosuccinate, A12+rapeseed oil methyl ester, for example Edenor or Actirob+KHCO$_3$+S2-1+sodium di(2-ethylhexyl)sulfosuccinate, A13+Solvesso+KHCO$_3$+S2-1+sodium di(2-ethylhexyl)sulfosuccinate, A13+Bayol+KHCO$_3$+S2-1+sodium di(2-ethylhexyl)sulfosuccinate, A13+rapeseed oil methyl ester, for example Edenor or Actirob+KHCO$_3$+S2-1+sodium di(2-ethylhexyl)sulfosuccinate, A14+Solvesso+KHCO$_3$+S2-1+sodium di(2-ethylhexyl)sulfosuccinate, A14+Bayol+KHCO$_3$+S2-1+sodium di(2-ethylhexyl)sulfosuccinate, A14+rapeseed oil methyl ester, for example Edenor or Actirob+KHCO$_3$+S2-1+sodium di(2-ethylhexyl)sulfosuccinate.

In the combinations mentioned above, it is also possible to combine a plurality of ALS inhibitors as component a) and to use them together for controlling harmful plants in crops of plants.

Thus, in a preferred embodiment, it is possible to combine, as component a), for example different sulfonamides of the formula (I) and/or salts thereof, for example
mesosulfuron-methyl+iodosulfuron-methyl,
mesosulfuron-methyl+iodosulfuron-methyl-sodium,
mesosulfuron-methyl+foramsulfuron,
mesosulfuron-methyl+foramsulfuron-sodium,
mesosulfuron-methyl-sodium+iodosulfuron-methyl,
mesosulfuron-methyl-sodium+iodosulfuron-methyl-sodium,
mesosulfuron-methyl-sodium+foramsulfuron,
mesosulfuron-methyl-sodium+foramsulfuron-sodium,
foramsulfuron+iodosulfuron-methyl,
foramsulfuron+iodosulfuron-methyl-sodium,
foramsulfuron-sodium+iodosulfuron-methyl,
foramsulfuron-sodium+iodosulfuron-methyl-sodium,
amidosulfuron+iodosulfuron-methyl,
amidosulfuron+iodosulfuron-methyl-sodium,
amidosulfuron-sodium+iodosulfuron-methyl,
amidosulfuron-sodium+iodosulfuron-methyl-sodium,
ethoxysulfuron+iodosulfuron-methyl,
ethoxysulfuron+iodosulfuron-methyl-sodium,
ethoxysulfuron-sodium+iodosulfuron-methyl,
ethoxysulfuron-sodium+iodosulfuron-methyl-sodium,
propoxycarbazone+mesosulfuron-methyl,
propoxycarbazone+mesosulfuron-methyl-sodium,
propoxycarbazone-sodium+mesosulfuron-methyl,
propoxycarbazone-sodium+mesosulfuron-methyl-sodium,
propoxycarbazone+iodosulfuron-methyl,
propoxycarbazone+iodosulfuron-methyl-sodium,
propoxycarbazone-sodium+iodosulfuron-methyl,
propoxycarbazone-sodium+iodosulfuron-methyl-sodium,
flucarbazone+mesosulfuron-methyl,
flucarbazone+mesosulfuron-methyl-sodium,
flucarbazone-sodium+mesosulfuron-methyl,
flucarbazone-sodium+mesosulfuron-methyl-sodium,
flucarbazone+iodosulfuron-methyl,
flucarbazone+iodosulfuron-methyl-sodium,
flucarbazone-sodium+iodosulfuron-methyl,
flucarbazone-sodium+iodosulfuron-methyl-sodium.

The ALS inhibitors a) and their mixtures, for example the active compound mixtures mentioned above of sulfonamides of the formula (I) and/or salts thereof, can be combined with one or more safeners, in particular with the safeners mefenpyr-diethyl (S1-1), isoxadifen-ethyl (S1-9) and cloquintocet-mexyl (S2-1).

The liquid formulations according to the invention can be prepared by known processes, for example by mixing the components. Thus, it is possible, for example, to dissolve components a) and c) and the optional components d), e) and f in any order in the solvent b). To accelerate the dissolution processes, it is possible to operate at elevated temperatures and using external forces, for example mixers. Depending on the dissolution properties of the individual components, it may be expedient to add the components in a certain sequence.

If not all components are soluble in the solvent b), preference is given to first dissolving the soluble components in solvent b) and dispersing the non-soluble components in this pre-solution. The resulting oil suspension can then, be subjected to wet grinding. To produce the formulation, it may be expedient to prepare appropriate pre-suspensions which comprise only certain amounts of the individual components. The components insoluble in the solvent can, if appropriate, be subjected to dry grinding prior to incorporation into the formulation; in certain cases, it may then be possible to dispense with the wet grinding.

To produce the mixtures, it is possible to use customary mixing apparatus which, if required, are thermostated. For pregrinding, it is possible to use, for example, high-pressure homogenizers or mills operating by the rotor-stator principle, such as Ultraturrax homogenizers, for example those from IKA, or toothed colloid mills, for example from Puck. For fine grinding, it is possible to use, for example, bead mills which operate batch-wise, for example from Drais, or bead mills which operate continuously, for example from Bachofen. The preparation process can be adapted to the properties of the components employed and to technical and safety requirements and to economical considerations, and pregrinding and even fine grinding may be dispensed with, if possible.

The components a) to f) used for the preparation may comprise water as a minor component which is then also found in the liquid formulations according to the invention. Accordingly, the liquid formulations according to the invention may comprise small amounts of water, in general from 0 to 5% by weight. If water is present, this is present in dissolved form, preferably in the organic solvent; i.e. the water does not form a continuous phase.

For application, the liquid formulations according to the invention may, if required, be diluted in a customary manner using, for example, water, to give, for example, emulsions, suspensions, suspoemulsions or solutions. It may be advantageous to add further agrochemically active compounds (for example tank mix components in the form of appropriate formulations) and/or auxiliaries and additives customary for application, for example self-emulsifying oils, such as vegetable oils or paraffin oils, and/or fertilizers to the spray liquors obtained. Accordingly, the present invention also provides such liquid herbicidal compositions based on the liquid formulations according to the invention.

The herbicidal compositions according to the invention (which hereinbelow in each case also include the liquid formulations according to the invention) have outstanding herbicidal activity against a broad spectrum of economically important monocotyledonous and dicotyledonous harmful plants. Even perennial weeds which produce shoots from rhizomes, rootstocks or other perennial organs and which are difficult to control are controlled well. In this context, it does not matter whether the substances are applied before sowing, pre-emergence or post-emergence. Specific examples may be mentioned of some representatives of the monocotyledonous and dicotyledonous weed flora which can be controlled by the herbicidal compositions according to the invention, without the enumeration being a restriction to certain species.

Examples of weed species on which the herbicidal compositions act efficiently are, from amongst the monocotyledonous weed species, *Apera spica venti, Avena* spp., *Alope-*

*curus* spp., *Brachiaria* spp., *Digitaria* spp., *Lolium* spp., *Echinochloa* spp., *Panicum* spp., *Phalaris* spp., *Poa* spp., *Setaria* spp. and *Bromus* spp. such as *Bromus catharticus, Bromus secalinus, Bromus erectus, Bromus tectorum* and *Bromus japonicus*, and *Cyperus* species from the annual group, and, among the perennial species, *Agropyron, Cynodon, Imperata* and *Sorghum* and also perennial *Cyperus* species.

In the case of the dicotyledonous weed species, the spectrum of action extends to species such as, for example, *Abutilon* spp., *Amaranthus* spp., *Chenopodium* spp., *Chrysanthemum* spp., *Galium* spp. such as *Galium aparine, Ipomoea* spp., *Kochia* spp., *Lamium* spp., *Matricaria* spp., *Pharbitis* spp., *Polygonum* spp., *Sida* spp., *Sinapis* spp., *Solanum* spp., *Stellaria* spp., *Veronica* spp. and *Viola* spp., *Xanthium* spp., among the annuals, and *Convolvulus, Cirsium, Rumex* and *Artemisia* in the case of the perennial weeds.

The compositions according to the invention also act outstandingly efficiently on harmful plants which are found under the specific cultures in rice, such as, for example, *Echinochloa, Sagittaria, Alisma, Eleocharis, Scirpus* and *Cyperus*.

If the herbicidal compositions according to the invention are applied to the soil surface before germination, the weed seedlings are either prevented completely from emerging or else the weeds grow until they have reached the cotyledon stage, but then their growth stops, and, eventually, after three to four weeks have elapsed, they die completely.

If the herbicidal compositions according to the invention are applied post-emergence to the green parts of the plants, growth likewise stops drastically a very short time after the treatment, and the weed plants remain at the growth stage at the point of time of application, or they die completely after a certain time, so that in this manner competition by the weeds, which is harmful to the crop plants, is eliminated very early and in a sustained manner.

The herbicidal compositions according to the invention are distinguished by a rapidly commencing and long-lasting herbicidal action. As a rule, the rainfastness of the active compounds in the herbicidal compositions according to the invention is advantageous. A particular advantage is that the dosages used in the herbicidal compositions and the effective dosages of herbicidal compounds can be adjusted to such a low level that their soil action is optimally low. This does not only allow them to be employed in sensitive crops in the first place, but groundwater contaminations are virtually avoided. The active compound combination according to the invention allows the required application rate of the active compounds to be reduced considerably.

The abovementioned properties and advantages are necessary for weed control practice to keep agricultural crops free from undesired competing plants, and thus to ensure and/or increase yield levels from the qualitative and quantitative angle. These novel compositions markedly exceed the technical state of the art with a view to the properties described.

While the herbicidal compositions according to the invention have an outstanding herbicidal activity against monocotyledonous and dicotyledonous weeds, crop plants of economically important crops, for example dicotyledonous crops such as soya, cotton, oilseed rape, sugar beet, or graminaceous crops such as wheat, barley, rye, oats, millet, rice or corn, are damaged only to a minor extent, if at all. This is why the present compounds are highly suitable for the selective control of undesired plant growth in plantations of agricultural crops or of ornamentals.

In addition, the herbicidal compositions according to the invention have outstanding growth-regulatory properties in crop plants. They engage in the plants' metabolism in a regulatory manner and can thus be employed for provoking direct effects on plant constituents and to facilitate harvesting such as, for example, by triggering desiccation and stunted growth. Moreover, they are also suitable for the general control and inhibition of undesired vegetative growth without simultaneously destroying the plants. Inhibition of vegetative growth is very important in a large number of monocotyledonous and dicotyledonous crops since lodging can thus be reduced, or prevented completely.

Owing to their herbicidal and plant-growth-regulatory properties, the herbicidal compositions according to the invention can also be employed for controlling harmful plants in crops of genetically modified plants which are known or yet to be developed. As a rule, the recombinant plants are distinguished by specific advantageous characteristics, for example by resistances to certain pesticides, in particular certain herbicides, resistances to plant diseases or the causative organisms of plant diseases such as specific insects or microorganisms such as fungi, bacteria or viruses. Other specific characteristics relate, for example, to the harvested material with regard to quantity, quality, storability, composition and specific constituents. Thus, for example, transgenic plants are known whose starch content is increased, or whose starch quality is altered, or those where the harvested material has a different fatty acid composition.

The use of the compositions according to the invention in economically important transgenic crops of useful plants and ornamentals, for example of graminaceous crops such as wheat, barley, rye, oats, millet, rice and corn, or else crops of sugarbeet, cotton, soya, oilseed rape, potatoes, tomatoes, peas and other vegetables, is preferred. Preferably, the compositions according to the invention can be employed as herbicides in crops of useful plants which resist the phytotoxic effects of the herbicides, or have been made to resist these effects by recombinant techniques.

When using the herbicidal compositions according to the invention in transgenic crops, effects are frequently observed in addition to the effects against harmful plants to be observed in other crops, which are specific for the application in the transgenic crop in question, for example a modified or specifically widened weed spectrum which can be controlled, modified application rates which may be employed for application, preferably good combining ability with the herbicides to which the transgenic crop is resistant, and an effect on growth and yield level of the transgenic crop plants.

The present invention furthermore also relates to a method for controlling unwanted vegetation (for example harmful plants, such as monocotyledonous or dicotyledonous weeds, unwanted crop plants), preferably in crops of plants such as cereals (for example wheat, barley, rye, oats, rice, corn and millet), sugar beet, sugar cane, oilseed rape, cotton and soya, particularly preferably in monocotyledonous crops such as cereals, for example wheat, barley, rye, oats, and their hybrids such as triticale, rice, corn and millet, where one or more herbicidal compositions according to the invention are applied to the plants (for example harmful plants), plant parts, seeds of the plants or the area on which the plants grow (for example the area under cultivation).

The plant crops may also be genetically modified or have been obtained by mutation selection; they preferably tolerate acetolactate synthase (ALS) inhibitors.

The liquid formulation of the present invention has excellent chemical stability during preparation and storage and has excellent physical stability, is easy to apply and easy to use and has high biological effectiveness and selectivity.

The invention is illustrated by the example below, but the example does not limit the invention. The abbreviations used in the examples are as defined below:

| | |
|---|---|
| iodosulfuron = | 3-(4-methoxy-6-methyl-1,3,5-triazin-2-yl)-1-(2-carboxy-5-iodophenylsulfonyl)urea sodium salt |
| mefenpyr = | ethyl 1-(2,4-dichlorophenyl)-5-(ethoxycarbonyl)-5-methyl-2-pyrazoline-3-carboxylate |
| 2,4-D isobutyl ester = | (2,4-dichlorophenoxy)acetic acid isobutyl ester |
| Bentone ® 34 = | modified phyllosilicate, Elementis |
| Morwet ® D425 = | naphthalene sulfate/formaldehyde condensate, Akzo Nobel |
| Emulsogen ® EL-400 = | polyethoxylated castor oil having 40 units of ethylene oxide, Clariant |
| Genapol ® V4739 = | polyethoxylated isotridecanol having 6 units of ethylene oxide, methoxy-capped, Clariant |
| Jeffsol ® PC = | propylene carbonate, Huntsman |
| Solvesso ® 200 = | aromatic mineral oil (boiling range 219-281° C.), Exxon |
| Triton ® GR-7M E = | di(2-ethylhexyl)sulfosuccinate sodium salt in aromatic solvent, Dow Chemicals |
| sodium carbonate = | $Na_2CO_3$, Fluka |

EXAMPLE 1

Preparation of a Liquid Formulation

A premix was prepared by dissolving all soluble components d), e) and f) in solvent b). After the dissolution process was complete, the solid ALS inhibitor a), the inorganic salt c) and, if appropriate, insoluble components were suspended in the mixture. The coarse suspension was, after pregrinding, subjected to fine grinding. The concentration of iodosulfuron was determined by HPLC after the liquid formulation had been prepared and stored at 40° C. for 8 weeks (8w40° C.).

TABLE 1

Chemical stability of component a) during preparation and storage (all amounts in % by weight)

| | Example 1.1 | Example 1.2 |
|---|---|---|
| 2,4-D isobutyl ester | 19.6 | 19.6 |
| iodosulfuron | 1.0 | 1.0 |
| mefenpyr | 3.0 | 3.0 |
| Solvesso ® 200 | 28.4 | 23.4 |
| Triton ® GR-7M E | 25.0 | 25.0 |
| Genapol ® V4739 | 20.0 | 20.0 |
| Emulsogen ® EL-400 | 3.0 | 3.0 |
| Jeffsol ® PC | — | 0.5 |
| Morwet ® D425 | — | 2.0 |
| Bentone ® 34 | — | 1.5 |
| sodium carbonate | — | 1.0 |
| concentration of iodosulfuron | | |
| after preparation | 0.98 | 1.0 |
| after 8 w 40° C. | 0.44 | 0.89 |

The invention claimed is:

1. A stable liquid formulation, comprising
   a) one or more herbicidally active compounds from the group of the ALS inhibitors,
   b) one or more organic solvents,
   c) one or more inorganic salts which, in a 1% strength aqueous solution, have a pH greater than 7, and are not used as fertilizers; and
   f) one or more customary auxiliaries and additives.

2. The liquid formulation of claim 1, wherein said formulation comprises
   a) one or more herbicidally active compounds selected from the group consisting of the sulfonamides,
   b) an organic solvent selected from the group consisting of aliphatic hydrocarbons, mixtures of aromatic and aliphatic hydrocarbons and vegetable oils,
   c) one or more inorganic salts selected from the group consisting of carbonates and bicarbonates,
   d) one or more agrochemically active compounds different from a), wherein said compounds are selected from the group consisting of one or more safeness and one or more herbicidally active compounds different from a),
   e) one or more sulfosuccinates, and
   f) one or more customary auxiliaries and additives.

3. The liquid formulation of claim 2, wherein component a), one or more herbicidally active compounds, is selected from the group consisting of iodosulfuron, propoxycarbazone, and flucarbazone.

4. The liquid formulation of claim 2, wherein component d), one or more agrochemically active compounds different from a), comprises a safener selected from the group consisting of mefenpyr and isoxadifen.

5. The liquid formulation of claim 2, wherein component c), one or more inorganic salts, comprises sodium carbonate.

6. The liquid formulation of claim 2, wherein component f, one or more customary auxiliaries and additives, comprises one or more surfactants.

7. The liquid formulation as claimed in claim 1 which comprises, as component a), one or more herbicidally active compounds from the group of the sulfonamides.

8. The liquid formulation as claimed in claim 7 which comprises, as component a), one or more herbicidally active compounds from the group of the triazolopyrimidinesulfonamides, sulfonylaminocarbonyltriazolinones and sulfonylureas.

9. The liquid formulation as claimed in claim 1 which comprises, as component b), one or more organic solvents selected from the group consisting of the unsubstituted or substituted hydrocarbons, polar solvents and fatty acid esters.

10. The liquid formulation as claimed in claim 1 which comprises, as component c), one or more inorganic salts selected from the group consisting of carbonates, bicarbonates, hydroxides, oxides, hypochlorites, and sulfites.

11. The liquid formulation as claimed in claim 1, which additionally comprises d) one or more agrochemically active compounds different from a).

12. The liquid formulation as claimed in claim 11 which comprises, as component d), one or more safeners.

13. The liquid formulation as claimed in claim 12 which comprises, as component d), one or more safeners selected from the group consisting of dichlorophenylpyrazoline-3-carboxylic acid and its esters, 5,5-diphenyl-2-isoxazoline-3-carboxylic acid and its esters and 8-quinolineoxyacetic acid and its esters.

14. The liquid formulation as claimed in claim 1, which additionally comprises component e) one or more sulfosuccinates.

15. The liquid formulation as claimed in claim 14 which comprises, as component e), one or more sulfosuccinates selected from the group consisting of mono- and diesters of sulfosuccinc acid.

16. The liquid formulation of claim 11, which additionally comprises component e) one or more sulfosuccinates.

17. A process for preparing a liquid formulation as claimed in claim 1, which comprises mixing component a) one or more herbicidally active compounds from the group of the ALS inhibitors; component b) one or more organic solvents; component c) one or more inorganic salts which, in a 1% strength aqueous solution have a pH greater than 7, and are not used as fertilizers; and component f) one or more customary auxiliaries and additives and, optionally, grinding the components.

18. A method for controlling unwanted vegetation, which comprises applying an effective amount of the liquid formulation as claimed in claim 1 to unwanted plants, to parts of unwanted plants, to unwanted seed or to an area on which unwanted plants grow.

19. A method for preparing a herbicidal composition comprising the step of preparing an emulsion, a suspension, a suspoemulsion or a solution comprising the liquid formulation of claim 1.

20. A liquid herbicidal composition, obtained by diluting a liquid formulation as claimed in claim 1.

21. The liquid herbicidal composition as claimed in claim 20 wherein the herbicidal composition is an emulsion, a suspension, a suspoemulsion or a solution.

22. The liquid herbicidal composition as claimed in claim 1, which additionally comprises component e) one or more sulfosuccinates.

23. The liquid herbicidal composition as claimed in claim 22 which comprises, as component e), one or more sulfosuccinates selected from the group consisting of the mono- and diesters of sulfosuccinc acid.

24. A liquid herbicidal composition comprising
a) one or more herbicidally active compounds from the group of the ALS inhibitors,
b) one or more organic solvents,
c) one or more inorganic salts which, in a 1% strength aqueous solution, have a pH greater than 7, and are not used as fertilizers;
f) one or more customary auxiliaries and additives; and water.

25. The liquid herbicidal composition as claimed in claim 24, which additionally comprises d) one or more agrochemically active compounds different from a).

26. The liquid herbicidal composition as claimed in claim 25 which comprises, as component d), one or more safeners.

27. The liquid herbicidal composition as claimed in claim 24 which comprises, as component d), one or more safeners selected from the group consisting of dichlorophenylpyrazoline-3-carboxylic acid and its esters, 5,5-diphenyl-2-isoxazoline-3-carboxylic acid and its esters and 8-quinolineoxyacetic acid and its esters.

28. The liquid herbicidal composition of claim 25, which additionally comprises component e) one or more sulfosuccinates.

29. A method for controlling unwanted vegetation which comprises applying an effective amount of the herbicidal composition as claimed in claim 24 unwanted to the plants, to parts of unwanted plants, to unwanted seed or to an area on which unwanted plants grow.

* * * * *